United States Patent [19]

Osther

[11] 4,132,769

[45] Jan. 2, 1979

[54] CANCER ANTIGEN, CANCER THERAPY, AND CANCER DIAGNOSIS

[76] Inventor: Kurt B. Osther, Højbjerggårdsvej 22, 2840 Holte, Denmark

[21] Appl. No.: 625,959

[22] Filed: Oct. 28, 1975

[30] Foreign Application Priority Data

Oct. 30, 1974 [DK] Denmark ............................. 5647/74
Feb. 25, 1975 [DK] Denmark .............................. 708/75
Apr. 11, 1975 [DK] Denmark ............................ 1574/75
Aug. 27, 1975 [DK] Denmark ............................ 3864/75
Jun. 10, 1975 [DK] Denmark ............................ 4503/75

[51] Int. Cl.$^2$ ..................... A61K 29/00; A61K 43/00
[52] U.S. Cl. .......................................... 424/1; 424/9; 260/112 R; 206/569; 23/230 B
[58] Field of Search .............. 260/112 R, 618; 424/1, 424/1.5, 9; 23/230 B, 259 R, 253 R

[56] References Cited

U.S. PATENT DOCUMENTS

| | | | |
|---|---|---|---|
| 2,165,370 | 7/1939 | Gruskin .................................... 424/9 |
| 3,663,684 | 5/1972 | Freedman et al. ....................... 424/1 |
| 3,697,638 | 10/1972 | Hansen ..................................... 424/1 |
| 3,852,415 | 12/1974 | Vandervoorde ......................... 424/1 |
| 3,867,363 | 2/1975 | Hansen .............................. 260/112 R |
| 3,927,193 | 12/1975 | Hansen ..................................... 424/1 |
| 3,956,258 | 5/1976 | Hansen .............................. 260/112 R |
| 3,960,827 | 6/1976 | Björklund ......................... 260/112 R |

*Primary Examiner*—Benjamin R. Padgett
*Assistant Examiner*—Christine M. Nucker
*Attorney, Agent, or Firm*—Hubbell, Cohen, Stiefel & Gross

[57] ABSTRACT

A novel human cancer associated protein, termed C1 IAC, having C1 inactivator-like function, diagnostic tests based on demonstrating the presence of C1 IAC, antibodies and antisera with specificity against C1 IAC, matrix-immobilized antibodies, and the therapy of human cancer using antisera or antibodies with specificity against C1 IAC. Also, a novel human cancer associated protein, termed CAAC, and antisera and antibodies with specificity against CAAC. The use of rabbit antihuman C1 IA and antihuman C4 for monitoring cancer diseases.

15 Claims, 31 Drawing Figures

RABBIT
ANTI C1 IA
1.5%

○ ○  1: C1 IAC + NEURAMINIDASE
2  1   2: C1 IAC

C1 IAC
+C1 IA

α₂HS glycoprotein
orosomucoid
C1 IAC
+C1 IA

1. PEAK          2. PEAK

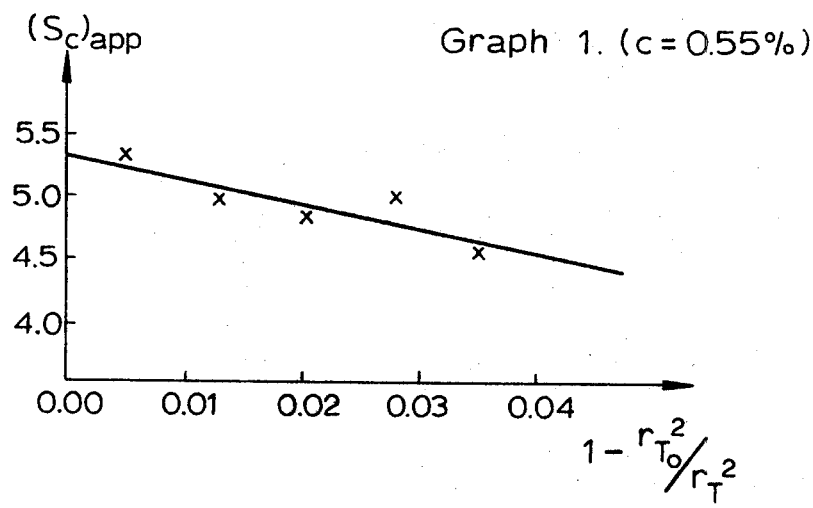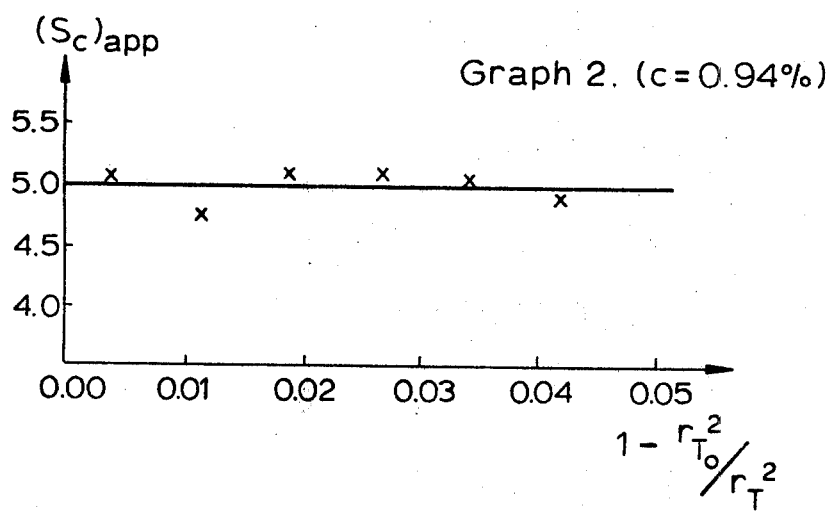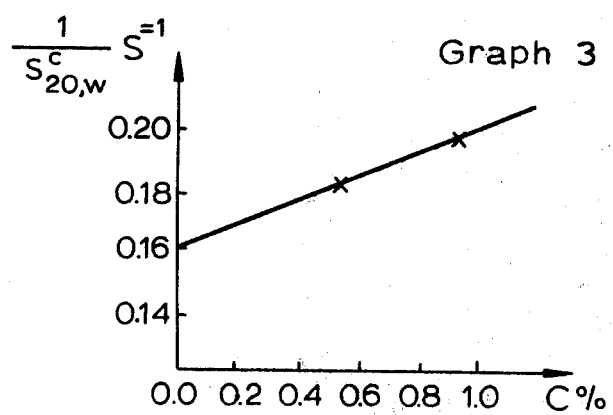
Fig. 15

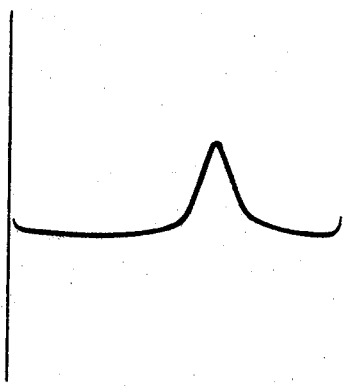
1st Experiment. Photo No. 4. t = 10 sec.
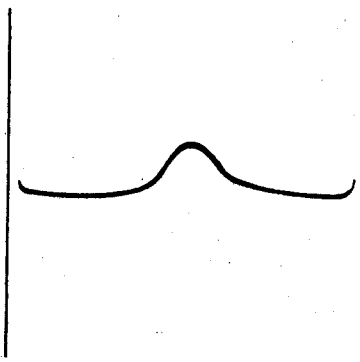
1st Experiment. Photo No. 6  t = 410 sec.
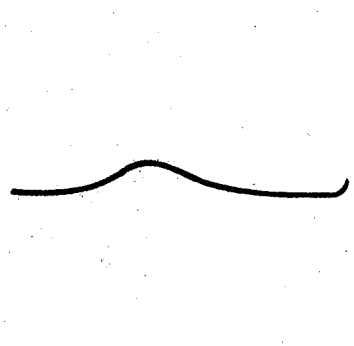
1st Experiment. Photo No. 8.  t = 810 sec.
Fig. 16

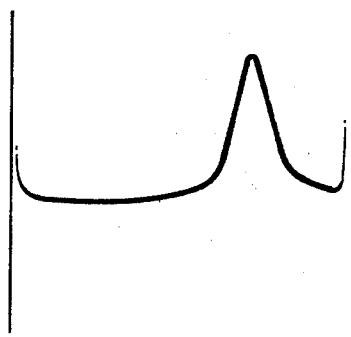
2nd Experiment. Photo No. 7.   t = 0 sec.
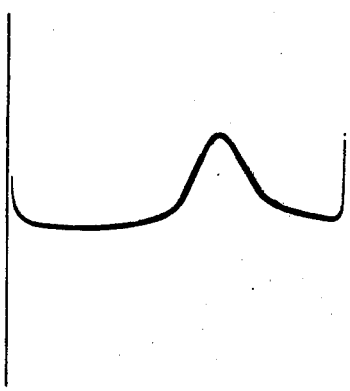
2nd Experiment. Photo No. 9   t = 402 sec.
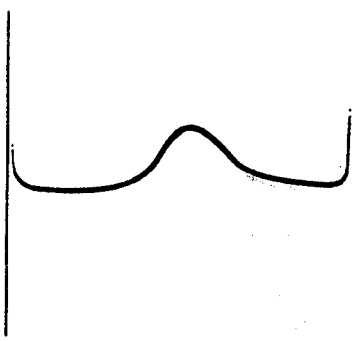
2nd Experiment. Photo No 11.   t = 804 sec.
Fig.17

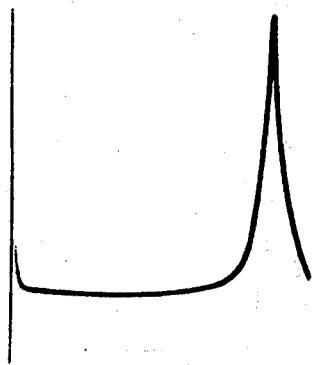
2nd Experiment. t<0 , 30000 rpm
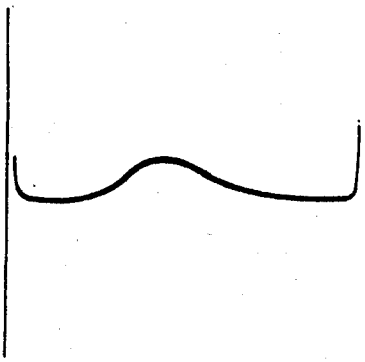
2nd Experiment. t = 1206 sec.
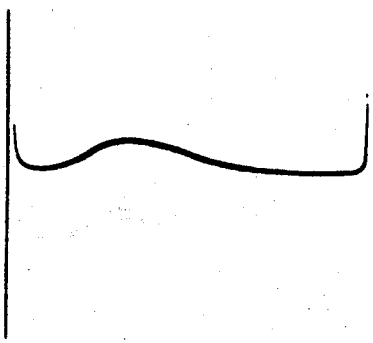
2nd Experiment. t = 1608 sec.
Fig. 18

CANCER ANTIGEN, CANCER THERAPY, AND CANCER DIAGNOSIS

The present invention relates to a human cancer associated protein, termed C1 IAC, to processes for its isolation and characterization, to diagnostic test methods and materials based on the principle of demonstrating the presence of C1 IAC, to antibodies and antisera with specificity against C1 IAC, to the preparation of such antibodies and compositions containing same, to matrix-immobilized antibodies, and to the therapy of human cancer using antisera or antibodies with specificity against C1 IAC.

Important aspects of the present invention are based upon the principle of utilizing antibodies directed specifically against blocking and masking proteins, in particular C1 IAC, associated with human cancer diseases and present on the membranes of cancer cells. According to the invention, this principle is utilized for treatment of cancer in vivo and for extracorporal treatment of cancer patient serum.

BRIEF DESCRIPTION OF THE DRAWINGS

FIG. 10 shows graphs from experiments for determining the sedimentation constant.

FIGS. 16-18 show photos from experiments for determining the sedimentation constant.

Figure 1:
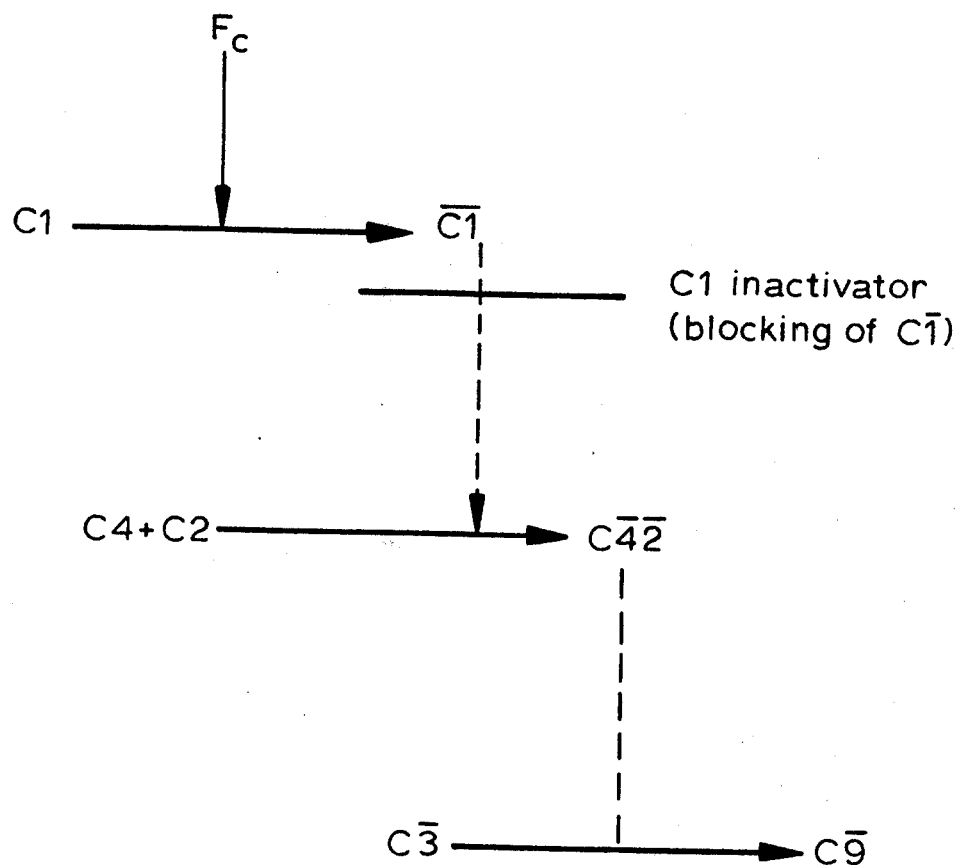
FIG. 1 is a representation of blocking of the complement system.

C1 IAC is a human cancer associated protein which may be isolated from body fluids of cancer patients, including serum, and from human malignant cancer cells, also from cell cultures. Repeated culturing and harvesting cycles of cell cultures have been performed and C1 IAC isolated from the culturing media, indicating that the cancer cells themselves are able to produce C1 IAC.

C1 IAC has been found to possess biological properties similar to the properties of human complement component C1 inactivator (also termed "C1 esterase inhibitor"), which is an $\alpha_2$ neuramino glycoprotein found in the body fluids of various species, including man (Pensky et al., J.Biol.Chem., 236, 1674, 1961, Ratnoff et al., J. Exp. Med. 129. 315, Pensky et al., Science 163, 698, 1969, Nagaki et al., Int.Arch.Allergy 46, 935, 1974), but to be protein-chemically non-identical with human complement component C1 inactivator.

In the following, human complement component C1 inactivator (C1 esterase inhibitor) will be termed "C1 IA", whereas the term "C1 inactivator", used in various contexts, shall designate the group consisting of C1 IAC and C1 IA.

C1 IAC has been found to possess biological properties similar to the properties of C1 IA, including the inhibitory effect on the initial human complement component C1 activation of C4 and C2 (i.e., inhibition of C1 esterase hydrolyzing effect), the inactivation of plasmin, and the lack of effect upon the clotting time of plasma (i.e., this lack is common to C1 IA and C1 IAC). In accordance with the principle upon which the present invention is based, it is believed that these inhibitory effects of C1 IAC play an important role in the cancer cell's defense against destruction by the human immune system.

In the literature, it has been described that a C1 IA-like protein is present on the membranes of human cancer cells (e.g., Osther, K., Højgaard, K., and Dybkjær, E., Acta neurol. Scand. 1974 50, 681, Osther, K., the Lancet, Mar. 2, 1974, p. 359, Osther, K., Linnemann, R., Acta path. microbiol. scand. 1973, 81, p. 365).

According to the present invention, said human cancer associated C1 IA-like protein has now been isolated and characterized, and as indicated above, it has been found to be a novel protein not identical with C1 IA. Important new developments are based upon these findings.

C1 IAC is an $\alpha$ (predominantly $\alpha_2$) neuraminoglycoprotein having a sedimentation constant of $s°_{20,w} = 6.2$ S. A complete characterization of C1 IAC, distinguishing C1 IAC from C1 IA and other known proteins, is given in the below section termed "Characterization of C1 IAC". By isoelectric focusing in LKB Multiphor, two separate bands were found by focusing in an ampholine of purified C1 IA and C1 IAC, the ampholine being PAG ® plate for thin layer polyacrylamide gel electrofocusing, pH gradient ranging from 4.0-8.6, 2 hours with cooling to 0° C. at 500 V, 50 mamps. After the electrophoresis, the polyacrylamide gel was cut out and subsequently run in an angle of 90° against 2% agarose gel in diemal buffer, ionic strength 0.02, pH 8.6 at 18° C. for 12 hours, the said agarose gel containing rabbit antihuman C1 IA. By this, two precipitation lines were obtained which do not cross, whereas identical runs, but with oligospecific antiserum against both C1 IA and C1 IAC, prepared on pig of "Dansk Landrace" ("Danish Landrace"), pig of mixed Yorkshire race and "Dansk Landrace", or of Texel type sheep ("Jysk Hederace") or mixed breeds sheep involving Shropshire and Oxford Down result in two precipitation lines which cross. This shows that, immunologically, the rabbit is not able to distinguish between C1 IA and C1 IAC, whereas the other animals mentioned are able to identify the two proteins as only partially identical. The fact that rabbit antiserum is not able to distinguish between C1 IAC and C1 IA plays an important role in the present context and is therefore emphasized. In reading the present specification, it is important to remember that a response, in immunological tests, based upon reaction with rabbit antihuman C1 IA (which is a commercially available reagent) will be a response to "C1 inactivator" or, in other words, a response to the sum of C1 IAC and C1 IA.

C1 IAC has been isolated from media from culturing of several types of human cancer cells, including carcinomas irrespective of origin, sarcomas of the type reticulo-lymphosarcom, and certain leucaemia types, namely cronic myeloid leucaemia and myelomatosis, and C1 IACs prepared from these cells have been found to be immunochemically identical.

For the isolation and purification of C1 IAC, several methods may be used. Common to all useful methods is that they comprise separation techniques aimed at isolating and purifying a pseudoglobulin material having the properties described in the section termed "Characterization of C1 IAC" from the medium in which it is found. Suitable methods comprise adsorption and gel filtration techniques which are well-known to the skilled art worker. As it has been shown that C1 IAC can be prepared from media from the culturing of human cancer cells, and also that no C1 IA can be isolated from media from culturing of such human cancer cells, one unambiguous method for concentrating, isolating and purifying C1 IAC is to use adsorption and gel filtration methods with concomitant immunological assay using rabbit antihuman C1 IA, for obtaining, from culturing media of the cancer cell types mentioned above, the protein reacting immunologically with the rabbit antihuman C1 IA. In such procedure, care should be taken to avoid pH values below 5.5 and above 10.5 and heating temperatures exceeding 56° C., as it has been shown, vide the section termed "Characterization of C1 IAC", that such conditions give rise to alterations of the biological properties of C1 IAC. When designing a suitable method for concentrating or purifying C1 IAC, the skilled art worker will also make use of other of the characterizing features stated in the section "Characterization of C1 IAC", including the estimated molecular weight of C1 IAC, which is 110,000–130,000. Evidence of the presence of C1 IAC in any material is obtainable using immunological tests against antibodies or antisera giving a reaction with C1 IAC which is readily distinguishable from the reaction with any other protein, including C1 IA. The preparation of such antibodies or antisera is described in the present specification. Suitable methods for concentrating, isolating and purifying C1 IAC employ column chromatography adsorption and gel filtration.

It is noted that C1 IA and C1 IAC have been found not to react with antibodies with specificity against other known antigens, especially not with antibodies against known oncofoetal antigens and, in particular, not with antibodies against $\alpha_1$ foetoprotein, or CEA protein.

A preferred method for the preparation of C1 IAC from a C1 IAC-containing medium is described in the section "Preparation of C1 IAC" and involves column chromatography adsorption and subsequent gel filtration. A preferred column for the column chromatography adsorption is an anion exchanger resin column such as Dowex 2 × 8, mesh 200–400, and a preferred gel material for the gel filtration is a dextran gel such as Sephadex ® G75 Superfine. Conventional unit operations are included in these procedures, e.g., dialysation and lyophilization at appropriate stages.

The medium from which C1 IAC may be concentrated, isolated and purified may be a culturing medium from culturing a C1 IAC-producing type of human cancer cells, or a body fluid such as serum or pleural/ascites exsudate from a patient suffering from a C1 IAC-producing cancer type. As explained above, the cancer cell culturing medium will not contain C1 IA, but C1 IA will be found together with C1 IAC in the body fluid from human cancer patients. For most of the practical utilities of C1 IAC, the presence of C1 IA in any starting medium used does not present any serious problem, because isolates containing C1 IA in addition to C1 IAC are valuable in themselves, such as will be explained below.

When cancer cells are cultivated for the production of C1 IAC, suitable culturing media are Eagle minimum essential medium and RPMI synthetic amino acid medium (vide Publication 73/74 from Flow Laboratories, Irvine Ayrshire, K.A. 12 8 NB, Scotland), but any other medium which will support the growth of the cancer cells may also be used. It has been found that the best yields of C1 IAC are obtained when the culturing medium contains added glutamine in an amount exceeding about 285 mg per liter, preferably exceeding 290 mg per liter. At present, the optimum amount of added glutamine has been found to be about 294 mg per liter, and addition of larger amounts does not seem to give any added advantages. Usual procedures for culturing cancer cells employ a growth phase in Eagle minimum essential medium enriched with added glutamine and a production phase in RPMI medium with added glutamine. Each phase may comprise a few days, e.g., 3–7 days; at present, 3 days is the preferred period.

As mentioned above, C1 IAC is believed to play an important role in cancer cells' defense against destruction by the human immune system. C1 IAC, being a sialoprotein (neuraminoglycoprotein), possesses low antigenicity, and it is believed that C1 IAC, together with other proteins found in cancer cell culturing media and in body fluids from cancer patients, especially orosomucoid, $\alpha_2$HS glycoprotein, and Zn $\alpha_2$ glycoprotein (also (obsolete) designated Zn $\alpha_3$ glycoprotein), "mask" the cancer cells against identification as "non-self" by the human immune system. Moreover, as has been mentioned above, C1 IAC is able to inhibit activation of C4 by C1, and this is believed to be one of the main reasons why cancer cells are not effectively attacked by the immune system.

Expressed in another manner, the ability of cancer cells to produce C1 IAC as a membrane protein may be one of the main reasons why these cancer cells possess the ability of blocking both the afferent limb and the efferent limb of the immune response. The afferent limb is apparently blocked mainly because of the masking effect of C1 IAC (symbody-effect), and the efferent limb seems to be blocked both at the humoral immune defense level and at the cellular immune response level, the former being a block of the complement system at the stage mentioned further above, and the latter being ascribable to the strongly negative electric charge of the cancer cell membrane due to the negatively charged C1 IAC and other strongly negatively charged sialo-compounds which will repel the negatively charged lymphocytes.

A schematical representation of the human complement system and the blocking and inhibitory action of C1 inactivator thereon is shown in FIG. 1. When a complement reaction has been initiated by the Fc fragment of an immunoglobulin, activated C1 will, in the normal course of a complement reaction or cascade, activate complement components C4 and C2 whereafter the complement reaction will proceed to end point and lysis of the "non-self" material or antigen with which the immunoglobulin had reacted, but C1 inactivator may inhibit C1's activation of C4, in which case C4 will not become attached to the antigen, and the further complement reactions will not proceed.

The body fluids of healthy human beings contain C1 IA as a necessary controller of the complement system. It is well established that the controlling effect of C1 IA in the healthy organism (said control effect manifesting itself via inhibition of C1r and C1s, resulting in lack of C1 activation of C4) is related to the concentration of C1 IA, and that normally, the inactivating effect of C1 IA on the C1 molecule is limited to inactivating any excess activation of C1 which could otherwise lead to a complement cascade in the serum phase, resulting in Quincke edema. Normal values of C1 IA in the serum phase are up to 40-50 mg%. In accordance with the present invention, it has now been found that patients suffering from verified cancer diseases often show abnormally high serum levels of C1 inactivator, all of which increase is probably ascribable to the C1 IAC present in the patient's serum.

Figure 2:
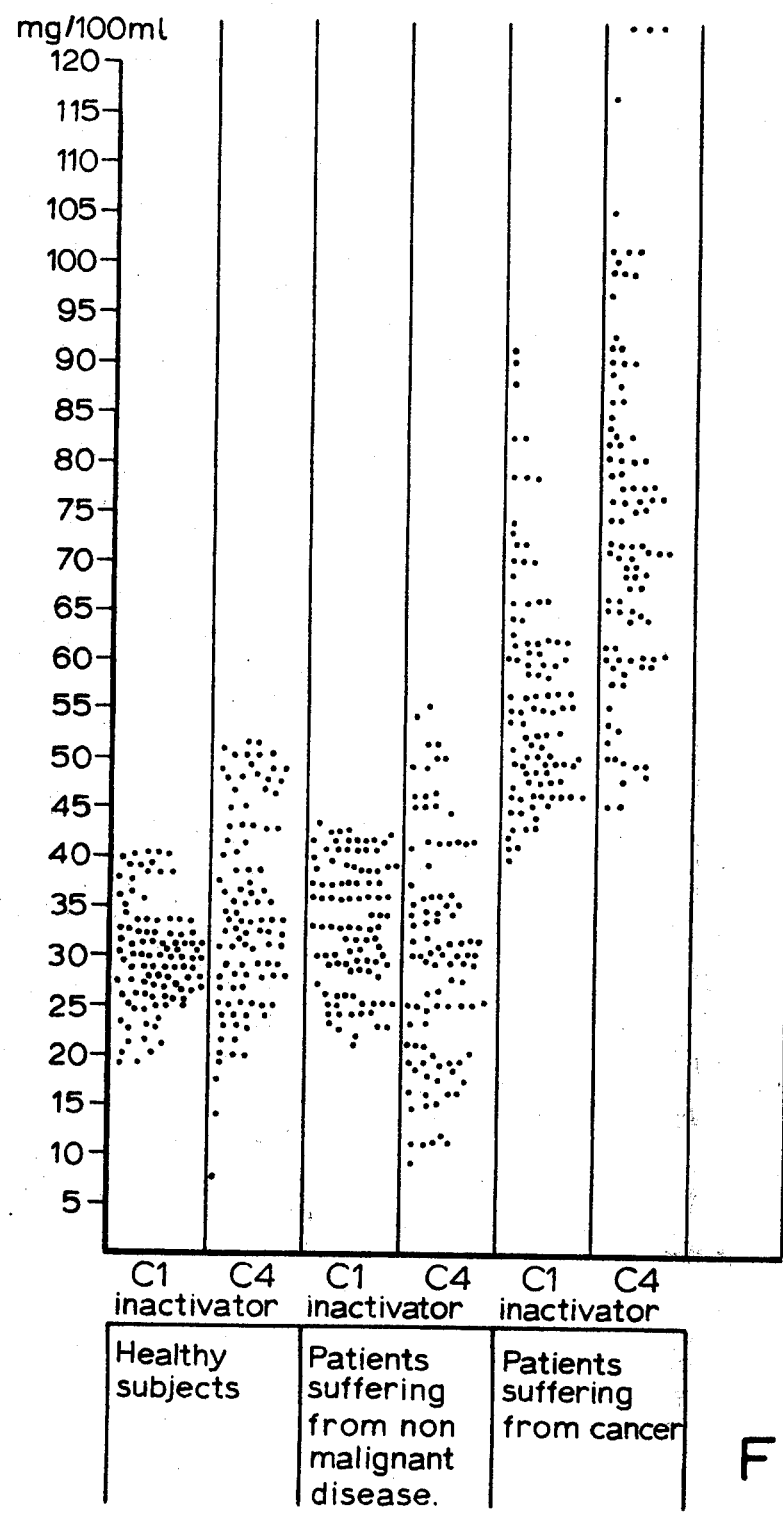
FIG. 2 shows levels of C1 inactivator in various patents.
Figure 3:
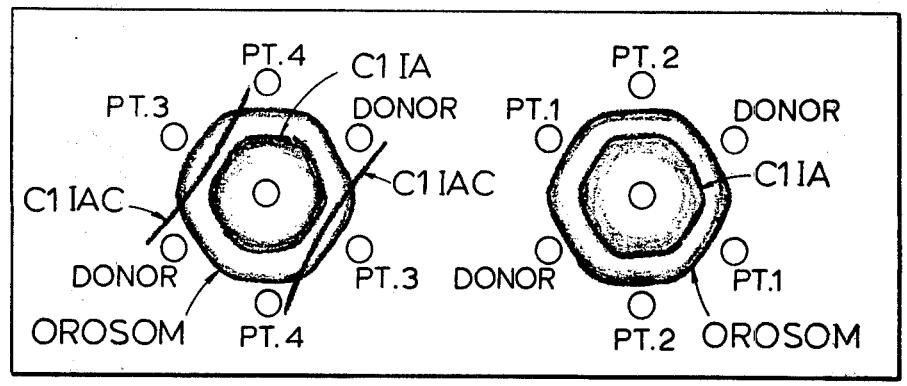
FIG. 3 is a Ouchterlony serum investigation.

In estimating to which extent patients suffering from verified cancer have elevated levels of C1 inactivator (C1 IA + C1 IAC), a hundred patients suffering from cancer of various origin, i.e., carcinomas, sarcomas, lymphomas, leucaemias, were checked for serum concentration of C1 inactivator, using Laurell rocket technique with rabbit antihuman C1 IA. Control experiments included equivalent examination of serum from healthy subjects and from patients suffering from verified non-malignant diseases. The results are shown in FIG. 2. It appears that the mean values of C1 inactivators from healthy subjects are much lower than from patients suffering from cancer. Also, patients suffering from non-malignant diseases showed C1 inactivator levels with mean values much below the cancer patients' and approximately in the normal range. The elevated concentrations of C1 inactivator in serum from patients suffering from cancer is believed to be mainly due to the presence of C1 IAC liberated from cancer cell clones. By Ouchterlony technique it was verified that the cancer patients found to have raised values of C1 inactivator revealed the precipitation lines for both C1 IA and C1/IAC, and that patients suffering from non-malignant diseases and healthy subjects did not show any presence of C1 IAC (both measured against oligo-specific sheep antihuman C1 IA/C1 IAC). A typical example of an Ouchterlony serum investigation of this type is shown in FIG. 3.

Estimations of the level of complement component C4, performed on the same groups of patients, showed almost the same mean values for healthy subjects and patients suffering from non-malignant diseases, whereas patients suffering from cancer showed significantly elevated C4 levels, vide FIG. 2.

It has been found that values of "C1 inactivator" (C1 IA + C1 IAC) exceeding concentrations of approximately 50 mg% (50 mg/100 ml) (as estimated by rocket electrophoresis using rabbit antihuman C1 IA) will often coincide with elevation of C4 indicating that the complement system is blocked at the C4 stage, i.e. at the stage where C1 activation of C4 should occur with consequent consumption of C4 (activated C4 becomes attached to the membranes of the cells to be lysed by the complement system). Investigating progressively growing cancer, it has been found that "C1 inactivator" and C4 rise continuously until death of the patient. It has also been found that subterminal and terminal values of C4 reach values up to 160 mg%, and C1 inactivator values up to approximately 120 mg%. In serum from some patients with verified cancer with primary small cancer cell clones, values of about 40-50 mg% of C1 inactivator (C1 IA + C1 IAC) have been ascertained without any signs of abnormally raised C4 levels; however, when these patients have been subjected to surgery, C1 inactivator levels either decline after a period of about 3 weeks and will remain in the normal range, concomitantly with C4 remaining in normal range (indicative of a successful radical operation), or an elevation of C1 inactivator accompanied with elevated C4 is found. The explanation of the latter phenomenon may be that a supposed radical operation may have elicited a raised concentration of C1 inactivator in the serum phase due to liberation of C1 IAC from damaged cancer cells and from cancer cells thrown into the blood stream, and that this increase in C1 inactivator concentration caused blocking of the complement system, vide above.

On the background of the above explanation, it will be understood that a radical increase in the chances of effectively treating cancer would be achieved if the inhibition of the immune response which takes place in case of cancer could be neutralized, that is, if the blocking of the immune defense could be obviated, and if the cancer cells could be "demasked" so that they were more readily recognized by the immunosurveillance of the human immune system. The present invention provides such deblocking and demasking.

As mentioned above, it has been found that the immune system of certain animals, including the pig and sheep races and types stated above, is able to distinguish between human C1 IA and human C1 IAC when introduced as antigens in the animals and hence, are able to produce antibodies with determinants with specificity against C1 IAC. Hence, an important aspect of the present invention relates to antisera or antibodies with specificity against C1 IAC. Such antisera may be produced by immunizing selectively immunizable animals, e.g., pigs or sheep of e.g. the above races and types, with vaccines containing C1 IAC as an antigenic component, and recovering serum from the immunized animals. Based upon the finding that orosomucoid, $\alpha_2HS$ glycoprotein, and Zn $\alpha_2$ glycoprotein are proteins which may be isolated from cancer cell culturing media, especially in the early stages of the culturing (before trypsinizing and subculturing), that these three proteins are notoriously proteins showing very low antigenicity, and that orosomucoid is present in high concentrations in pleura exsudate from cancer patients, these additional three proteins are believed to take part in the "masking" of cancer cells, for which reason it is preferred to include also these three proteins in the vaccines to be administered to the host animals for the preparation of the antisera for cancer therapy purposes, in order that the antisera will contain also antibodies against these three proteins. Furthermore, as it cannot be precluded that C1 IA will in several cases be the predominant C1 inactivator in the fluid phase, whereas C1 IAC is the C1 inactivator present on the cancer cells, it may be presumed that the most effective antiserum is one which is able to attack both C1 IAC and C1 IA.

In the following, the effect of the antisera or antibodies of the present invention will be explained in greater detail. For brevity and better survey, the term "INA" (immune neutralizing-deblocking antiserum) will be used to designate both the antisera specific to C1 IAC and optionally to C1 IA, orosomucoid, $\alpha_2HS$ glycoprotein and Zn $\alpha_2$ glycoprotein, and the more concentrated and purified immunoglobulin fractions thereof.

The antihuman C1 IAC antibodies react with C1 IAC on the cancer cell membrane, by an antigen-antibody reaction. For example, the interaction between INA and the cancer cells may be shown by marking INA (e.g. with FITC (Fluorescein Isothio cyanate)) and incubating the human cancer cells with the marked INA. The cancer cells will show positive marking. Cells from the same culture preincubated with neuraminidase do not show any marking after incubation with marked INA antiserum, which indicates that the antigenic determinants of C1 IAC are decomposed by neuraminidase. When INA blocks the determinants of the C1 IAC on the cancer cell membranes, the cancer cells become accessible to attack by the human humoral immune defense system, which is demonstrated, e.g., in the following manner: Human cancer cells are incubated with INA and thereafter incubated with serum from the same patient or from other patients with the same type of cancer. After incubation for e.g. 6 hours, the cancer cells become detached from the culture flask, and after e.g. 18 hours, all the cancer cells are dead. Mesothelial cells and fibroblasts treated in the same manner continue to grow in the culture flasks, undisturbed by the incubations, and in control cultures without incubation with INA, the incubation with serum did not affect the cancer cells. This proves that C1 IAC acts as an inhibiting factor and is involved in blocking the action of the immune system against cancer, and also, that INA is able to neutralize this blocking effect in vitro. When C1 IAC is neutralized by INA in vitro, its inhibitory effect on C1 activation of C4 is neutralized which means that the blocking of the action of the immune system ceases, C4 becomes attached to the cancer cell membranes, and the further action of the complement system takes place resulting in a lysis of the cancer cells; after the activation of C4, the complement reaction cannot be stopped by any influence from C1 IA or C1 IAC, vide FIG. 1.

Another way of demonstrating the in vitro cytotoxic effect of INA and the idem patient's serum and isolated lymphocytes against his cultivated cancer cells or leucaemia cells is using the method described by Hirschberg, H. et al., Nature 255, 62, 1975, incorporating $^{51}Cr$ into cytoplasma of the cancer or leucaemia cells. The release of $^{51}Cr$ into the medium wherein the neoplastic cells are incubated with INA and idem patient's serum and lymphocytes (isolated by Isopaque Ficoll method as described (Osther, K. and Dybkj r, E., Scand.J. Haematol. 13, 24, 1974) was measured by using scintillation technique. It was shown that the ability of cancer cell cytolysis was raised when the cells, in addition to INA incubation, were subjected to incubation with both humoral and cellular immune defense system. The experimental details are stated below:

Materials: INA pig immunoglobulin, prepared as described in the section "Vaccination of Host Animals".

$^{51}Cr$ in the form of $Na_2CrO_4$ from Behringwerke.

Methods: The model is human leucaemia cells. Neoplastic cells and lymphocytes were isolated from the same patient, serum freshly prepared from the same patient, lymphocytes isolated from donor, and serum freshly prepared from donor, the donor having the same ABO type as the patient; moreover, no leucocyte antibodies against the donor leucocytes were found in the patient serum. If leucocyte antibodies against the donor leucocytes had been found in the patient, the donor would have had to be exchanged with one against whom the patient did not have any leucocyte antibodies.

Controls: Negative control: $^{51}Cr$ labelled leucaemia cells in Eagle minimum essential medium.

Positive control: corresponding to 100% cytolysis (i.e. cytolysis of both normal cells and cancer cells) is obtained by addition of Cetavelon to $^{51}Cr$ labelled cells. Test material: From the patient venous blood was obtained in 3 citrate or heparin glasses and 1 glass without additives. From the donor, venous blood was obtained in 2 citrate or heparin glasses and 1 glass without additives.

Preparation of leucaemia cells and normal cells (= lymphocytes): The production was performed in accordance with the Ficoll-Isopaque method.

Marking of leucaemia cells (+ any normal lymphocytes present).

Marking of lymphocytes from donor: To about $2 \times 10^8$ cells were added $200\mu^{51}Cr$ + 1 ml of Eagle minimum essential medium, and the mixture was agitated and thereafter incubated in water bath at 37° C. for 30 minutes. Thereafter, the cells were washed until minumum release of $^{51}Cr$ (4 times). Washings performed in saline or Eagle minimum essential medium.

Incubation tests: The cells were incubated first with 0.2 ml of INA immunoglobulin (if applicable), and thereafter with 0.1 ml of serum, and 0.1 ml of lymphocyte suspension (if applicable) (the supernatant had been decanted from the lymphocytes which had been resuspended in 2.0 ml of Eagle minimum essential medium). All glasses contained the same volume = 1.4 ml; this is obtained by addition of extra Eagle minimum essential medium.

The Eagle minimum essential medium was admixed with 100 units of penicillin G and 10 $\mu g$ of streptomycin/ml.

The positive control is admixed with 0.4 ml of Cetavelon + 1 ml of labelled cells.

The negative control is admixed with 0.4 ml of Eagle minimum essential medium + 2 ml of labelled cells.

Incubation was performed for about 18 hours at 37° C. Measurement: Upon completion of the incubation, the samples were centrifugated for 10 minutes at 1800 rpm. Thereafter, aliquots of 1 ml of the supernatant were subjected to determination of $^{51}Cr$ release, using scintillation counter. The counts were adjusted for background.

Before removal of the supernatant, counts were made on the total contents of the glasses (1.4 ml).

Results:
(1) Patient suffering from myelomatosis.
Count after incubation, cpm.

|  | On 1.4 ml (total glass content) | On supernatant, 1 ml | % reduction |
| --- | --- | --- | --- |
| Negative control | 1697 | 539 | 32 |
| Positive control | 1572 | 901 | 57 |
| INA + patient serum | 1613 | 804 | 50 |
| INA + donor serum | 2033 | 884 | 44 |
| −INA + patient serum | 1600 | 521 | 33 |
| −INA + donor serum | 1719 | 578 | 34 |

The results show that the addition of INA immunoglobulin gives increase in cytolysis compared to the experiments without addition of INA immunoglobulins.
(2) Patient suffering from CML (Cronic Myeloid Leucaemia).
Count after incubation, cpm.

|  | On 1.4 ml (total glass content) | On supernatant, 1 ml | % reduction |
|---|---|---|---|
| Negative control | 2155 | 587 | 27 |
| Positive control | 2190 | 1404 | 64 |
| INA + donor lymphocytes + donor serum | 2104 | 668 | 32 |
| −INA + donor lymphocytes + donor serum | 2220 | 452 | 20 |
| INA + patient lymphocytes + patient serum | 2141 | 903 | 42 |
| −INA + patient lymphocytes + patient serum | 2040 | 610 | 30 |
| INA + donor serum | 2100 | 830 | 40 |
| −INA + donor serum | 2106 | 710 | 34 |
| INA + patient serum | 2149 | 809 | 38 |
| −INA + patient serum | 2102 | 659 | 31 |

The in vitro experiments described above show that the patient serum does contain antibodies against the patient's own neoplastic cells, and also show the cytotoxic effect exerted by both the humoral and the cellular immune system (the cellular immune system here being the lymphocytes and monocytes isolated by the Ficoll-Isopaque method). (The fact that the patient serum does contain antibodies against the neoplastic cells might perhaps seem to be paradoxial in view of the abovementioned fact that the cancer cells inhibit the afferent limb of the immune defence by "masking" themselves with C1 IAC and other proteins of extremely low antigenicity, but there are many possible reasons why a certain titre of antibody against cancer cell proteins will be present, e.g. chemical equilibrium and concentration factors, release of cancer cell proteins from cancer cells, including cancer cells which are dying or have become necrotic, or which have been ruptured by surgery, irradiation, cytostatic treatment, etc.). It is not possible from these experiments to evaluate whether a certain attachment of immunoglobulins on the cancer cell surface was present initially. At any rate, the presence of INA together with primarily the immune defense system derived from the cancer patient and secondly the immune system derived from the donor (complement source) gives rise to significant cytolysis of the neoplastic cells. Furthermore, it can be postulated that only a certain proportion of the total number of cells incubated as described were cytolysed, as evident from a comparison with the cytolysis obtained with Cetavelon, which may indicate that non-malignant cells survive the INA treatment.

When using non-malignant cells instead of the neoplastic cells, it has been found that no significant cytolysis takes place on INA incubation.

According to the invention, it has now been found that it is possible to obtain, by administration of INA to cancer patients, in vivo, excellent results in controlling and decreasing the amount of cancer cells. Various findings indicate that in the much more complex biological systems to be found in vivo, INA is able to exert activities similar to the ones ascertained in vitro.

Thus, the invention provides methods and compositions for the therapy of cancer by passive immunization against cancer cell masking and immune defense system-blocking proteins which is a totally new principle, not only in cancer therapy, but, as far as is known, in medicine as a whole.

Among the effects which have been observed after administration of INA to human cancer patients are:

(1) Decrease in serum concentration of "C1 inactivator" (the sum of C1 IAC + C1 IA, as measured with antiserum not distinguishing between C1 IAC and C1 IA, e.g., rabbit antihuman C1 IA), and decrease in serum concentration of C1 IAC as measured with monospecific antiserum against C1 IAC. Of course, in cases where an INA is used which is monospecific against C1 IAC, the decrease must be presumed to be resulting specifically from neutralization of C1 IAC, but as mentioned above, it is preferred to use INA which contains both anti C1 IAC and anti C1 IA. The said decrease in C1 inactivator usually occurs after an initial fast increase.

(2) Decrease in serum concentration of C4.

In addition, several manifestations of remissions, such as decrease in tumor mass and in some cases total disappearance of cancer cells, have been noted. However, the two above-mentioned levels of C1 inactivator, especially of C1 IAC, and C4 are important and easily determinable indicators of the course of the disease before, during, and after administration of INA, and, additionally, of any type of cancer therapy, such as is explained above. As an additional manifestation of remission it is seen that the low amount (low percentage) of T lymphocytes often found in patients suffering from cancer, especially upon cytostatic treatment or irradiation, will rise to normal values within a few weeks from the start of INA treatment.

The preparation of specific antibodies against C1 IAC, rendered possible by the present invention, also opens up the possibility of establishing an unambiguous diagnosis of cancer. According to the invention, this diagnosis is based upon the ascertainment of the presence or absence of C1 IAC in human body fluids, for practical purposes especially in human serum. According to the invention, the presence or absence of C1 IAC in a sample is ascertained by subjecting the sample to immunological reaction with antihuman C1 IAC under such conditions that the result of the immunological reaction is easily distinguishable from any response to C1 IA in the sample. This means that INA antiserum and other materials containing antibodies or immunologically active modifications or derivatives thereof are extremely valuable diagnostic materials. Further discussions of the diagnostic aspect of the present invention are given below.

For the preparation of the antisera according to the present invention it is important to use host animals which are able to distinguish, in their immune system, between C1 IAC and C1 IA, or, expressed in another manner, which are able to form specific antibodies against C1 IAC, and examples of such animals are mentioned above. It is to be noted that not all pig and sheep races and types seem to be able to produce useful antisera according to the present invention. Thus, e.g. a pig of pure Yorkshire race did not given any significant titer of antibody. Rabbits and small rodents have been found unable to distinguish between C1 IAC and C1 IA. On the other hand, it is believed that among horses and cows, races or types are found which will be able to distinguish between C1 IAC and C1 IA and to give reasonable antibody titres. Horses and cows are known to be generally good production animals for the preparation of antisera and show the advantage over pigs that they may be drained several times, whereas pigs are not so suitable for draining, but are usually bled. According to the principles of the present invention, the requirement to a host animal for use in the preparation of an INA antiserum of the invention is that the host animal gives specific response to C1 IAC. Moreover, the host animal should preferably be one, the antibodies of which are generally well tolerated by human beings. In this respect, pigs are preferred host animals, and in particular, pure pig IgG immonoglobulins (substantially unaggregated and substantially free of other pig proteins) have been found to be completely tolerable to human beings, and apparently to be classified as non-heterogenous by the human organism. (Apparently, the pure pig IgG immunoglobulins are not to any great extent transported to and decomposed in the liver, as would be the case with a heterogenous protein.

Further details concerning the preparation of antisera and antibodies according to the invention are given in the section "Vaccination of Host Animals" below. The vaccines used should be so composed that they produce a high antibody titer in the host animal in question, including a high antihuman C1 IAC titer. Preferred vaccines for the preparation an antisera in pigs and sheep are stated in the section "Vaccination of Host Animals", and the preparation of the active components of the vaccines are stated in the sections "Preparation of C1 IAC", "Purification of C1 IAC/C1 IA from Pleural-/Ascites Fluid from Cancer Patients", and "Purification of C1 IA/C1 IAC with a Content of Orosomucoid, $\alpha_2$HS Glycoprotein and Zn $\alpha_2$ Glycoprotein from Pleural/Ascites Fluid" below.

The antisera produced as described above are characterized in that they contain antihuman C1 IAC, i.e., antibodies which are able to react specifically with C1 IAC determinants. Such specific reaction can be demonstrated by several known immunological methods. In principle, it would be possible to subject the specific antihuman C1 IAC anitbodies, e.g. an antihuman C1 IAC IgG, to well-known anitbody splitting treatments which retain the specificity of the antibody, e.g. to produce the F(ab)2 fragment thereof. Depending upon the splitting treatment, the antibodies will or will not retain their ability to elicit complement system reaction. In principle, any such modification, derivative, or fragment of the antibodies according to the invention which has retained its specific ability to block C1 IAC determinants, will have utility in cancer therapy and diagnosis, because of its ability to trace cancer cells and to identify C1 IAC and neutralize the blocking activity of C1 IAC. In accordance with this, the antibodies, antibody fragments, antibody derivatives or antibody modifications according to the invention can be defined as such antibodies, fragments, modifications, or derivatives which are able to react with cultured cancer cells in such a manner that the cancer cells incubated with marked anti C1 IAC or marked fragments, modifications or derivatives thereof will show positive marking while cells from the same culture preincubated with neuraminidase will not show any marking after incubation with the marked material, and presaturation with unmarked antiserum against C1 IAC followed by incubation with the marked immunoglobulin or immunoglobulin fraction or immunoglobulin derivative or immunoglobulin modification according to the method described in Acta path. microbiol. scand., Section B, 81, 365-372, 1973, will not give rise to any marking of the cancer cells. As examples of modifications of the antibody according to the invention may be mentioned isotope labelled IgG antibodies (preferably labelled with an isotope of short half life when for in vivo use for diagnostic purposes, e.g. labelled with technetium) which may, because of their ability to trace cancer cells, be useful diagnostic materials for ascertaining the localization of tumors or metastases using, e.g., a $\gamma$ camera, and C1 IAC-specific IgG antibodies labelled with an isotope with a somewhat longer half life, e.g. a $\beta$-emitter such as $^{131}$I, for therapeutic use, or C1 IAC-specific IgG antibodies chemically combined with cytostatically active molecules, e.g. derivatives of known cytostatics, which $\beta$-emitter or cytostatic-carrying, C1 IAC-specific antibodies will open up the possibility of using $\beta$-emitters or cytostatics in a much more efficient and safe manner in that the $\beta$-emitters and the cytostatics are transported selectively to cancer cells (it will be recalled that normal cells are apparently not producers of C1 IAC).

A preferred composition according to the invention for therapy of human cancer is a pig IgG solution, 1000 mg IgG dissolved in about 200 ml isotonic saline (or equivalent, e.g. isotonic glucose). Such composition could practically be supplied in, e.g. 10 ml bottles for use in intravenous infusion diluted in the normal amounts of isotonic saline or equivalent. Another preferred composition is a lyophilized pig IgG immunoglobulin for reconstitution. Preferred administration ranges are about 20-30 mg of immunoglobulin per kg of patient body weight per day for the first about 5 days, and thereafter about 10 mg/kg body weight per day for about 2-3 weeks. In case the patient starts to produce antibodies against the host animal immunoglobulin introduced, cortisone should be administered, and anaphylactic shock therapy should be performed. However, no manifestations of anaphylaxi have been noted upon administration of the pig IgG immunoglobulins, not even after prolonged periods of intravenous administration with an intermittent pause of a fortnight.

During treatment with INA antiserum or antibodies, the patient is carefully monitored as described in the section "Cancer Therapy with Immune Serum According to the Invention", and especially important measured parameters are serum levels of C1 IAC and C4. By the successful treatment C1 IAC should be depleted and C4 lowered to normal values. Simultaneous treatment with cytostatics is not preferred according to the present invention due to the immunosuppressing effect of cytostatics. On the other hand, if cytostatic treatment is used, the patient should preferably be treated with INA during e.g. the last fortnight of the cytostatic treatment and continuously for a period of 1 or 2 months upon ceased cytostatic treatment in order to normalize the exhausted immune system including re-establishment of normal values of T lymphocytes. Cytostatics coupled to antihuman C1 IAC as selective carriers may, however, prove useful as they may be administered in much lower amounts than conventional cytostatics.

In order to monitor and adjust the immunoglobulin level of the patient, especially IgG must be assessed continuously, as the IgG concentration reflects both the human and the pig IgG content in serum. The purpose of such monitoring and adjustment is to secure that a sufficient amount of INA antiserum is administered for controlling and neutralizing the immune defense blocking and masking proteins, in particular C1 IAC, both in the humoral phase and on the cancer cell membranes. The necessary amount of INA antiserum must, hence, depend upon both the total mass and the activity (C1 IAC-producing ability) of the cancer cells.

The therapy experience obtained so far indicates that usually, the treatment with INA will be sufficient to obtain remission. However, it cannot be precluded that it would, at least in some cases where the patient's ability to produce antibodies is impaired, be advantageous to combine the treatment with INA with a treatment with pig IgG immunoglobulins with specificity against relevant cancer associated proteins other than C1 IAC, e.g. known cancer associated proteins such as foeto-proteins, CEA, or polypeptides such as CAPA, etc. (whenever found to be present), or pig IgG immunoglobulins obtained from pigs immunized with homogenisates of cancer cells or cancer tissue from the patient in question or from other patients suffering from the same type of cancer.

During treatment with INA, the patient should be checked for development of antibodies against the INA by known methods utilizing control pig IgG (from non-immunized pig of the same strain, using a haemagglutination test and if antibody formation is noted, the further treatment with INA may be performed by a novel principle according to the invention, i.e., immunoadherence to immobilized INA.

According to this principle, INA antiserum or antibodies may be applied to and immobilized with a matrix material, whereafter patient serum is passed through a column containing such matrix immobilized INA. The principle or removing proteins from patient serum by immunoadherence to matrix immobilized antibodies is believed to be novel and constitutes an aspect of the present invention. Further details concerning treatment with immobilized INA are given in the section "Extracorporal Deblocking and Demasking of Cancer Patient Serum" below. Although such extracorporal treatment will not neutralize C1 IAC present on cancer cell membranes, it will lower the general level of C1 inactivator (and preferably of orosomucoid, $\alpha_2$HS glycoprotein and Zn $\alpha_2$ glycoprotein) in the serum and thus improve the possibilities for the destruction of the cancer cells by the immune system. In this connection, and also in connection with the above explanation concerning therapeutical treatment with INA, it is to be remembered that concentration conditions and chemical equilibriums must probably play important roles in the reactions described.

Evidence of the fact that anti C1 IAC in INA serum is able to combine with cancer cells in vivo has been obtained:

In expectorate from one patient suffering from lung metastases from mammary carcinoma and treated with pig INA, cancer cells were found by histological methods. These cells were checked for pig globulins using anti-pig globulin which was FITC marked. By this method, the cells were identified as immunofluorescence positive. This proves that the INA induced in the patient was able to coat proteins on the cancer cells of the patient. Furthermore, no typical specific immunofluorescence could be detected using rabbit antihuman C1 IA-FITC. This is of special importance because cancer cells harvested from the pleura of this patient before treatment showed positive marking with rabbit antihuman C1 IA-FITC. These observations also indicate that an isotope marked INA injected into a patient will be able to trace cancer cells.

For the preparation of an antiserum or immunoglobulin product for diagnostical use in vivo, after isotope marking, e.g. with, preferably, technetium, which has a very short half life (4 hours) the vaccine used is preferably one which contains no C1 IA.

Preferred embodiments of a diagnostic kit according to the invention are given below in the section "Diagnostic Kits". Diagnostic kits according to the invention contain an antihuman C1 IAC material, the reaction of which with human C1 IAC in immunological test methods is readily distinguishable from the reaction with human C1 IA. One such material is monospecific antihuman C1 IAC (e.g. antihuman C1 IAC (absorbed)), which will give immunological reaction with C1 IAC, but not with C1 IA. Another material is, e.g. sheep antiserum containing antihuman C1 IAC and antihuman C1 IA, which will give, in various immunological methods, two precipitations with cancer patient serum, and only one precipitation with non-cancer serum. Antisera of the types here described may be used for a variety of immunological test methods, including hemagglutination test or RIA, Ouchterlony and Mancini immunodiffusion, immunoelectrophoreses, immunogelautoradiography, etc. The particular composition of such diagnostic compositions, materials or kits is evident to one skilled in the art, once it has been established that materials distinguishing between C1 IA and C1 IAC exist.

Using the comparative immunodiffusion diagnostic kit as described in the below section "Diagnostic Kits", several hundred serum investigations have been performed, and based upon the results so far obtained, the following may be stated Reliability.

The test shows a very high degree of reproducibility, of the order of 96% or more, which means that using one and the same serum sample for two independent test, the readings of the tests will, within 96% or more of the cases, be identical. Based upon this very high degree of reproducibility it must be said that the test according to the invention is very reliable. When the "reliability" of the test kit according to the invention is defined in a different manner, lower "reliability" values may be obtained. Thus, experience has shown that if serum from an "unselected patient material" is tested, generally about 80% of the test results will conform to the established diagnoses. However, this apparent lower degree of conformity is believed not to be an expression of any deficiency of the test. Partly, any non-conformity with established diagnosis may be due to the well-known fact that the sensitivity of an immunodiffusion test is dependent upon a visible precipitate, that is, that a sufficient concentration of the antigen must be present in the tested sample to produce a visible precipitation. Furthermore, a too high concentration of antigen in the tested sample may redissolve a precipitate, and equilibrium between antigen and antibody may be far beyond the titre of antiserum against the antigen in question. These problems may, however, in any particular cases where one has suspicion that they apply, be solved either by concentrating the sample (in the first-mentioned case) or by diluting the sample (in the second case). Partly, an apparent non-conformity may be explained as follows:

It must be remembered that what the test does is that it reflects the C1 IAC presence or non-presence in the patient serum (and moreover, in the comparative immunodiffusion embodiment described in the section "Diagnostic Kits", the positive C1 IAC reaction will also permit a semi-quantitative judgement). Based upon a proper understanding of the present invention, it must be presumed that a positive C1 IAC reaction found in the diagnostic test in indicative of an active state of C1 IAC-production in the patient, and such active state of C1 IAC-production may be detected by the test according to the invention at such an early stage of a cancer that it is not possible to ascertain or verify the cancer by any other known method. This may account for test results which would, at a first glance, be considered "false positive". Experience has shown that even among serum samples from about 200 blood donors, 2% of the samples, i.e. 4 samples, were found to be C1 IAC-positive, and 5% i.e. 10 serum samples to be doubtfully positive. Naturally, such finding implies that the blood donor in question should no longer be used as a blood donor, but should be examined for the reason of the C1 IAC in his serum found by the test according to the invention, and in fact, one preferred treatment according to the present invention would be an INA treatment at this early stage until the patient has no longer the positive C1 IAC reaction, i.e. a treatment based upon the finding of a positive C1 IAC test, before any cancer or other condition has had time to develop. It will always be advisable to check a C1 IAC-positive patient without any other signs of detectable cancer continously with the test according to the invention. Experience has also shown that certain types of virus, for example mononucleosis virus, are able to produce C1 IAC. In the case of mononucleosis, the C1 IAC test on the patient will be negative when the mononucleosis has been successfully overcome. This seems to indicate that the mononucleosis virus produces C1 IAC, and it is not unlikely thus a treatment with anti-C1 IAC pig IgG would be an effective therapi of mononucleosis. Other cases where a test performed according to the principles of the invention might at a first glance seem to be out of consistency with the established situation are cases where cancer patients show a negative C1 IAC reaction. However, the problematics in this case often reside in the definition of what is a "cancer patient". If a patient has been subjected to successful surgery with removal of primary tumors at a time where no metastases have developed, such patient will not have any reminiscences from the original cancer condition, and the patient's organism contains no cells which are producers of C1 IAC. Naturally, such a patient will have a negative C1 IAC response even though he may appear in hospitals files as a cancer patient. Other cases where negative C1 IAC tests would at a first glance seem to be incorrect results are cases where cancer patients are in remission so that their cancer cells are no longer productive of C1 IAC. Also, cancer patients with bone metastases which have been in steady state for years are often found negative in the immunodiffusion test according to the invention. As the test is designed for detecting the presence of C1 IAC in the patient material, the test will not give any positive result whenever no C1 IAC is present in the patient serum. A condition where no C1 IAC is present in the patient serum is, on the other hand, a condition where the patient's cancer is not active. Based upon these considerations it may be said that the C1 IAC diagnostic test according to the invention will give positive result for active cancer types which, when active, produce C1 IAC, and this seems to be by far most of the cancer types, such as will be explained below. As the test may be considered as being not only qualitative, but also semi-quantitative (and may be further developed into a quantitative test), these facts emphasize the importance of the test, in that the test is indicative of the serum concentration of exactly the protein which in several cancer types seems to be one of the main elements in the cancer cell's ability to escape, or defend itself against, destruction by the immune system.

More specifically, the experience from the serum investigations so far performed using the immunodiffusion diagnostic kit are the following:

The following cancer types have been found to be rather consistently C1-IAC-positive: carcinomas such as carcinoma mammae (breast carcinoma), carcinoma corporis uteri (uterin carcinoma), cancer pulmonis (bronchogenic carbinoma), cancer pancreatis (pancreatic cancer), cancer ventriculi (stomac cancer), hepatoma (primary liver cancer), cancer coli (colorectal cancer), cancer renis (kidney cancer), including pelvic carbinoma (carcinoma pelvis renis), and carcinoma vesicae urinariae (urinary bladder carcinoma), sarcomas (a few osteosarcomas and fibrosarcomas have been investigated and found weakly C1 IAC-positive). Osteosarcomas in remission (one case) is now negative after successful cytostatic treatment; before treatment, it was weakly positive. Testicular teratomas are strongly C1 IAC-positive. Melanomas: not all melanomas are found C1 IAC-positive. A few investigated cases of Hodgkins were found C1 IAC-positive. Neoplasma in infants: nephroblastoma were found C1 IAC-positive. Neuroblastoma were found C1 IAC-positive. Tumors within the central nervous system, for example astrocytoma and glioblastoma did not manifest themselves by positive C1 IAC-test on serum. Malignant diseases in blood and lymphsystem: acute myeloblastic leucaemia (AML) and chronic myeloid leucaemia (CML) are found to be C1 IAC-positive, except during the remission phase. Myelomatosis is also found C1 IAC-positive. Acute lymphoblastic leucaemia (ALL) and chronic lymphoblastic leucaemia are found C1 IAC-positive in 5–20% of total verified cases; it is noted that most of the cases of ALL so far investigated were cases in remission, whereas a few cases of active stages of ALL investigated were found to be significantly C1 IAC-positive. One case of acute lymphosarcom leucaemia was found to be C1 IAC-negative. Lymphomas are found to be weakly positive or, in some cases, significantly positive.

It is to be noted that one valuable feature of the diagnostic test according to the invention is that it permits a meaningful monitoring of the patient during any attempt of therapy. Experience has shown that cytostatic treatment of several diseases will not lower the C1 IAC titre in the patient if the tumors are not remissioned by the treatment. In other words, if the test according to the invention shows that there is no decrease in serum C1 IAC during an attempt of therapy, this is an indication that the therapy is not effective. It can also be said, based upon the above explanation of the invention, that the cancer types and stages which are C1-IAC-positive must be presumed to be those which are susceptible to successful therapy with anti-C1 IAC antiserum according to the invention.

It is interesting to note that an "autoimmune" disease such as LED (lupus erythromatosus disseminatus) shows a positive C1 IAC-reaction in about 30% of the cases. This is especially noteworthy in view of the fact that experimentally induced LED virus in mice will result in the development of LED in part of the inoculated mice, and in the development of lymphomas in the remainder of the inoculated mice. In investigations of the serum from about 200 patients from a neurological department, with a diversity of diseases ranging frm cerebral thrombosis, cerebral infarcts, to diseases such as multiple sclerosis gave about 2% positives, just like the result found in the blood donor group. The blood donor group consists of 200 blood donors, and as mentioned above, 4 C1 IAC-positive serum samples and 10 doubtfully positive serum samples were found. The sera from some of these C1 IAC-positive blood donors have been re-examined after some weeks, and at the re-examination, some of the previously positive sera from blood donors were later found C1 IAC-negative. Sera from about 50 patients with different types of allergic diseases ranging from asthma and exzema to urticarial rash (except Quincke type) were found C1 IAC-negative.

A total of 9 pregnant women have been examined and found negative except for 1 case, where the patient was found doubtfully positive.

In its broadest aspect, the invention relates to, what is believed to be novel, the principle of generating antisera and antibodies with specificity against cancer cell membrane proteins by isolating such cancer cell membrane proteins from culturing media from the culturing of cancer cells, of isolating the identical proteins, whenever found present, from body fluids from cancer patients, and utilizing such cancer cell membrane proteins as antigens in the immunizing of host animals, and subsequently harvesting serum from the host animal, said serum showing specificity against the cancer cell membrane proteins in question. Known attempts to generate anti sera and antibodies against cancer proteins have involved either immunizing host animals with living cancer cells or with homogenized cancer cells or tissue, and neither of these known measures will result in antisera or antibodies with specificity against cancer-produced or cancer-associated cancer cell membrane proteins with weak antigenicity. Further aspects of the invention in its broadest aspect then comprised the utilization of such antibodies or antisera as diagnostic reagents or materials or as therapeutical agents for passive immunization treatments.

The below detailed sections explain and illustrate various facts about and embodiments of the present invention, but are not to be construed as limiting.

PREPARATION OF C1 IAC.

Obtainment of human cancer cells for culturing.

Human cancer cells may be obtained from pleural or ascites fluid from patients suffering from cancer with metastases to pleura and/or ascites. The pleural/ascites fluid should be handled under sterile conditions, and infectious pleural/ascites fluids should be excluded. Separation of the cells from the fluid may be obtained by centrifugations at 1000 rpm for 10 minutes at room temperature. The precipitate contains the cells. The supernatant is discanted and stored at $-20°$ C. for later isolation of immunogenically valuable proteins therefrom as described in later sections.

Another source are solid human tumors removed from cancer patients by operation, for example, malignant brain tumors from patients suffering from primary malignant brain tumors. The cancer cells may be obtained from such tumors by trypsination. For example, the brain samples are washed several times in Eagle minimum essential medium (MEM) whereafter the tissue is cut into 1-2 mm cubes and resuspended in the medium after further washings and centrifugations, e.g., for 10 minutes at 900 rpm, trypsine solution may be added, whereafter incubation for e.g. 30 minutes at 25° C. is carried out, and the cell suspension may be filtered through sterile gauze admixed with a minimum of Eagle MEM with 15% bovine serum added, and centrifugated as mentioned above. The precipitate contains the cells, and the supernatant is discanted.

Each of the above precipitates may be used individually in the following procedure, or the precipitates may be pooled. Furthermore, human cancer cells obtained from other sources may be treated analogously and used per se or pooled with cancer cells obtained as described above.

Culturing of the cancer cells.

Cancer cells obtained as described above are explanted into 1000 ml Roux flasks containing Eagle MEM enriched with added glutamine (about 294 mg per liter) and containing 15% inactivated foetal calf serum and are incubated in incubator without $CO_2$ addition. For parallel test cultures, about 0.5 ml of the cell suspension is explanted directly on slides in a Leighton tube in order to examine a presence of C1 IAC on the cell membrane by immunofluorescence cytophotometri (Osther et al., Acta.path.microbiol. scand.B 81, 365, 1973). When the test cultures show the presence of C1 IAC, the main culture is used as production culture: The medium is removed, the cell structure is washed with PBS buffer, pH 7.3, and RPMI synthetic amino acid medium from Flow, Scotland, enriched with glutamine (about 294 mg/liter) but without any other admixture, is introduced, and incubation is performed for 3 days at 37° C., whereafter the medium is harvested under sterile conditions and centrifugated at 1000 rpm for 15 minutes at room temperature, whereafter the supernatant is stored in closed bottles at $-20°$ C. until isolation of C1 IAC is carried out. The cancer cell culture is further cultivated in the above-mentioned Eagle MEM modified medium, and after 3 days of incubation, the medium is again exchanged with glutamine-enriched RPMI medium, which is again harvested after 3 days of incubation and treated and frozen as described above for later isolation. In this manner, alternating culturing in Eagle MEM modified medium and RPMI glutamine-enriched medium and harvesting of the latter is carried out as long as the cancer cell culture is productive. In case of specially good growth (far over approximately $2 \times 10^5$ cells per Roux flask), explanting to further Roux culturing flasks is performed, and the resulting new cell cultures are also used for production in the same manner as described above. Throughout the procedure, the C1 IAC productivity of the culture cells is monitored by means of the test cultures in the Leighton tubes, and to the culturing media, penicillin and streptomycin are added is appropriate concentrations before use.

Isolation of C1 IAC.

The RPMI glutamine-enriched medium harvested from cancer cell cultures as described above is salted out to precipitate contaminating proteins, suitably to 40% saturation with saturated $(NH_4)_2SO_4$ at 0° C. with agitation. The medium so treated is centrifugated at 4000 rpm for 15 minutes at room temperature. Also other centrifugation procedures may be used, but the one stated has been found to give excellent results. The precipitate is discarded, and the supernatant is dialyzed for about 48 hours at 4° C. against numerous changes of distilled water and thereafter centrifugated at 3500 rpm at room temperature for 15 minutes. Also other centrifugation procedures are suitable, e.g. using a cooled centrifuge. Especially good purification is obtained in a cooled preparative ultracentrifuge.

In the further working up of C1 IAC from the clear supernatant, column chromatography absorption is the first stage. A preferred anion exchanger resin for this purpose is Dowex 2 × 8, mesh 200–400, but also other ion exchanger materials may be used. The ion exchanger resin is pretreated by boiling in water bath for 2 hours, 5 × 2 hours shift with 0.1 M HCl and thereafter equilibration by numerous shifts with agitation with Tris buffer 0.06 M, pH 7.3 until pH is stabilized about 7.3. Also other Tris buffers and phosphate buffers of different pH and ionic strength have also been used, but the above-mentioned buffer has been found optimal.

The above-mentioned clear supernatant is applied to the Dowex 2 × 8 anion exchanger resin column (K 50/100 with adaptors with a flow of the above-mentioned Tris buffer, pH 7.3, the flow rate being 100 ml per hour at room temperature. The best yield of C1 IAC is obtained using 160 ml of RPMI medium per 1500 ml of column material. The effluent from the column passes through a flow-through micro cuvette of a spectrophotometer which graphically records the optical density at 580 nm of the effluent (an Isco spectrophotometer was used) and is collected in 10 ml fractions in a fraction collector. In this and the following fractionations, eluted proteins detected as optical density peaks in the spectrophotometer are checked for C1 IAC by rocket immunoelectrophoresis using rabbit antihuman C1 IA, pig antihuman C1 IAC or sheep antihuman (absorbed) C1 IAC (prepared as described further below) in the gel and for contaminating proteins by Freeman crossed immunoelectrophoresis using antihuman whole protein serum in the gel and Grabar immunoelectrophoresis using the two above-mentioned types of antisera. The contaminating proteins are suitably checked for presence of orosomucoid, transferrin, $\alpha_2$HS glycoprotein, inter-$\alpha$-trypsin inhibitor, prealbumin, and albumin.

The main part of C1 IAC is absorbed in the ion exchanger. By repeated passage through the ion exchanger in Tris buffer, the remainder may be absorbed.

Figure 5:
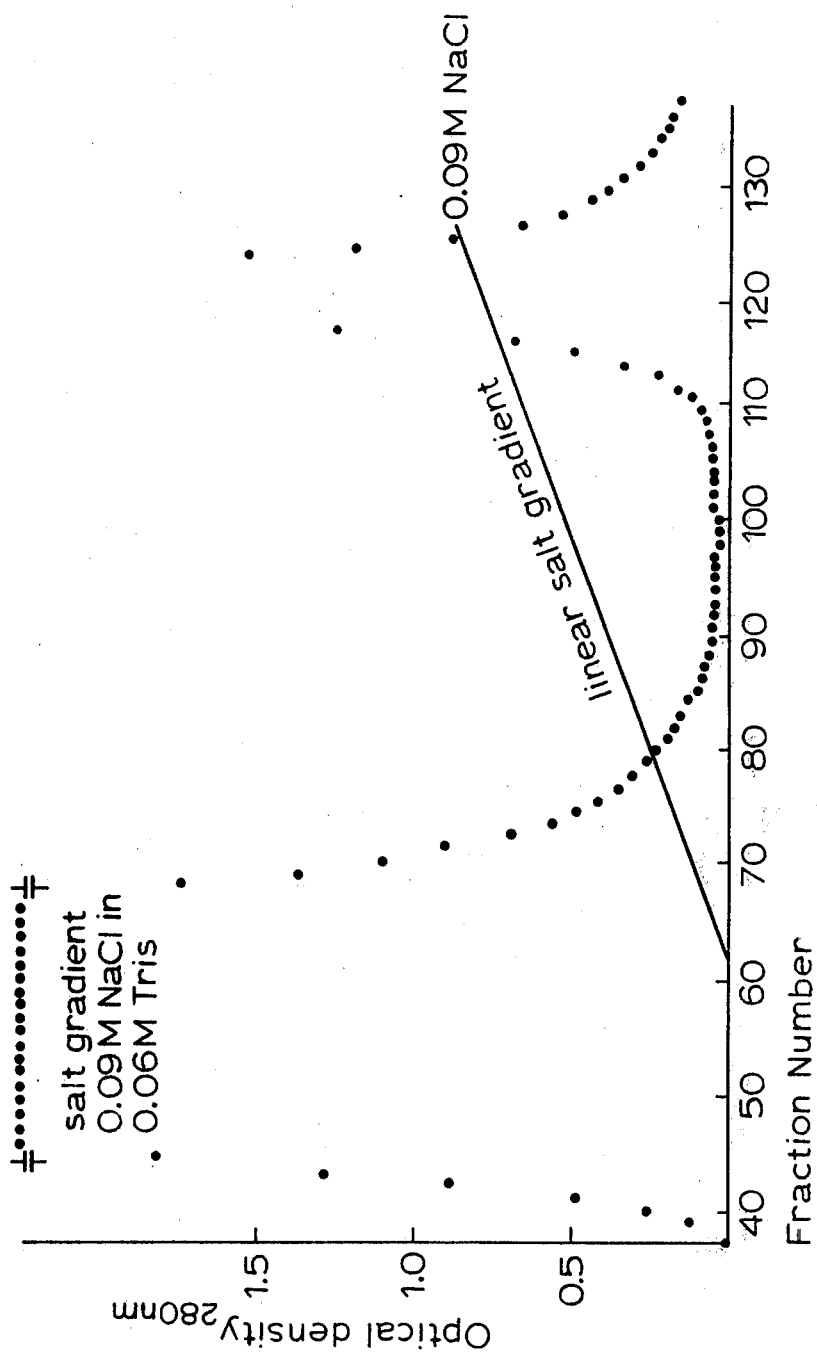
FIGS. 5 and 6 are spectrophotometrical graphs.

Most of the contaminating proteins appear in a first major elution peak in the elution with Tris buffer. A typical spectrophotometrical graph of this elution is shown in FIG. 5. After a suitable number of fractions following the appearance of the peak, a straight ascending concentration of NaCl until an end pont of 0.09 M NaCl is added to the column. The above-mentioned "suitable" number of fractions is a number of fractions which will secure proper separation of the first peak and the subsequently eluted protein. Also other models of additional salt concentration, including stepwise increase, may be used, but with no additional advantage C1 IAC is liberated from the ion exchanger at the end point at about 0.09 M NaCl (as shown by a minor peak in the spectrophotometrical graph, vide FIG. 5), and the fractions containing C1 IAC are pooled and dialyzed for about 24 hours at 4° C. against distilled water. Thereafter, the dialyzed product is lyophilized (shell lyophilization using vacuum and gentle external heating at 40° C. was found to be a suitable procedure).

Figure 6:
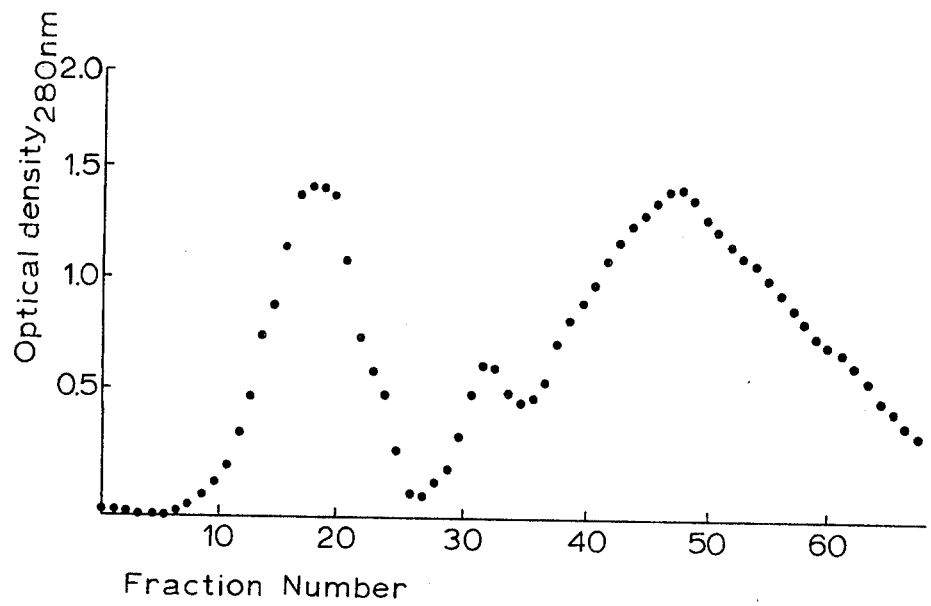

The lyophilisate is resuspended in 0.06 M Tris buffer, pH 8.6, and applied on a Sephadex ® G75 Superfine gel filtration dextrane column such as a Pharmacia K 15/50 column, using the Tris buffer, pH 8.6, as effluent buffer. The flow rate is suitably about 10 ml per hour. The effluent was monitored with the spectrophotometer and examined by immunoelectrophoresis techniques as described above. A typical spectrophotometrical recording of the optical density of the effluent is shown in FIG. 6, in which the first peak represents C1 IAC. The fractions rich in C1 IAC are collected, dialyzed exhaustively against distilled water (48 hours) and lyophilized as described above. In the following, this product is designated "C1 IAC (Sephadex ®G75 Superf.)" or "C1 IAC$_{pure}$". According to immunoelectrophoretical estimation, this product is pure and non-aggregated.

In an alternative purification procedure, the above-mentioned lyophilisate of the dialyzed C1 IAC-containing fractions from the Dowex 2 × 8 ion exchanger is resuspended in 0.06 M Tris buffer, pH 8.6, and applied on a Whatman DE-52 cellulose anion exchanger column (e.g. K 25/60) with adaptors. The anion exchanger is eluted with a straight ascending gradient of sodium chloride from 0 to 0.15 M NaCl Repeated passages through the Whatman ion exchanger were carried out until optimal purification had been obtained as ascertained by the above methods. The C1 IAC purified in this manner is aggregated to some extent, as ascertained by immunoelectrophoresis, vide FIG. 7.

For use as immunogenic agent in a vaccine which is suitable for the first vaccination of suitable host animals, the C1 IAC-rich fractions from the Whatman ion exchanger were pooled with the fractions from the Sephadex ® G75 Superfine column, and the pooled fractions were dialyzed and thereafter lyophilized as described above. In the following, this combined product is designated "C1 IAC$_{aggregated}$ protein + C1 IAC Sephadex ® G75 Superf.". This product is ready for resuspension for possible admixture with other proteins as described below and/or admixture with C1 IA alone to give a specific antiserum with optimal function.

CHARACTERIZATION OF C1 IAC.

Materials and methods used in the characterization and in other procedures described herein.

Antisera

Rabbit antihuman C1 IA (antibody content 0.7 mg/ml), rabbit antihuman C4 (antibody content 1.0 mg/ml), rabbit antihuman C3 (antibody content 1.2 mg/ml), rabbit antihuman C3 activator (antibody content 0.5 mg/ml), rabbit antihuman $\alpha_2$HS glycoprotein (antibody content 0.35 mg/ml), rabbit antihuman inter-$\alpha$-trypsin inhibitor (antibody content 1.0 mg/ml), rabbit antihuman orosomucoid (antibody content 0.9 mg/ml), rabbit antihuman transferrin (antibody content 2.5 mg/ml), rabbit antihuman albumin (antibody content 1.1 mg/ml), rabbit antihuman prealbumin (antibody content 0.25 mg/ml), rabbit antihuman $\alpha_1$ foetoprotein (0.2 mg/ml), rabbit antihuman plasminogen (antibody content 0.25 mg/ml) were from Behringwerke. Rabbit antihuman IgG (antibody content 0.4 mg/ml), rabbit antihuman IgM (antibody content 0.4 mg/ml), and rabbit antihuman whole serum were from Dakopatts.

Streptokinase

Streptase containing 100,000 units of streptokinase (corresponding) to 30 mg in 10 mg of glutamine and 10 mg hyaluronidase. Dissolved in 400 microliters of 0.15 M saline corresponding to 75 micrograms of streptokinase per ml. Prepared within one hour before use.

Plasma

Obtained freshly from healthy individuals in tubes (14/15 mm) containing 1 ml ACD, and 9 ml blood.

Serum

Human blood was obtained by venipuncture without anticoagulant from healthy donors. Allowed to clot at room temperature for 1 hour and held overnight at 4° C. Serum was separated by centrifugation at 4200 rpm/10 minutes at 4° C.

Bovine Fibrinogen

Achieved from Behringwerke, containing 60 mg lyophilized bovine fibrinogen, freshly prepared at a solution rate of 0.4% for diffusion fibrinolysis and 0.6% for fibrin-agarose electrophoresis.

Neuraminidase

From Vibrio cholerae containing 500 units per ml; was obtained from Behringwerke.

Immunoelectrophoresis

Indubiose A 37 Agarose gel was obtained from L'Industrie Biochemique Francaise.

Buffers

Diemal buffer, pH 8.6, ionic strength 0.02. Barbital saline buffer was composed of 0.025 M barbital and 0.125 M sodium chloride at pH 7.5 (Ratnoff, O. D., Davie, E. W., and Mallet, Studies on the Action of Hageman Factor: Evidence that Activated Hageman Factor in Turn Activates Plasma Thromboplastin Antecedent. J. Clin. Invest. 40:803, 1963). Veronal buffer pH 7.3–7.4, supplied with $MgCl_2$-$6H_2O$, and $CaCl_2$-$2H_2O$.

Human C1

C1 esterase was prepared from the euglobulin fraction by DEAE cellulose chromatography using Lepow buffer containing $Na_3HEDTA$ as described by Bing. The fractions containing crude solutions of C1q, C1r and C1s were pooled and dialyzed against sodium phosphate buffer, pH 7.4, 0.006 M, containing 0.0015 M EDTA, and lyophilized.

N-Acetyl-L-arginine methyl ester hydrochloride (AAME)

Cyclo Chemical Corp., Los Angeles, Calif. AAME was dissolved at a concentration of 0.015 M in phosphate saline buffer, adjusted to pH 7.4 addition of 0.15 M sodium hydroxide.

EA

Sheep blood in an equal volume of Alsevers solution, stored at 4° C., and amboceptor (hemolysin), stored at −° C. were kindly provided from the Serum Institute, Copenhagen, used and standardized spectrophotometrically as described by Mayer (Mayer, MM, Complement and Complement Fixation in Experimental Immunochemistry (E. A. Kabat & M. M. Mayer, Eds.) Springfield, Ill., Charles C. Thomas, 2nd ed. p 133, 1961).

EAC1

This complex between C1q, C1r and C1s together with EA was prepared to form $EAC\bar{1}$. The concentration of $Ca^{++}$ was held at $10^{-3}$ M. The activity of this complex was quantified by measuring the extent of hemolysis produced by an appropriate dilution of human serum containing $16 \times 10^{-3}$ M $Na_2MgEDTA$ to chelate $Ca^{++}$ blocking further action of C1, but permitting reaction of C2, C4, etc.

Experimental procedures

Immunoelectrophoresis

Quantitative electrophoresis in antibody-containing 1% agarose (1.5 mm thick) was run with 2.5 V/cm for 18–20 hours at 20° C. (Laurell C. B., Quantitative Estimation of Proteins by Electrophoresis in Agarose Gel Containing Antibodies. Ann. Biochem. 15:45–52, 1966). Qualitative immunoelectrophoresis was run according to the method of Grabar & Scheidegger. Antigen-antibody crossed electrophoresis was run a.m. Freeman (Clarke, H. C. & Freeman, T. A Quantitative Immunoelectrophoresis Method (Laurell Electrophoresis) pp. 503–509 in Protides of the Biological Fluids. Vol. 14 Elsevier, Amsterdam, 1966., Laurell, C. B. Antigen-antibody Crossed Electrophoresis. Ann. Biochem. 10:358–361, 1965). Initial separation by electrophoresis in agarose with 10 V/cm for 1.5 hours at 20° C. After turning the electric field 90°, electrophoresis was run into antibody-containing agarose gel with 2.5 V/cm for 18 to 20 hours at 20° C.

Immunodiffusion

Was run in 1% agarose a.m. Ouchterlony gel diffusion technique (Ouchterlony, Ö. Progr. Allergy, 6:30, 1962). The diffusion was carried out at room temperature for 3 days.

Tandem-crossed immunoelectrophoresis

Was run a.m. Krøll (Krøll, J. Tandem-crossed Immunoelectrophoresis, in A Manual of Quantitative Immunoelectrophoresis (Eds. Axelsen, NH, Krøll, J., Weeke, B.) Universitetsforlaget, Oslo, 1973, pp. 57–59). The principle is an initial electrophoresis of two antigen samples in the same run separation in agarose gel with 10 V/cm for 1.5 hours. After turning the electric field 90°, electrophoresis is run into antibody containing gel with 2.5 V/cm for 18–20 hours at 20° C.

Fibrin agarose gel electrophoresis

Was run as a modification of fibrin agar electrophoresis (Heimburger, N et al.). Bovine fibrinogen solution, 0.4%, was prepared in 0.9% saline. 9 parts of the 0.4% fibrinogen was added to 2 parts of 0.1 N $Ca(H_2PO_4)_2$·$H_2O$. The fibrinogen solution was rendered completely viscous without content of undiluted fibrinogen by incubation at 37° C. 2 Parts of 1% agarose diluted in diemal buffer were added, and the solution was kept at 45° C. until use. The gel was poured on microslides, coagulated in room temperature and afterwards heated in water bath at 80° C. for 60 minutes. The samples placed in the holes in the fibrin agarose electrophoresis were run for 160 V for 1.5 hours at room temperature. After the run, the reagents listed were added to the grooves. The diffusion was then developed at 37° C. overnight. The fibrin agarose gel was then kept in water bath at room temperature in 0.9% saline, 24 hours, and subsequently washed for 1 hour with distilled water. The slides were stained with Coomasie brilliant blue.

Biological properties of C1 IAC (1) Inhibition of C1 esterase hydrolyzing effect.

C1 esterase was regenerated from crude dialyzed and lyophilized fractions of C1q, C1r and C1s, resuspended at a concentration corresponding to approximately 5 mg/ml. As $Ca^{++}$ source for regeneration was used 0.1 ml 0.033 M $Ca(H_2PO_4)_2$ per ml.

The inhibition of the esterolytic properties of C1 esterase was tested by incubation of 0.5 ml C1 esterase with 0.25 ml C1 IA or C1 IAC (protein concentration 10 mg/ml) or as a control sodium phosphate buffer, ionic strength 0.15, pH 7.45. 0.75 ml of the above-mentioned buffer was added to all tubes. The tubes were incubated at room temperature for 15 minutes.

As a substrate AAME (N-acetyl-L-arginine methyl ester hydrochloride) was used at a volume of 1 ml 0.015 M, added to the tubes, for further incubation for 60 minutes at 37° C.

Immediately after the addition of AAME and 60 minutes later, 1 ml aliquots were removed and mixed with 1 ml of 37% formaldehyde. The titrable acidity in the initial aliquot and in the aliquot incubated for 60 minutes were measured by addition of 0.05 N sodium hydroxide to an end point of pH 7.8. The titrations were performed on a Radiometer pH meter 26 (Radiometer, Copenhagen).

The hydrolysis of AAME was partially inhibited by as little as 0.25 units/ml of C1 IAC, which results are comparable with the inhibition effect of C1 IA reported by several workers in the literature.

(2) Inhibitory effect of C1 IAC on C1 activation of C4 as shown by the inhibition of complement hemolysis.

Figure 8:
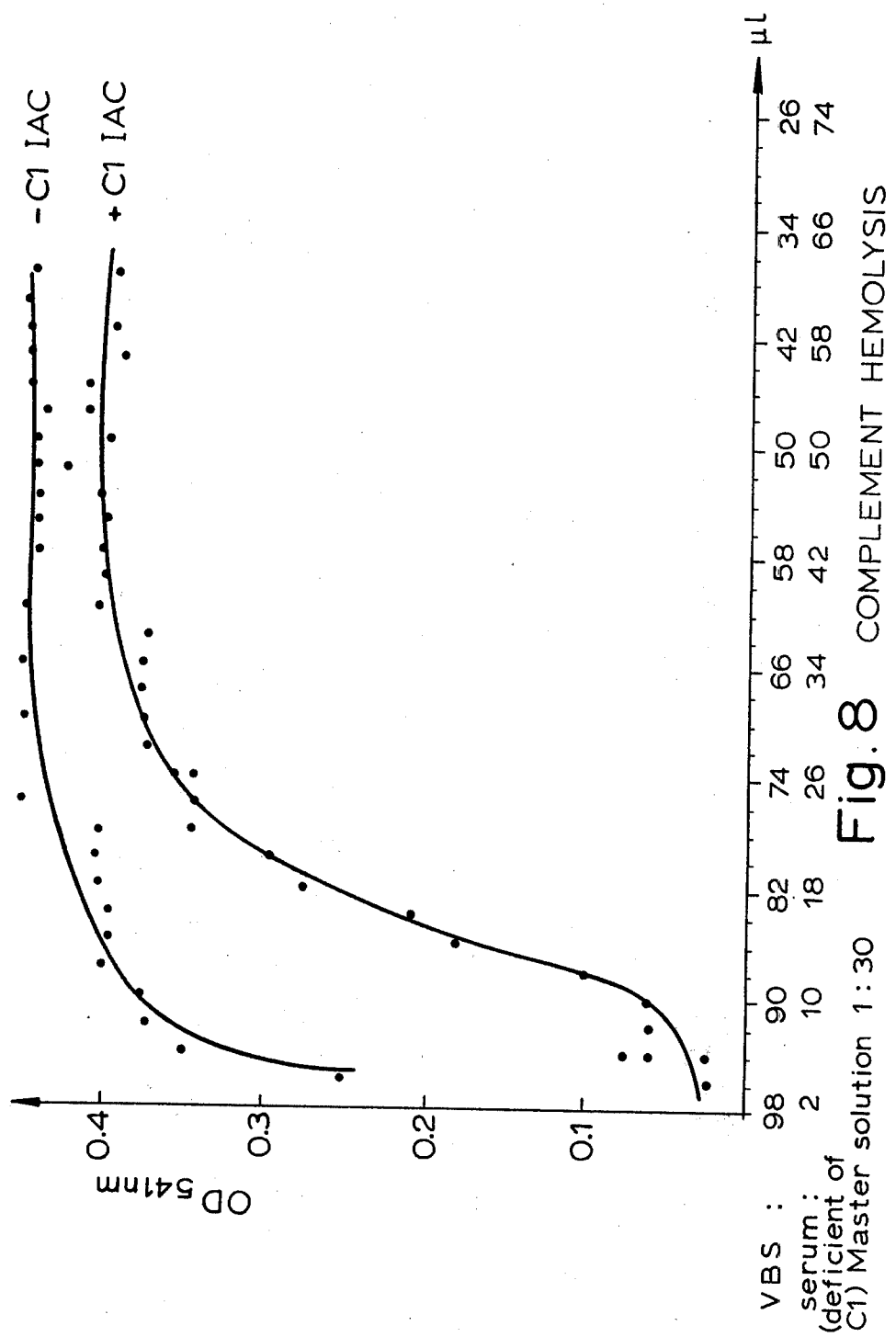
FIG. 8 shows a complement hemolysis graph.

Sheep erythrocytes were coated with amboceptor and purified first component of human complement, following the method used by Ruddy et al. The serum supernatant deficient of C1 was used as complement source C2-C9. Sheep erythrocytes were used at a concentration of 2% in VBS buffer without gelatine. Amboceptor was used at a dilution of 1:400, as estimated by hemolysin titration. The complement titration was performed in serial dilutions in microtiter plates. 100 Microliters of EAC$\overline{1}$ (concentration of C1 was referred to the original volume and serial diluted in the same manner as serum was diluted), 100 microliters of serum deficient of C1 in serial dilutions, and 50 microliters of VBS buffer containing 3 mg C1 IAC or 50 microliters of VBS buffer as a control were mixed and incubated at 37° C. for 30 minutes. Hemolysis was read on a Carl Zeiss PMQ II spectrophotometer, wave length 541 nm, in quartz microcuvettes. C4, C3 and C1 IAC from the serial dilutions were checked by rocket immunoelectrophoresis. As seen on FIG. 8, the solutions containing C1 IAC show inhibition of hemolysis compared to the solutions without any content of C1 IAC.

(3) The lack of effect of C1 IA and C1 IAC upon the clotting time of plasma.

The effect of purified C1 IA and C1 IAC upon the blood clotting time was tested by a modification of a technique described by Ratnoff et al. (Ratnoff, O. D., Copoly, J. E. & Pritchard, J. A. The blood Clotting Mechanism during Normal Parturition. J. Lab. Clin. Med. 44:408, 1954).

C1 IA and C1 IAC, together with a buffer control (0.005 M phosphate buffer), at a concentration of 10 mg per ml were mixed with 1 ml citrated plasma containing 0.025 M calcium phosphate in polystyrene tubes. 200 Microliters of C1 IA, C1 IAC, or buffer control were simultaneously added to the tubes.

The mixtures were incubated at 37° C. in water bath The interval elapsing from the incubation until clotting occurred was recorded as the clotting time.

C1 IA and C1 IAC, at a concentration of 1 mg/ml, had no effect upon the recalcified clotting time of platelet-deficient plasma, as measured in polystyrene tubes (Table I).

Table I (The effect of C1 IA and C1 IAC upon blood clotting).

| Plasma regenerated with Ca$^{++}$ | C1 inactivator (number) | | Clotting time minutes + seconds | |
|---|---|---|---|---|
| Donor No. 16697 | C1 IAC$_{pleura}$ | (4010) | 4 | 0 |
| " | Buffer | | 4 | 15 |
| " | C1 IAC$_{pleura}$ | (4011) | 4 | 15 |
| " | Buffer | | 4 | 15 |
| " | C1 IAC$_{ascites}$ | (4014) | 4 | 0 |
| " | Bufer | | 3 | 45 |
| " | C1 IAC$_{ascites}$ | (4015) | 3 | 45 |
| " | Buffer | | 3 | 45 |
| " | C1 IA (donor) | (4021) | 3 | 45 |
| " | Buffer | | 3 | 45 |
| " | C1 IAC$_{MEM}$ | (4023) | 3 | 45 |
| " | Buffer | | 3 | 30 |
| " | C1 IAC$_{RPMI}$ | (4025) | 3 | 30 |
| " | Buffer | | 3 | 15 |
| " | C1 IAC$_{MEM}$ | (4026) | 4 | 0 |

Table I-continued (The effect of C1 IA and C1 IAC upon blood clotting).

| Plasma regenerated with Ca$^{++}$ | C1 inactivator (number) | Clotting time minutes + seconds | |
|---|---|---|---|
| " | Buffer | 3 | 45 |

The regeneration system was 0.5 ml plasma with 0.025 M Ca(H$_2$PO$_4$)$_2$.
The buffer was 0.005 M phosphate buffer, pH 7.4.
The concentration of the C1 IAC and C1 IA are held approximately constant, based on the concentration found by rocket immunoelectrophoresis and dry weight of the purified protein.

Thus, the clotting time for both C1 IAC added and C1 IA added plasma as well as plasma with a content of C1 IA of about 30 mg/100 ml varied 60 seconds with no significant difference for the C1 IAC or C1 IA admixed plasma and non-admixed plasma. The mean clotting time in this system is in accordance with the mean clotting time found by Ratnoff et al., loc. cit.

(4) The inhibitory effect of C1 IAC on fibrinolysis.

The inhibiting effect of C1 IAC was studied on a regeneration system consisting of plasma recalcified with calcium phosphate.

The clots were weighed before induction of lysis by streptokinase (streptase, 20 micrograms), 100,000 units per ml. The weight of the individual clots after an incubation period of 6 hours (tubes sealed) at 37° C. was recorded and compared to the original weight of the individual clots before induction. Before induction of lysis, C1 IAC or C1 IA at a concentration of 10 mg/ml or buffer control was added to the clotted plasma. The results appear from Table II below.

Table II (Clot lysis inventigation).

| Plasma regenerated by Ca$^{++}$ | C1 IAC or C1 IA No./Buffer | Weight of clot before lysis | Induction of lysis by Streptase | Weight of clot after 6 hours' lysis |
|---|---|---|---|---|
| Donor No. 16697 | 4011 | 0.368 g | 20 micrograms | 0.039 g |
| " | Buffer | 0.371 g | " | 0.026 g |
| " | 4014 | 0.365 g | " | 0.047 g |
| " | Buffer | 0.363 g | " | 0.033 g |
| " | 4015 | 0.361 g | " | 0.047 g |
| " | Buffer | 0.367 g | " | 0.025 g |
| " | 4021 (C1 IA) | 0.367 g | " | 0.038 g |
| " | Buffer | 0.365 g | " | 0.025 g |
| " | 4023 | 0.360 g | " | 0.030 g |
| " | Buffer | 0.361 g | " | 0.029 g |
| " | 4025 | 0.364 g | " | 0.044 g |
| " | Buffer | 0.365 g | " | 0.036 g |
| " | 4026 | 0.363 g | " | 0.043 g |
| " | Buffer | 0.361 g | " | 0.034 g |

The regeneration system consisted of plasma and Ca(H$_2$PO$_4$)$_2$. The lysis induced with streptase consisting of 100,000 units of strep tokinase per ml. The concentration of C1 IAC or C1 IA was held approximately constant based on rocket immunoelectrophoresis and dry weight of the purified protein.

It is seen from Table II that the lysis of the clots is to some extent inhibited by C1 IAC.

(5) Inhibiting effect of C1 IAC against the plasma fibrinolytic system as demonstrated by fibrin agarose electrophoresis.

The procedure is described in detail above. The materials placed in the holes and added to the grooves appear from Table III below.

Table III (Combination of fibrin agarose electrophoresis performed).

| Punched holes | Grooves |
|---|---|
| Human serum, undiluted | Streptokinase 10,000 units per ml |
| Human serum, undiluted | Streptokinase 10,000 units per ml + C1 IAC, concentration 1 mg/ml |
| Streptokinase-activated plasma 40 units/ml | Anti plasminogen |

Table III-continued
(Combination of fibrin agarose electrophoresis performed).

| | |
|---|---|
| Streptokinase-activated plasma 40 units/ml | Cl IAC at a concentration of 1 mg/ml |
| Human serum, undiluted | Streptokinase-activated plasma, 40 units/ml |
| Human serum, undiluted, containing Cl IAC at a concentration of 1 mg/ml | Streptokinase activated plasma, 40 units/ml |

Assays of the residual mixtures of C1 IAC and streptokinase-activated human plasmin revealed that C1 IAC at a final concentration of 1 mg/ml inhibited the plasmin activity. A clear zone formed in the fibrin net demonstrates the fibrinolysis. It was found that the clear zone representing the serum mixed with C1 IAC is smaller than the clear zone representing the control serum with buffer.

Assays of electrophoresis in fibrin agarose gel of streptokinase-activated plasma with anti-plasminogen in one groove and C1 IAC in the other groove revealed an inhibited zone of fibrin consumption in the zone corresponding to the plasminogen precipitate and to the groove containing C1 IAC.

Fibrin agarose gel of human serum admixed with C1 IAC at a concentration of 1 mg/ml, run for electrophoresis and immediately after activated by Streptokinase in the grooves, showed no consumption in the fibrin agar, while a consumption on the electrophoresis of serum without content of C1 IAC was seen.

(6) The influence of pH on C1 IAC's inhibition of C1 esterase hydrolyzing effect.

The influence of pH on the biological activity of C1 IAC was examined in the pH range of 3–11. Purified C1 IAC was diluted to a concentration of approximately 30 mg%. 2.0 ml aliquots of the C1 IAC solution was tested by titration to the desired pH with 0.15 N HCl or 0.15 M NaOH. The mixtures were kept at 4° C. for 18 hours and then titrated to pH 7.4 ± 0.1. The volume of each mixture was made up to 3.0 ml with 0.15 M NaCl and finally to 4.0 ml with 1.0 ml sodium phosphate, pH 4.7, ionic strength 0.15. Aliquots of 0.25 and 0.5 ml were taken from each mixture for C1 IAC inhibitor assay. The method used in the inhibition assay was blocking of C1 esterase effect upon AAME.

The activity of C1 IAC progressively diminished below pH 5.5 and above pH 10.5.

(7) The influence of heat on C1 IAC's inhibition of C1 esterase hydrolyzing effect.

Heat stability of C1 IAC was tested by incubation of purified C1 IAC in 0.15 M NaCl kept at a pH of 7.1 for 30 minutes at various temperatures from 0° C. to 60° C. The biological activity was assayed by C1 IAC inhibiting effect on C1 esterase hydrolyzing effect on AAME. 0.5 ml aliquots were used. It was found that the acitvity of C1 IAC diminished drastically when incubated at temperatures exceeding 56° C.

Immunological properties of C1 IAC (8) Grabar-Scheidegger immunoelectrophoresis.

Figure 9:
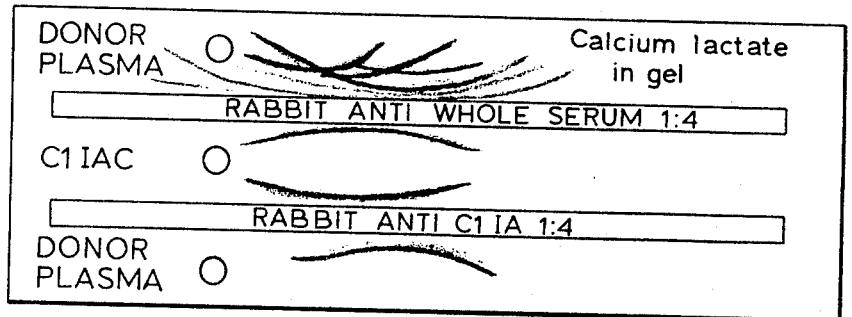
FIGS. 9-14 show various immunoelectrophoretic tests.

In Grabar-Scheidegger immunoelectrophoresis against rabbit antihuman C1 IA, a gull wing precipitate results from C1 IA, whereas C1 IAC does not show gull wing precipitation. (FIG. 9). (The "gull wing" is described by Hirschfeld (1960)). The C1 IAC precipitate extends into the β zone when immunoelectrophoresis is run in the presence of calcium lactate, vide FIG. 9.

(9) Laurell rocket immunoelectrophoresis.

Figure 7:
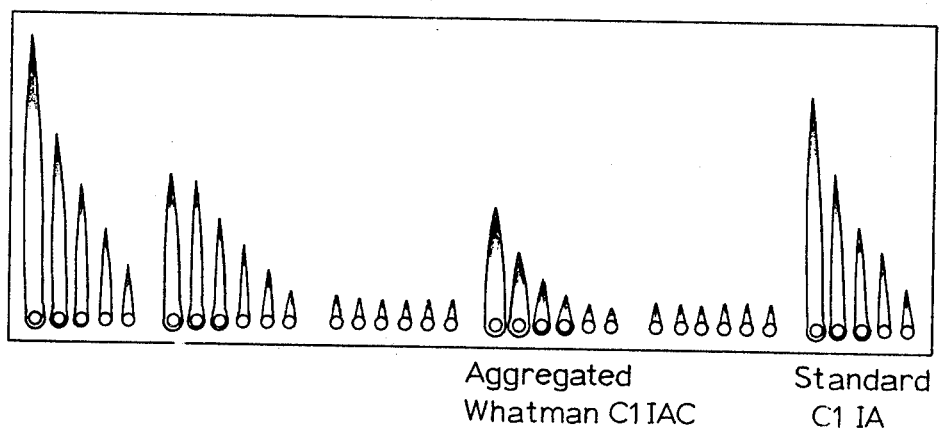
FIG. 7 shows an immunoelectrophoretic purification.

In Laurell rocket immunoelectrophoresis against rabbit antihuman C1 IA, a slight difference between C1 IA and C1 IAC is found in the configuration of the rockets, which are somewhat more blunt for C1 IAC than for C1 IA, approximately as seen in FIG. 7.

(10) Tandem-crossed immunoelectrophoresis a.m. Krøll.

Figure 11:
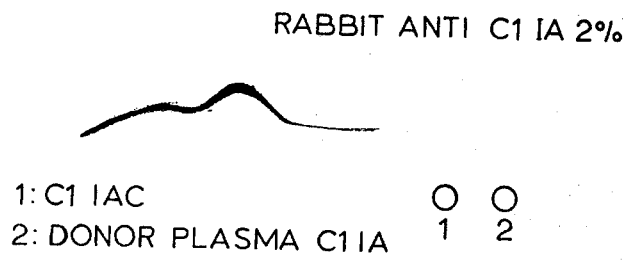
Figure 12:
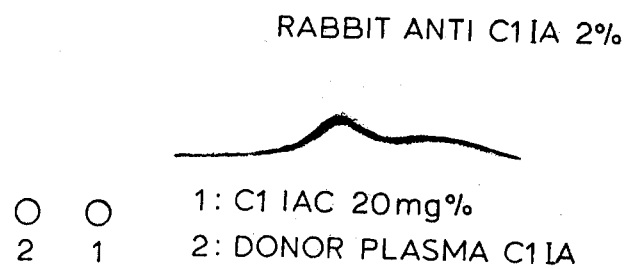

Using rabbit antihuman C1 IA, full identity was found between C1 IA and C1 IAC in tandem-crossed immunoelectrophoresis, as indicated in FIGS. 11 and 12.

(11) Crossed Freeman immunoelectrophoresis.

Figure 14:
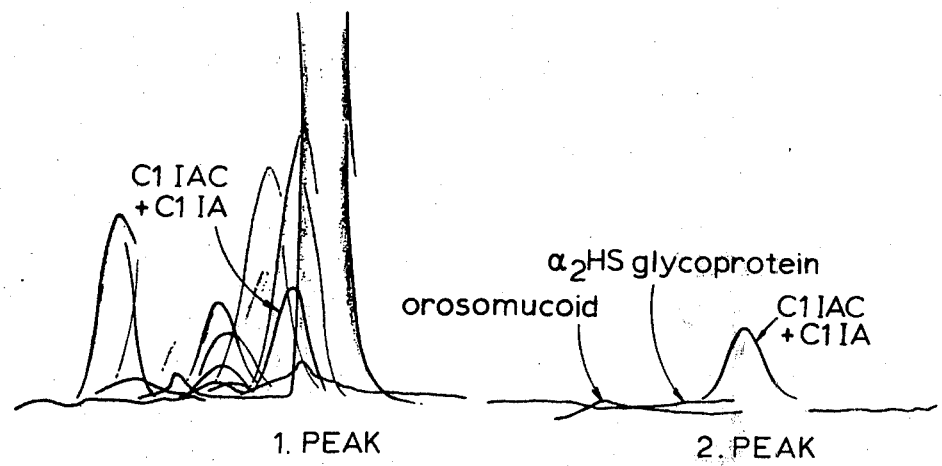

Using rabbit antihuman whole protein serum, purified C1 IA and purified C1 IAC give identical precipitates in crossed Freeman immunoelectrophoresis (having an appearance similar to the one seen in FIG. 14, 2nd peak).

(12) Neuraminidase effect on the immunological properties of C1 IAC.

One ml of purified C1 IAC at a concentration of approximately 1.0 mg/ml was incubated with 0.2 ml of vibrio cholerae neuraminidase (V.C.N.) corresponding to 100 units of neuraminidase (one neuraminidase unit is the amount of enzyme sufficient to release 1 ng N-acetyl-neuraminic acid from human α-glycoprotein).

The mixture was stirred and incubated at 37° C. for 15 minutes. The controls contained 0.2 ml 0.09 M phosphate buffer.

Figure 13:
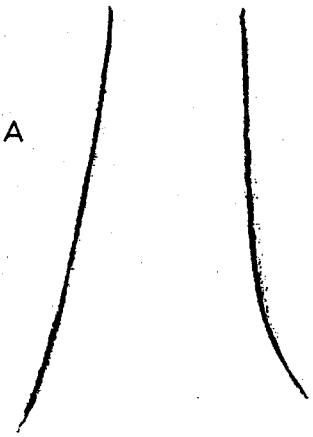

The purified C1 IAC thus treated was subjected to tandem-crossed immunoelectrophoresis against rabbit antihuman C1 IA, vide FIG. 13 which shows only one curve which is from the C1 IAC; the neuraminidase-treated C1 IAC is not able to form precipitate. (The curve is very tall due to excess concentration of the rabbit antihuman C1 IA in relation to the C1 IAC in this particular experiment).

Figure 10:
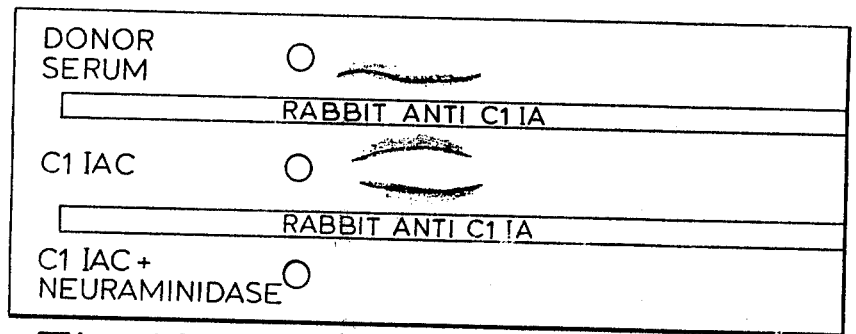

On Grabar-Scheidegger immunoelectrophoresis against rabbit antihuman C1, IA, vide FIG. 10, it was shown that C1 IAC treated with neuraminidase as described above, gives no precipitate.

(13) Ouchterlony immunodiffusion against oligospecific antiserum.

In Ouchterlony immunodiffusion against antiserum produced on pigs of "Dansk Landrace" or "Yorkshire race" mixed with "Dansk Landrace" or on sheep of Texel type ("Jysk Hederace") or mixed breeds involving Shropshire and Oxford Down, which host animals have been vaccinated with vaccines containing C1 IAC and C1 IA, e.g. the type 1 or 2 vaccine described in the section "Vaccination of Host Animals", or against antiserum from any other animal which is able to distinguish between C1 IAC and C1 IA and which has been vaccinated with vaccines containing C1 IAC and C1 IA in effective immunogenic amounts, C1 IAC gives a precipitate distinguishable from the C1 IA precipitation. For example, serum from cancer patients will give two precipitates distinguishable from each other, whereas serum from healthy donors (or patients with non-malignant diseases) will give only one precipitate, this being the C1 IA precipitate. One of the precipitates from cancer patient serum will correspond to the C1 IA precipitate from the cancer patient serum. An immunodiffusion of this type is shown in FIG. 3. In the two central holes, oligospecific antiserum was applied, and in the circumferential holes, serum from healthy donors ("DONOR") and various patients were applied. Serum from each sample was applied in each of two opposite holes. In the present case, the antiserum used was one obtained from a sheep vaccinated with a type 1 vaccine (vide the section "Vaccination of Host Animals").

From FIG. 3, it will be seen that a strong interior precipitate was formed which was identical for donor and for all the patients. This is the precipitate of C1 IA. However, patient 3 (verified cancer) serum gave an extra precipitate easily distinguishable from the C1 IA precipitate. This is the C1 IAC precipitate. Also, all serum samples gave a common weaker exterior precipitate, this being the orosomucoid precipitate.

It is evident that the precipitate formed by C1 IAC is easily distinguishable from the C1 IA precipitate. While the immunodiffusion shown in FIG. 3 were actually experiments made for diagnostic purposes, analogous precipitation patterns have, of course, been demonstrated with mixtures of pure C1 IA and C1 IAC, and it will be understood that the Ouchterlony technique is only one example of the immunological identification or assay methods (Laurell, Mancini, etc. etc.) which give distinction between C1 IA and C1 IAC when oligospecific antiserum is used.

Other properties of C1 IAC.

(14) Estimation of the molecular weight of C1 IAC by the gel filtration technique.

A Sephadex ® G200 gel filtration column (Pharmacia K 25/50) was equilibrated with Tris buffer, pH 8.6. A solution of C1 IAC Sephadex ® G75 Superf., purified human albumin (chromatographed and checked for purity by immunoelectrophoresis), hemoglobin (prepared by hemolysis of erythrocytes and purified, checked for purity), and purified IgG (molecular weight 130,000–150,000) was applied on the column, and the effluent was monitored spectrophotometrically, the identity of the peaks being ascertained by immunoelectrophoresis. The first peak consisted of IgG, and before it had fully decreased, the second peak (C1 IAC) began to appear. When the C1 IAC peak had passed, a number of substantially empty fractions were noted, whereafter the next peak appeared which was the albumin. Almost immediately after the albumin peak, the hemoglobin peak appeared.

Based upon the spectrophotometrical graph, it is evident that the molecular weight of C1 IAC must be greater than the molecular weight of the albumin which is 60,000, and just below the molecular weight of the IgG. As the molecular weight of IgG cannot be stated more accurately than 130,000–150,000, a similar uncertainty applies to the estimation of the C1 IAC molecular weight which, based on the position of the C1 IAC peak, is 110,000–130,000.

(15) Sedimentation constant of C1 IAC determined by ultracentrifugal sedimentation-velocity.

Experimental conditions

Ultracentrifuge:
  MSE analytical ultracentrifuge Mk2,
  Optics: Schlieren.
Ultracentrifuge cell:
  10 mm double sector synthetic boundary over-filling cell.
Sample:
  C1 IAC pure, harvested from human mammacarcinoma cell culture in RPMI medium.
Rotational speed:
  1st Experiment: 60,000 rpm.
  2nd Experiment: 60,010 rpm.
Temperature:
  1st Experiment: 19.7° C.
  2nd Experiment: 20.2° C.
Analysis solution:
  1st Experiment: in 0.02 M $KH_2PO_4$, 0.1 M NaCl, pH 7.00.
  2nd Experiment: in 0.02 M $KH_2PO_4$, 0.1 M NaCl, pH 7.00.

Results:

1st Experiment (c = 0.55%)

| Photo No. | Time after holding speed | $(s_c)_{app} = \frac{1}{\omega^2} \frac{\Delta \ln r}{\Delta t}$ |
|---|---|---|
| 4 | 10 sec. | 5.29 S |
| 5 | 210 sec. | 4.94 S |
| 6 | 410 sec. | 4.82 S |
| 7 | 610 sec. | 4.98 S |
| 8 | 810 sec. | 4.57 S |

The results of 1st Experiment are shown in Graph 1, FIG. 15.

By extrapolation (linear regression through the points) to the meniscus ($r_{T_o}$) is found (vide Graph 1): $s_c = s_{19.7,sol.}^c = 5.28$ S.

2nd Experiment (c = 0.94%)

| Photo No. | Time after holding speed | $(s_c)_{app} = \frac{1}{\omega^2} \frac{\Delta \ln r}{\Delta r}$ |
|---|---|---|
| 7 | 0 sec. | 5.00 S |
| 8 | 201 sec. | 4.71 S |
| 9 | 402 sec. | 5.06 S |
| 10 | 603 sec. | 5.06 S |
| 11 | 804 sec. | 5.01 S |
| 12 | 1005 sec. | 4.86 S |

The results of 2nd Experiment are shown in Graph 2, FIG. 15.

By extrapolation (linear regression through the points) to the meniscus ($r_{T_o}$) is found (vide Graph 2): $s_c = s_{20.2,sol.}^c = 4.97$ S.

Conversion to standard conditions:

1st Experiment (c = 0.55%)

$$s_{20,sol.}^c \approx s_{19.7,sol.}^c \times \frac{\eta\ 19.7,sol.}{\eta\ 20,sol.} \approx 5.28 \times 1.01\ S$$

$$s_{20,w}^c \approx s_{20,sol.}^c \times \frac{\eta\ 20,sol.}{\eta\ 20,w} \approx 5.28 \times 1.01 \times 1.03 = 5.49\ S$$

2nd Experiment (c = 0.94%)

$$s_{20,sol.}^c \approx s_{20.2,sol.}^c \times \frac{\eta\ 20.2,sol.}{\eta\ 20,sol.} \approx 4.97 \times 0.995\ S$$

$$s_{20,w}^c \approx s_{20,sol.}^c \times \frac{\eta\ 20,sol.}{\eta\ 20,w} \approx 4.97 \times 0.995 \times 1.03 = 5.09\ S$$

It is to be noted that in the conversion to standard conditions, no regard has been paid to correction of specific gravity, nor to correction of the partial specific volume of C1 IAC. The correction factor deriving from these is probably very close to 1.

Extrapolation to c = 0. Vide Graph 3, FIG. 15. From Graph 3, is found $S^o_{20,w} = 6.2$ S.

FIGS. 16 and 17 show photos Nos. 4, 6, and 8 from 1st Experiment, and 7, 9, and 11 from 2nd Experiment. Furthermore, FIG. 18 shows photos at t < 0 sec. (taken during acceleration at 30,000 rpm) and at t = 1206 and 1608 seconds, respectively.

DEMONSTRATION OF THE CANCER ASSOCIATION OF C1 IAC.

Materials and methods used in these experiments were as described above.

Pleural or ascites exsudates from patients suffering from far advanced carcinomas were used as sources for carcinoma cell culturing. Contaminated fluids were excluded. The cell cultures grown in Roux flasks and in Falcon plast flasks were distributed in clonal growth or more diffuse growing. The morphology of the clones showed cell and nuclei polymorphy, one big or several nucleoli, more cells had several nuclei. Many mitosis were seen. Of these mitosis several were atypical. The attachment of the cells to plast and glass were sufficient.

27 Of the 37 human carcinoma cultures were subcultured from 1 to 4 times. A mean of 1.8 subcultures of 27 cultures. The cell ines were accordingly cultured and used for production of C1 IAC for a period ranging from 2 to 5 months. 10 Carcinoma cell cultures were not subcultured, and consequently used for production of C1 IAC for about 2 months.

The cell-free C1 IAC was harvested about once a week, alternatingly released into MEM medium containing 15% inactivated foetal calf serum and into RPMI amino acid medium. Consequently, it was possible to harvest 4 times a month from the same cell culture. In a total, 235 isolations of C1 IAC were performed. Of these isolations, 37 were performed directly from the cell-free pleural and ascites fluids.

101 Isolations were performed from MEM medium containing 15% inactivated foetal calf serum and 97 isolations were performed from RPMI medium. On each carcinoma cell culture, C1 IAC was isolated ranging from 2 to 14 times. A mean of 5.4 isolations per cell culture. During the growth period in RPMI medium, the cell growth was depressed, while during the period in MEM medium containing inactivated foetal calf serum the cells regained their normal growth cycle in vitro. In several cell cultures it was necessary to let the cell culture develop more sufficiently before changing to RPMI medium again. The amount of cells in a culture was optimally held at about $2 \times 10^5$ cells per Roux flask. The cell cultures were constantly checked for development of the individual cell types. The cell types from pleura and ascites consisted of carcinoma cells, fibroblasts and mesothelial cells. In flasks with clonal growth of the carcinoma cells it was not difficult to establish the approximate quantity of these cells. But in rather diffusely growing cell cultures it was more difficult to establish the approximate quantity of carcinoma cells. The amount of cells producing C1 IAC was related to the amount of cells coated with C1 IAC as found by cytophotometry, from idem cell culture lines.

A total of 37 patients were used as donors. The age of the patients ranged from 33 to 80 years. The patient group consisted of 34 females and 3 males. The 37 patients were attending hospital for removal of pleural and ascites fluids. All patients had far advanced carcinomas of various origin. All patients had previously during their disease been treated with radiation from 1 to 3 series. All patients had been treated with cytostatics and cortisone or prednisone. 25 of the patients were during the donor period treated with corisone or prednisone.

Human control cell cultures.

Pleural and ascites transudates from patients, suffering from non-neoplastic diseases served as non-malignant cell source. This form of cell source for in vitro culturing proved to be a sufficient source. The attachment to Falcon flasks was sufficient, but more difficult to glass flasks of Roux type. The out-growth proved to need a longer period to get a sufficient amount of cells for protein production, comparable with malignant cell culture. No clonal growth was obtained, but all cell cultures developed diffusely.

The cells found attached to the flasks, were fibroblasts and mesothelial cells. Totally 28 control isolations of protein for detection of C1 IA resembling or C1 IAC resembling protein were performed. As for the carcinoma cell cultures, the cell-free protein was harvested about once a week, alternatingly released into MEM medium containing 15% inactivated foetal calf serum and into RPMI amino acid medium. Control cell cultures were furthermore checked with immunofluorescence and cytophotometry for presence of C1 inactivator coat as shown later.

Immunofluorescence cytophotometry.

The cytophotometric measurements were carried out on 36 primary cell cultures from carcinoma patients and from 10 control cell cultures of non-malignant cell lines. A total of 25 subcultures from carcinoma lines were used for cytophotometric measurements in order to establish the C1 IAC coat on the subcultured carcinoma cell lines. The C1 IAC coat is membrane associated as demonstrated by photos of the cells exhibiting positive immunofluorescence.

Figure 19:
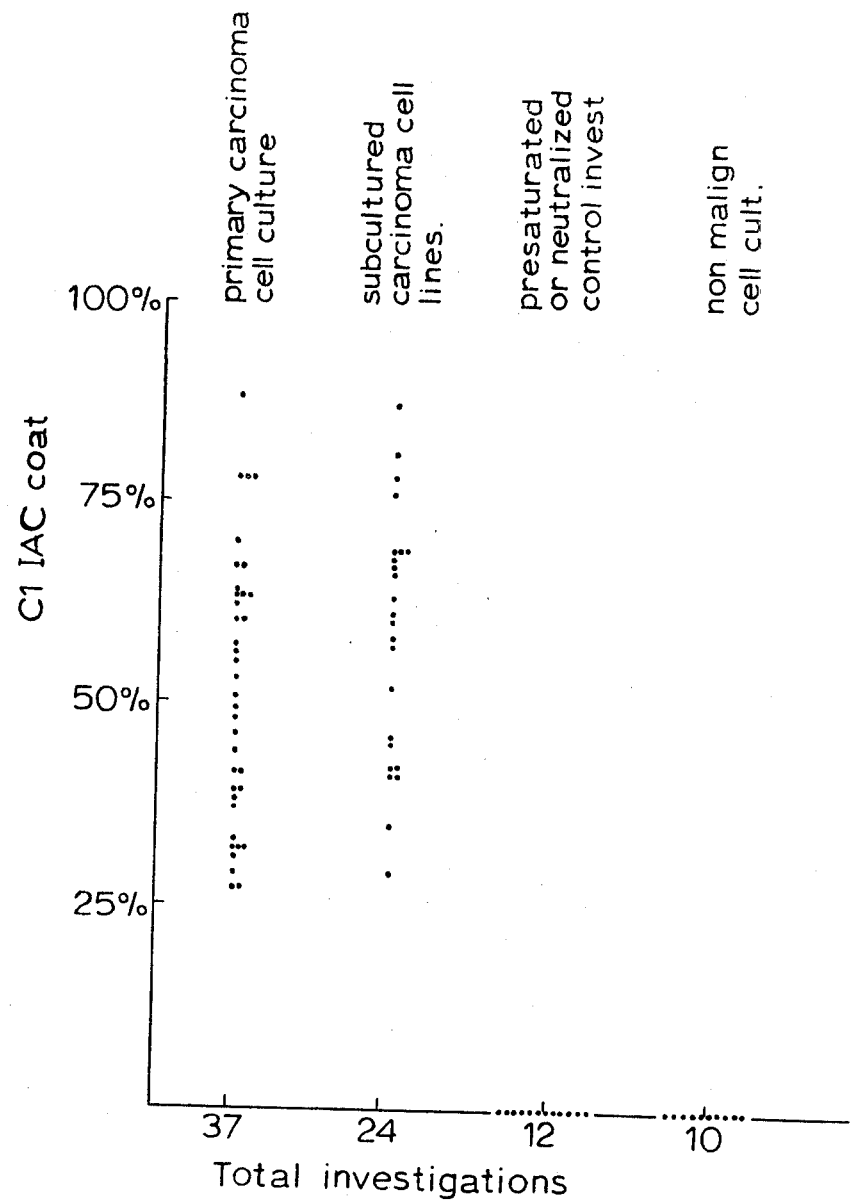
FIG. 19 shows distributions of immunofluorescence measurements.

Of the carcinoma primary cell lines, an average of 51.3% of the cells showed specific immunofluorescence with anti C1 IA-FITC as measured by cytophotometry. The average distributions of the immunofluorescence measurements of carcinoma cell cultures is demonstrated in FIG. 19. Values scored below 40 w.u. are defined as non-specific signals.

An average of 58.4% of the cells from the subcultured cell lines show specific immunofluorescence. When comparing the primarily cultured carcinoma cells with the corresponding subcultured cell lines, the amount of cells exhibiting C1 IAC coat varies significantly.

In some of the subcultured cell lines the amount of C1 IAC coat cells is higher, when compared with their origin culture.

Control specific immunofluorescence as performed with presaturation of the cell culture with non-labelled anti C1 IA, followed by incubation with anti C1 IA-FITC and neutralized anti C1 IA-FITC (with purified C1 IA), did not show values exceeding the border line and thus, not a single cell was found showing specific immunofluorescence. The control cell cultures (non-malignant cells) measured by cytophotometry did not show any C1 inactivator coat. The measured values of the cells scored, were all under 40 w.u. The values of the control cell cultures are distributed roughly as the values for control of immunofluorescence specificity. The control cell cultures showed a reliability for at least 63% and the malignant cell cultures a reliability for at least 90%. The significant difference is less than 0.002 (Fischer's exact test).

Control MEM mediae containing 15% inactivated foetal calf serum and control RPMI mediae (not used for cell culturing) were subjected to immunoelectrophoresis before and after a Dowex elution. The investigated mediae did not reveal any precipitation lines against antihuman C1 IA antiserum from rabbit. The only precipitation lines detected were found against antihuman albumin antiserum from rabbit. These control experiments gave accordingly evidence to the fact that the mediae used for cell culturing did not contain any proteins reacting with anti C1 IA before being used for cell culturing.

MEM mediae and RPMI mediae harvested from non-malignant cell lines, subjected to immunoelectrophoresis did not reveal any precipitation lines against antihuman C1 IA antiserum from rabbit. Using Ouchterlony immunodiffusion no precipitation lines were detected against antihuman C1 IA antiserum from rabbit.

Accordingly, no detectable C1 IA was released from control non-malignant cell cultures into the mediae, when jusing immunoelectrophoretic and immunodiffusion methods for detection.

PURIFICATION OF C1 IAC/C1 IA FROM PLEURAL/ASCITES FLUID FROM CANCER PATIENTS.

Pleural/ascites fluid from patients suffering from cancer with metastases to pleura and/or ascites is centrifuged as described in the above section "Preparation of C1 IAC", and the precipitate is explanted to cancer cell cultures as described above. The supernatant, possibly after storage at $-20°$ C. (vide above), is allowed to clot spontaneously for 2 hours at room temperature, and thereafter is allowed to stand overnight in refrigerator for complete spontaneous clotting. The supernatant is again centrifuged to remove fibrine and frozen at $-20°$ C. until the further purification takes place.

2 ml of the pleural/ascites fluid thus treated are admixed with 2.5 g of DEAE Sephadex ® A50 anion exchanger which had been preheated to 100° C. for 30 minutes and thereafter cooled to room temperature. The mixture is stirred at 8° C. for one hour. Thereafter, the mixture is placed in a column and washed with 5 × 40 ml 0.15 M NaCl with suction from the column bottom. The C1 IAC/C1 IA protein material is absorbed in the ion exchanger. The ion exchanger material in the column is washed with 200 ml NaCl, 2 M, and trisodium citrate, 0.01 M, pH 7.0.

The latter eluate containing C1 IAC/C1 IA was admixed with saturated $(NH_4)_2SO_4$ (pH adjusted to 7.0 with NaOH) until 50% saturation at 8° C. in the course of one hour. Thereafter, centrifugation (10 minutes at 3000 rpm at room temperature) was performed, and to the supernatant, $(NH_4)_2SO_4$ (as above, pH 7.0) was added until 65% saturation at 8° C. in the course of one hour. Again, centrifugation (10 minutes at 3000 rpm at room temperature) was performed, and the precipitate containing C1 IAC/C1 IA was dialyzed overnight against distilled water at 4–6° C. and thereafter redissolved in 0.15 M NaCl.

The solution was lyophilized, either by shell lyophilizing or by lyophilizing in vacuum with external heating as described in the section termed "Preparation of C1 IAC".

The product, in the following designated "C1 IAC/C1 IA DEAE Sephadex A50", is ready for use in vaccines, either in admixture with the above-described C1 IAC/C1 IA, $a_2HS$, Zn $a_3$, orosom., or alone.

PURIFICATION OF C1 IA/ C1 IAC WITH A CONTENT OF OROSOMUCOID, $a_2HS$ GLYCOPROTEIN AND Zn $a_2$ GLYCOPROTEIN FROM PLEURAL/ASCITES FLUID.

Pleural/ascites fluid from patients suffering from cancer with metastases to pleura and/or ascites is centrifuged as described in the above section "Preparation of C1 IAC", and the precipitate is explanted to cancer cell cultures as described above. The supernatant, possibly after storage at $-20°$ C. (vide above), is allowed to clot for two hours at room temperature. The clot is removed, and the fluid is recentrifugated at 1200 rpm at room temperature for 10 minutes. Thereafter, the fluid is salted out to precipitate contaminating proteins, suitably to 40% saturation with saturated $NH_4SO_4$ at 0° C. with agitation. Thereafter, working up is performed in the same manner and under the same conditions as the working up after salting out in the above section "Preparation of C1 IAC", subsection "Isolation of C1 IAC", using the Whatman DE-52 cellulose anion exchanger column for the final purification.

An example of a Freeman crossed immunoelectrophoresis against antihuman whole protein serum is shown in FIG. 14, wherein "1. Peak" was made before treatment of pleural fluid, while "2. Peak" was made on a C1 IA + C1 IAC-rich fraction from the Dowex run. From the "1. Peak" immunoelectrophoresis, it will be seen that the peak representing C1 IAC + C1 IA is relatively high compared to most other proteins (the very tall peak is albumin), indicative of the malignant state. In the "2. Peak" part, peaks for orosomucoid and $a_2HS$ glycoprotein, although low, may also be detected (the identity of the protein in each peak was ascertained through parallel crossed immunoelectrophoreses against specific antisera).

Figure 20:
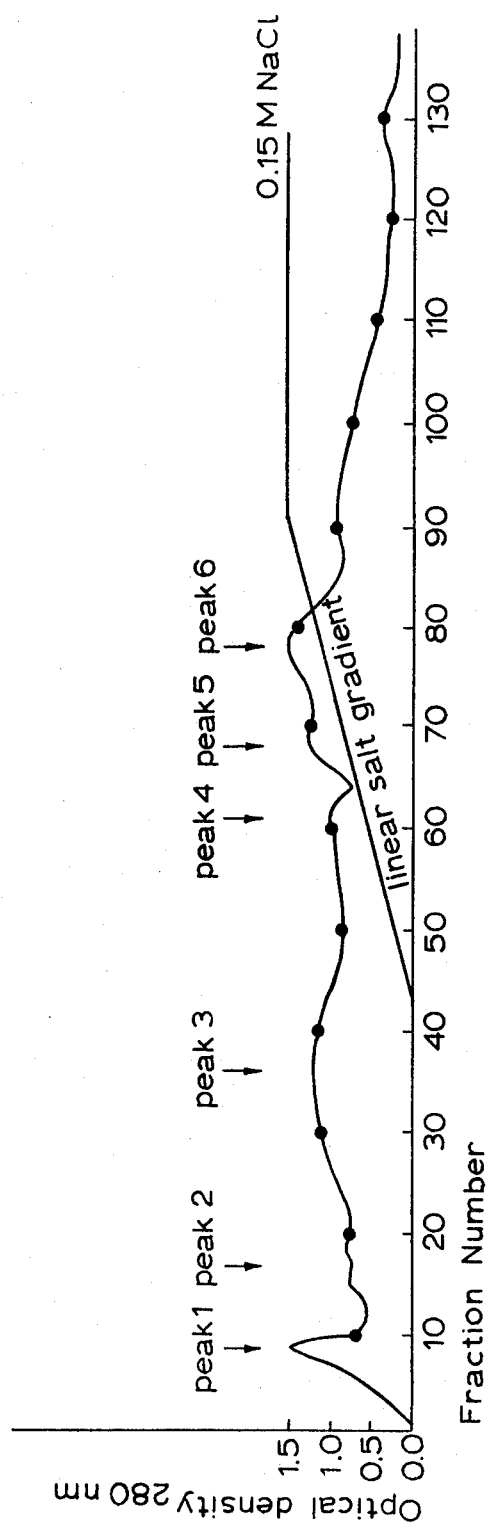
FIG. 20 shows an elution graph.

An example of a first Whatman DE-52 elution graph is shown in FIG. 20. The column was a Pharmacia K 26/70 with a bed volume of 2.6 × 70 cm with flow adaptor. The C1 IAC + C1 IA peak is peak 6.

Figure 21:
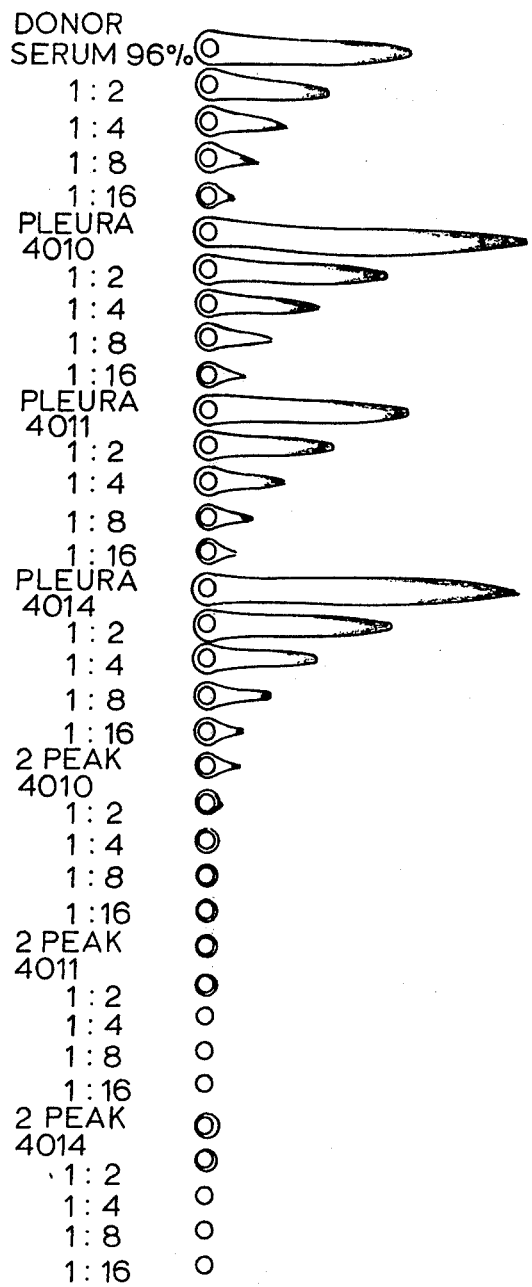
FIG. 21 shows immunoelectrophoresis against anti orosomucoid.

The fractions rich in C1 IA/C1 IAC and the three other proteins mentioned above (as ascertained by rocket and Grabar-Scheidegger immunoelectrophoresis using commercially available antisera against $a_2HS$ glycoprotein, Zn $a_2$ glycoprotein, and orosomucoid, and rabbit antihuman C1 IA (an example of rocket immunoelectrophoresis against anti orosomucoid is shown in FIG. 21)) are pooled, dialyzed and lyopholized as described in the above-mentioned section. In the following, the resulting product is designated "C1 IAC/C1 IA, $a_2HS$, Zn $a_2$ orosom.". This product is suitable for use as an immunogenic agent in a vaccine which is suitable for booster vaccinations (2nd and 3rd vaccinations of host animals), preferably in admixture with other proteins here described.

VACCINATION OF HOST ANIMALS.

Various animals may be selected for vacination with vaccines containing the above-described process as immunogenic agent for the production of antisera. It has been found that pigs of "Dansk Landrace" or mixture of Yorkshire race and Dansk Landrace and sheep of "Jysk Hederace" and Oxford Down race give optimum specificity of antibodies against the proteins described above. It is contemplated that an especially intersecting type of pigs for use as host animals for the present purpose are the so-called SpF pigs, that is, pigs which have been born and grown under sterile conditions, as such pigs will not in advance be loaded with antibodies against the antigens otherwise normally occurring during the initial stages of the pig's life, which means that by the immunization performed according to the present invention, it is possible to obtain an IgG fraction with a high proportion of specificity against the antigen or antigens included in the vaccine used.

The pigs are selected in an age of 4 months, and a first subcutaneous vaccination is applied at one side of the neck, thereafter the pigs are checked for response to the vaccination. At proper response, the vaccination sites are swollen and possibly ulcerated (like wounds), similar to a positive response to smallpox vaccination.

Furthermore, titer determination and IgG determination on the pig serum is made in the following way:

Anti C1 IA titer: A standard human serum with known C1 IA concentration (30 mg/ml ± 10%) is subjected to rocket immunoelectrophoresis against 2% rabbit antihuman C1 IA (2 mg/ml) in the gel. The resulting rockets are now used as standard for comparison with immunoelectrophoresis rockets of the standard human serum against dilutions of the pig antiserum in gels. The dilution of the pig antiserum giving the same rocket height as the 2% rabbit antihuman C1 IA-containing gel contains 2 mg/ml pig antihuman C1 IA, and by multiplication with the correction factor corresponding to the dilution, the pig antihuman C1 IA titer is calculated.

Anti C1 IAC titer: The same procedure is followed, this time using a standard solution of C1 IAC Sephadex ® G75 Superfine instead of the standard human serum. A gel dilution of the pig serum giving the same rocket height as the 2% rabbit antihuman C1 IA is ascribed a titer of 2 mg/ml, and calculations to correct for dilution factors are carried out.

IgG: The mean concentration of IgG in the pig serum is determined by rocket immunoelectrophoresis in the same manner as described above, using 4% rabbit antihuman IgG in the gel. As standard is used standard human serum batch 974 Behringwerke.

3 Weeks subsequently to the first vaccination, a booster dose of vaccine is administered subcutaneously at the other side of the neck. Again, the pigs are checked, and their serum examined as described above.

A second booster dose is given on the back, partly deeply intramuscularly, partly subcutaneously, 4 weeks after the first booster vaccination. About 6 days subsequently to the second booster vaccination, the pigs are again checked as described above, and their blood antibody titer and specificity are examined as described above. Normal mean values after second booster are approximately 2 mg/ml of anti C1 IA, 2 mg/ml of anti C1 IAC, and about 1200 mg% of IgG.

9-14 Days after the last vaccination, the pigs are bled after electroshock in sanitary slaughtery as described below.

Sheep are vaccinated at the neck as described for pigs. These animals may be drained as donor and may advantageously be re-vaccinated and drained several times. Normal mean titer values from the sheep (determined analogously to the method described above) are about 1 mg/ml of anti C1 IA, 3 mg/ml of anti C1 IAC, and about 1500 mg% of IgG.

Examples of preferred vaccine products.

Type 1:

C1 IAC$_{aggregated}$ protein + C1 IAC Sephadex ® G75 Superf. is given as initial vaccination in a total amount of 20 mg, dissolved in 1 ml 0.15 M NaCl, made into water-in-oil emulsion with equal volume of Freund's complete adjuvant.

As booster dose, 20 mg of C1 IAC$_{aggregated}$ protein + C1 IAC Sephadex ® G75 Superfine is admixed with 20 mg of C1 IAC/C1 IA DEAE Sephadex ® A50 + 20 mg of C1 IAC/C1 IA, $\alpha_2$HS, Zn $\alpha_2$, orosom. The mixture is resuspended in 1 ml 0.15 M NaCl and made into water-in-oil emulsion with equal volume of Freund's complete adjuvant. This booster is suitable as first and second booster doses for pigs and sheep.

Type 2:

C1 IAC$_{aggregated}$ protein + C1 IAC Sephadex ® G75 Superf. is given as initial vaccination to production animals of the type of sheep or pigs for use in the preparation of antiserum for diagnostic or therapeutical purposes.

As booster dose, C1 IAC/C1 IA DEAE Sephadex ® A50 is used resuspended in 1 ml 0.15 M NaCl, made into water-in-oil emulsion with equal volume of Freund's complete adjuvant. This vaccine may be used for booster doses.

The bleeding of pigs is performed in the following manner. Firstly, the animals are given electroshock, whereafter they are, in an unconscious state, bled via funnel-shaped drains into sterile 5 liter Pyrex bottles containing 1 liter citrate of the type ACD as anticoagulating agent. It would be possible to use other anticoagulating agents, e.g., heparine, but because of the very pronounced coagulation tendency of pig blood, ACD is the preferred anticoagulation agent. Thereafter, the blood is kept under cool conditions until working up.

In working up, plasma centrifugation is performed on an MSE Mistral 6L Cooled Centrifuge at 4000 rpm. The plasma is immediately frozen hard to $-20°$ C. and is kept at $-20°$ C. until further fractionation to immunoglobulins is performed.

Prior to immunoglobulin fractionation, the pig plasma is sterile-filtered, e.g. using a Millipore filter, pore size decreasing to 0.22 $\mu$.

The working up of the pig serum to result in a product comprising the IgG immunoglobulins and substantially no other pig protein may be performed in accordance with well-known methods, e.g. combined Rivanol and ammonium precipitation, and examples of suitable methods are the ones described by Schwick et al., Progress Immunobiol. Standard 4, 96, Basle, Munich, New York, (1968) (Karger), by Horejsi, J., and Smetana, R., Acta Med. Scand. 155, 65 (1956), and by Dietzel, E., et al., Behringwerke Mitteilungen 43, 129, (1964).

The pig IgG immunoglobulins prepared as described above have been administered intraveneously daily for 4 months to a male cancer patient, with a disruption of 14 days (holiday) starting 1½ months from the beginning of the treatment. The patient was continuously checked immunologically for any signs of development of immune response against the pig IgG immunoglobulins, including tests for precipitation by interaction of the patient serum with the pig IgG immunoglobulins (other than the precipitation due to the presence, in the patient serum, of the proteins against which the pig had been immunized (using also IgG from a non-immunized pig as control), tests for production of IgE, tests for interaction between patient serum with other pig proteins, etc. The immunological checking revealed no development of an immune response against pig IgG in the patient, not even after the 14 days' interval. Neither was there any clinical indication of any non-tolerability of the pig IgG.

DIAGNOSTIC KITS.

In order to obtain a useful and reliable diagnostic kit permitting differential diagnosis between malignant and non-malignant diseases and the course of a malignant disease, both in relation to the non-treated stage and in relation to different treatments and the after-treatment period (the latter in order to ascertain whether relapse of cancer occurs), a diagnostic kit according to the invention is preferably one which comprises antihuman C1 IAC or an immunologically active modification or derivative thereof, and is so designed and used that the immunological reaction with C1 IAC in a sample is easily distinguishable from any response to C1 IA in the sample. This is a basic requirement which must be fulfilled by any diagnostic kit according to the present invention, as it is the presence of C1 IAC in the sample from a patient which is the unambiguous indication that the patient suffers from cancer.

As has been explained above, the serum levels of C1 inactivator (C1 IA + C1 IAC) and C4 are useful as indications of the course of verified cancer diseases and the course of after-treatment period, and moreover, high level of C1 inactivator is indicative of a cancer disease, cf. FIG. 2, and one aspect of the invention concerns diagnostic kits for use in monitoring the course of cancer diseases, such diagnostic kits comprising anti C1 IA and anti C4. However, a high level of C1 inactivator is not conclusive evidence of a cancer disease, as, also, certain virus infections might give rise to high C1 inactivator levels which, moreover, could be accompanied by high C4 levels. In case of such non-malignant virus diseases, the level of C1 inactivator, although high, would not comprise any C1 IAC. Hence, a diagnostic kit giving a safe distinction between such non-malignant diseases and cancer is one which is able to selectively show the presence of C1 IAC in a sample.

Figure 4:
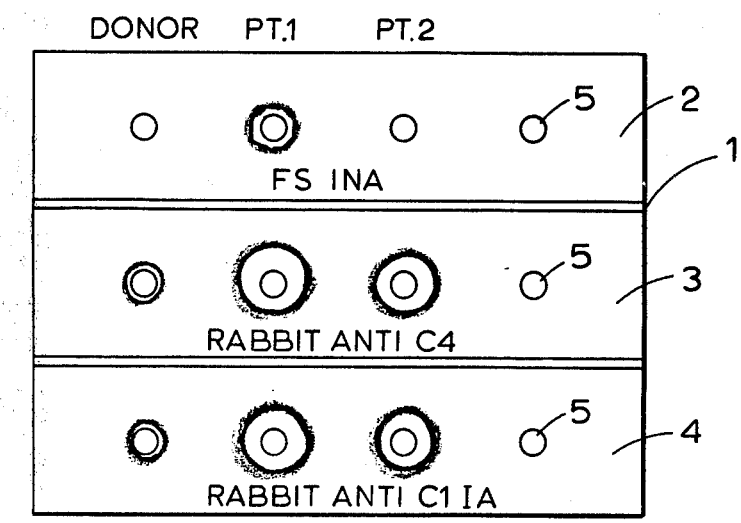
FIGS. 4, 29 and 30 show test kit slides.

One embodiment of a preferred diagnostic kit according to the invention and fulfilling the above three requirements is illustrated in FIG. 4. The kit comprises a glass plate or other suitable support 1 on which three sections of gel layers (2, 3, and 4) with different antisera are applied. In the gel layers, holes 5 are made by punching or other suitable technique. In gel section 2, a material containing antihuman C1 IAC is incorporated. This material may be an oligospecific serum which is responsive to both C1 IAC and C1 IA, but distinguishes between them, (e.g. prepared on sheep using a type 2 vaccine as described in the section "Vaccination of Host Animals"), in which case a serum sample from a healthy donor or a patient suffering from a non-malignant disease will give only one precipitation ring, whereas serum from patients suffering from cancer will give two precipitation rings. Preferably, however, the antihuman C1 IAC-containing material incorporated in the gel in section 2 is a monospecific antihuman C1 IAC material, e.g. prepared by absorbing antibodies against any other human serum proteins from an antihuman C1 IAC-containing material by incubation with whole serum from healthy donors and subsequently separating, such as described below. In case of such monospecific antihuman C1 IAC material in section 2, the response to a cancer patient serum sample in section 2 will be a single ring around the punched hole in which the sample has been applied, whereas the response to a healthy donor or a patient suffering from a non-malignant disease will be the total absence of any precipitation ring around the hole in which the sample was applied. This is considered to be the most characteristic and unambiguous reaction obtainable. In FIG. 4, "FS INA" indicates such a monospecific antihuman C1 IAC-containing material prepared by absorption from antiserum produced in sheep.

In the section designated 3, an antihuman C4-containing material is incorporated in the gel, e.g. a commercial rabbit antihuman C4. In the section designated 4, antihuman "C1 inactivator" is incorporated in the gel; it is, e.g. rabbit antihuman C1 IA, which, as described above, is not able to distinguish between C1 IAC and C1 IA and which will therefore give precipitation with the sum of C1 IA and (if present) C1 IAC in the serum sample applied. Of course, also in the sections designated 3 and 4, the immunologically active material showing the desired reaction may be a modification or derivative of the native antibody, the requirement being that it shows the characteristic immunological reactions with C4 and C1 IA, respectively. The sections designated 3 and 4 are used for qunatitative estimations of the levels of C4 and C1 inactivator, respectively.

As will be seen from FIG. 4, blood from healthy donor has given no precipitation ring in the FS INA section, whereas precipitation rings of relatively small diameters are seen in the anti-C4 and anti-C1 IA sections, corresponding to normal low values of C4 and C1 IA. The serum from patient No. 1 has given a precipitation ring in the FS INA section, evidencing that the patient suffers from cancer. In the anti-C4 section, the precipitation ring has a large diameter and indicates that the serum levels of C4 are high, and also in the anti-C1 IA section, a large precipitation ring is seen, indicating that the level of C1 inactivator (C1 IA + C1 IAC) in the patient serum is high. The serum from patient No. 2 gave large precipitation rings in the anti-C4 and anti-C1 IA sections, but no precipitation ring in the FS INA section. This shows that the patient is not suffering from cancer, but that his C4 and C1 inactivator levels are abnormally high, which may due to, e.g., a virus infection.

A preferred diagnostic kit of the type illustrated in FIG. 4 is prepared in the following manner: 1% agarose in diemal buffer, pH 8.6, is heated until fluid (other gels, e.g. agar, and other buffers may also be used, but the combination stated here has been found to give excellent results). Thereafter, the gel is cooled to 45° C., and the antiserum is added. A suitable antiserum for the anti-C4 section is rabbit antihuman C4 which is preferably added in an amount of 1%. For the anti-C1 IA section, rabbit antihuman C1 IA gives excellent results when used in an amount of preferably 1%. For the anti-C1 IAC section, the preferred material (giving a precipitation ring only in case of cancer) is sheep antihuman C1 IAC (absorbed, if necessary), added in an amount of 0.25% (the preparation of the sheep antihuman C1 IAC (absorbed) is described in detail below).

After the addition of the antibody or antiserum, each separate gel portion is cast in the desired configuration on the support, whereupon the gel is allowed to solidify at room temperature. When the gel has solidified, holes are punched in the desired amount and pattern, e.g. as shown in the drawing, and the gel sections are appropriately marked as desired. The diagnostic kits are wrapped in suitable manner and preferably accompanied with prescriptions for use and with photos showing characteristic responses, as well as standard calibration curves for determining the serum level of C4 and C1 inactivator from the diameter of the precipitation ring thereof.

Naturally, several modifications may be made in the above design and procedure. For example, each of the gels may be delivered on a separate support, and several other designs than the one shown in the drawing are useful; these are trivial modifications and obvious to one skilled in the art. Also, other carrier materials than the gel described can be used. However, the embodiment described above has been found to give excellent and unambiguous results in practical use.

The sheep antihuman C1 IAC (absorbed) used in the above procedure was prepared as follows: To 10 ml of sheep antihuman C1 IAC prepared as described in the section "Vaccination of Host Animals" (using vaccine type 2) and having an immunoglobulin concentration of 1500 mg% IgG and a specific antibody titer of 3 mg/3 ml, 400 microliter of human donor serum (which has, of course, not been heat-inactivated) is added, and the mixture is incubated at 37° C. for 30 minutes. Thereafter, centrifugation at 3000 rpm is performed, and the supernatant is incubated at 4° C. and centrifugated again. The supernatant from the last centrifugation is used as the sheep antihuman C1 IAC (absorbed).

Figure 29:
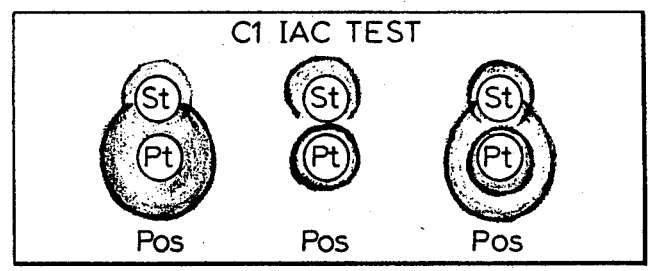
Figure 30:
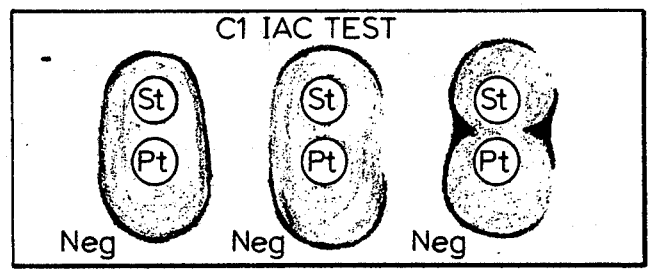

Another preferred embodiment of a diagnostic kit according to the invention is a comparative immunodiffusion (Weir, Handbook of Experimental Immunology, Vol. 1, Immunochemistry, Blackwell Scientific Publications, 1973, page 19. 12) agarose gel kit with punched sets of holes, as illustrated in FIGS. 29 and 30. A kit of this type is suitable as a screening test and also, to a certain extent, for semi-quantitative mounting of the C1 IAC level in patient body fluids, especially serum. The comparative immunodiffusion test kit illustrated in FIG. 29 and 30 is prepared by casting an antiserum-containing agarose gel on a glass plate and thereafter punching matched holes in the gel when solidified. A preferred gel for use in the comparative immunodiffusion test kit is a Litex agarose gel or In dubiose A 37 agarose gel, both with low electroendosmosis. The same gel may also be used for the preparation of test kit containing anti C1 inactivator and anti C4, but the average serum concentration in relation to standard serum concentration is diminished for anti C1 inactivator and anti C4 when using low electroendosmosis gel.

For the preparation of the comparative immunodiffusion test kit, the Litex agarose gel or Indubiose A 37 agarose gel is dissolved in diemal buffer, pH 8.6, in a concentration of 1% of gel. The solution is autoclaved at 120° C. and thereafter cooled to 51° C. At this temperature, the antiserum (usually sheep antiserum (usually non-absorbed)) is added to the gel in the desired concentration, the concentration being adjusted upon initial precipitation test against an aliquot of a "standard cancer serum" in such a way that from charge to charge, the precipitation ring with the said standard serum will always be of the same diameter. This assists in the semi-quantitative reading of the C1 IAC precipitate and is a normal technique used in the preparation of Mancini immunodiffusion tests. To the gel, 1% of sodium azide and 0.1% of merthiolate are added as bacteriostatic or fungicidal agents. Instead of non-absorbed sheep antiserum, also absorbed sheep antiserum, or pig antiserum or pig IgG immunoglobulin fraction may be used in this comparative immunodiffusion or haloplate technique test according to the present invention.

Reference is made to FIGS. 29 and 30. In FIG. 29, three positive C1 IAC reactions are shown in the lower row of punched holes. It is evident that in all cases, the precipitation cross-reacts completely with the standard C1 IAC-negative (blood donor serum or pooled blood donor serum) antigen applied in the upper row of holes. In the middle hole, the C1 IAC ring is completely round without any inhibition against the standard antigen-containing serum. In the lower left hole, a larger ring is visible, indicative of a larger concentration of C1 IAC. In the right hole, two distinct rings, one without inhibition against standard serum, the other one cross-reacting with standard serum, are seen. One of these rings is a C1 IAC precipitation ring, whereas the other one is a CAAC precipitation ring, vide the section "CAAC".

In FIG. 30, three typical examples of negative C1 IAC tests are shown. It will be seen that in two of the three cases, completely coalescent rings are formed between the patient serum and the standard negative serum, whereas in the third row are both a coalescent ring and inhibition of the ring between standard and patient serum is seen, indicating identity between the two types of antigens.

When using the comparative immunodiffusion test kit according to the invention, the patient serum and the standard negative serum should also be applied in the same amounts and in the same concentrations, preferably 10 microliters per hole, preferably undiluted, and the incubation time is preferably 48 hours at room temperature or 72 hours at 4° C.

An optimum distance between the punched holes (the upper hole for standard negative serum and the lower hole for the patient serum) is 2 mm between the hole periferies, the diameter of the holes being 5 mm.

The diagnostic kits according to the present invention should be stored under cool conditions (4°-8° C.), and in humid atmosphere or in a sealed container. The shelf life of the diagnostic kits according to the invention is estimated to be about 1 year under these conditions.

The best reading of the diagnostic kit tests according to the invention are obtained after staining with e.g. Coomasie Blue. Before the staining, the gel is salted out with saline (0.15M) overnight and subsequently rinsed in distilled water for one hour. The staining with Coomasie Blue is followed by de-staining with methanol/acetic acid solution, and the test is thereafter dried at room temperature until the film has hardened. Thereafter, it is possible to de-stain once more with the same solution in order to get a more clear background.

Of course, the reagents used for preparing the diagnostic kit should be carefully checked for purity and specificity, and scrupulous quality control on the kit prepared should be carried out.

The patient serum used for the C1 IAC immunodiffusion test according to the invention (or for any other test according to the invention for showing the presence or absence of C1 IAC) should preferably not be more than 8 days old, and should be kept under cooled conditions (preferably at 4°-8° C., less preferably under refrigeration) until the test is performed. However, if it is necessary to store the serum sample for longer periods before the test can be performed, it should be stored at −80° C. or lower, although a limited storage period (of the order of about a fortnight) at −20° C. will not seriously impair the reliability of the test result.

A comparative immunodiffusion test of the type described above is also used for monitoring the C1 IAC specificity on serum samples taken from vaccinated animals during the immunization. In this case, the antiserum sample from the animal is incorporated in the gel in varying concentrations, and an aliquot of a C1 IAC-positive standard serum (of a "standard" C1 IAC concentration which is the same from time to time), said aliquots being kept at $-80°$ C. for storage, is applied in the lower hole, while standard negative serum is applied in the upper hole in the same concentration. The size of the C1 IAC ring obtained in the test gives a measure of the C1 IAC specificity titre of the animal serum.

EXTRACORPORAL DEBLOCKING AND DEMASKING OF CANCER PATIENT SERUM

In a deblocking central using immobilized INA antibodies, blocking and demasking proteins are removed from cancer patient serum by immunoadherence to the antibodies. In accordance with preferred aspects of the present invention, the immobilized antibodies will comprise at least antibodies against C1 IAC, optionally also against C1 IA and preferably also antibodies against orosomucoid, $\alpha_2$HS glycoprotein, and Zn $\alpha_2$ glu coprotein. While it is within the scope of the present invention to use, as immobilized antibody against C1 IAC and C1 IA, a non-distinguishing antibody such as rabbit antihuman C1 IA, it is highly preferred to use the specific antibodies against C1 IAC and C1 IA prepared as described herein and on host animals, the serum of which is known to be more tolerable by human beings, and so far, there has been no evidence that the concomitant use of antibodies against orosomucoid, $\alpha_2$HS glycoprotein, and Zn $\alpha_2$ glycoprotein is not advantageous, for which reason the preferred INA for use in extracorporal treatment of cancer patient serum will have the same antibody composition as the preferred INA for intravenous administration.

A preferred material for preparing matrix immobilized antibodies according to the present invention is CNBr-Sepharose ® 4B from Pharmacia. This material is described in the publication "Affinity Chromatography, Principles and Methods", published by Pharmacia Fine Chemicals, Uppsala, Sweden, October, 1974, especially pp. 8-15 and 57-58. Naturally, other matrix materials showing similar good properties with respect to immobilizing the antibodies without impairing their activity and with respect to practical elution properties may also be used.

An example of immobilizing of INA by coupling to CNBr-Sepharose ® 4B and deblocking and demasking of cancer patient serum is given below.

30 mg of lyophilized and resuspended INA, prepared on pig using vaccine type 1 as described in the section "Vaccination of Host Animals" were applied to CNBr-Sepharose ® 4B following the procedure described in pages 8-15 of the above-mentioned publication.

The resulting INA activated matrix gel was packed in a Pharmacia K 15/25 column. The column was equilibrated with Tris/HCl buffer solution (0.2 M, pH 8) containing 0.5 M NaCl.

10 ml of serum from a patient suffering from cancer was applied to the column, and elution was performed with the Tris/HCl buffer 0.2 M, pH 8.0 containing 0.5 M NaCl. The eluted fractions were monitored spectrophotometrically, and the fractions containing proteins were collected. Identification and quantitative estimation of C1 IAC/C1 IA was performed by Laurell rocket immunoelectrophoresis on the cancer serum before applying to the column and on the fractions eluted. It was found that the original C1 inactivator (C1 IAC + C1 IA) content of 60 mg% in the original serum was lowered to a value of 15-20 mg% by the treatment. (The estimations were performed in the fractions contained in the effluent of Tris, but were corrected for the dilution).

After the elution, the column was made ready for a new run by elution with a glycine/HCl solution (0.2 M, pH 2.8) containing 0.5 M NaCl, and subsequent passing of isotonic saline and equilibration with the Tris/HCl buffer 0.2 M (pH 8.0) + 0.5 M NaCl.

Figure 22:
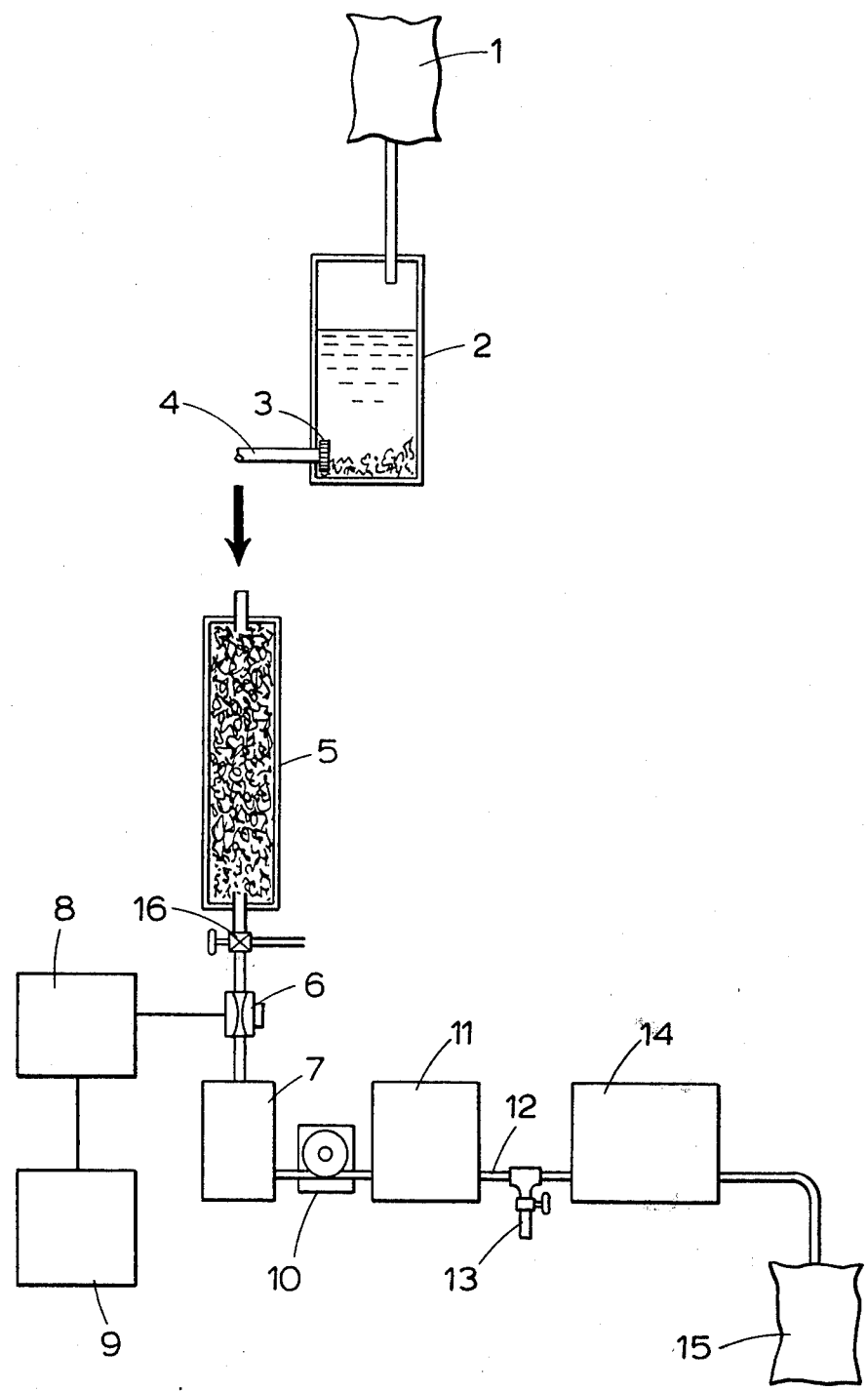
FIG. 22 shows a deblocking central or plant.

In the practical cancer therapy using extracorporal deblocking with the aid of immobilized INA antibodies, the treatment of the patient serum is suitably performed in a central to which the cancer patient plasma is sent after plasmaferesis of the patient. In FIG. 22, an embodiment of a deblocking central or plant according to the invention is shown. Referring to FIG. 22, a bag 1 with patient citrate plasma (ACD plasma) is emptied into a recalcifying reservoir 2 in which the recalcification is carried out at 37° C. for 30 minutes. The serum passes through a filter 3 which retains fibrin clot and into a line 4 from which it is passed to a column 5 cooled to 8° C. by means of a cooling mantle. The column contains matrix-immobilized INA, e.g. INA applied on CNBr-Sepharose ® 4B loaded with INA as described above. Antibiotics in appropriate amount have been added to the column. The column size and the loading with INA are so adapted that the column contains an excess of immobilized antibody compared to the content of the corresponding antigens in the serum.

Elution of the column is performed with Tris/HCl buffer 0.2 M (pH 8.0) + 0.5 M NaCl as described above, and the eluate passes through a cuvette 6 into a reservoir 7. The eluate passing through the cuvette 6 is monitored by means of a spectrophotometer 8 with a recorder or plotter 9. When the serum proteins have been eluted (as ascertained by means of the spectrophotometer), the eluate is pumped from the reservoir 7 by means of a pump 10 into a pressure dialyser 11, e.g., a unit functioning in accordance with the kidney machine principle. From the pressure dialyser 11, the serum passes into a line 12 with a sample withdrawal valve 13 into a sterile filter 14, from which it is collected in a sterile bag 15 for reinfusion into the patient. Samples withdrawn through the valve 13 are examined for content of C1 IAC/C1 IA and orosomucoid, $\alpha_2$HS glycoprotein, and Zn $\alpha_3$ glycoprotein by immunoelectrophoresis and for content of impurities by suitable methods, e.g., by gas chromatography for content of CNBr. Similar control analysis may also be performed at other stages, e.g., gas chromatography before the pressure dialyser. Preferably, all manipulations of the serum are performed before the sterile filter, the only operations performed after the sterile filter being check for sterility and pyrogen content.

After the serum run, the column 5 is regenerated with glycine/HCl and equilibration with the Tris buffer. The eluate from the glycine/HCl treatment and the equilibration is discarded, e.g. through a line 16.

Various examinations are carried out in connection with the deblocking. For example, the plasma is checked for sterility and pyrogen content on arrival to the central, and the patient is examined for fibrin and fibrin split products. Also, serum C1 inactivator and C4 levels are, of course assayed on serum samples from the patient, and lymphocytes are checked for types B, T, and O. Apart from this, standard laboratory tests are performed, in the same manner as in treatment with cytostatics.

An important check on the patient is the determination of coagulation factor, as part of the coagulation products is removed in the conversion of the plasma into serum. However, cancer patients have often ample fibrin levels. If found necessary, coagulation factor is supplied to the patient, e.g. by infusion of donor plasma or in the form of Lysofibrin (Novo).

CANCER THERAPY WITH IMMUNE SERUM ACCORDING TO THE INVENTION.

In the following, three preliminary attempts to utilize unblocking sera according to the invention in short-time treatment of human cancer are reviewed. In addition to the treatment reported below, also other cancer patients have been treated and remission, i.e., a decrease in tumor mass, has been ascertained. However, the treatments here reported were the first ones in which a more complete specification of the effect of the treatment was possible.

Unblocking immune sera.

INA (Immune Neutralizing Antiserum) unblocking sera were produced on pigs and sheep as described above. The pig serum contained antibody with a titer of 2 mg/ml against C1 IAC in total serum, estimated as described in the section "Vaccination of Host Animals". The means concentration of 1gG in the pig total serum was 1200 mg/100 ml, as estimated using antihuman 1gG. The antibody titer against C1 IAC in sheep serum was approximately 3 mg/ml. The sera were fractionated on a sterile Sephadex ® G200 column using sodium phosphate buffer at physiological pH, and fractions containing immunoglobulin were isolated, dialyzed, and lyophilized. At the start of treatment, the lyophilized protein was resuspended in isotonic saline. The purified INA unblocking serum was estimated to contain 10 mg IgG/ml (by rocket immunoelectrophoresis using antihuman IgG).

Routine investigations of patient during immunotherapy with INA.

Monitoring of the patient with ECG, pulse rate, external and internal temperature control.

Serum concentrations of immunoglobulins, complement component C4, and C1 inactivator (C1 IA + C1 IAC) were estimated consecutively before, during and after treatment. Serological tests were performed by rocket immunoelectrophoresis a.m. Laurell, C. B., Analyt. Biochem., 15, 45 (1966), using the following test sera: Rabbit antihuman C1 IA (antibody content 0.7 mg/ml), and rabbit antihuman C4 (antibody content 1.0 mg/ml), both from Behringwerke. Rabbit antihuman IgG (antibody content 0.4 mg/ml) and rabbit antihuman IgM (antibody content 0.4 mg/ml) from Dakopatts, Copenhagen. Immunoglobulin coat and secretion of the patient's lymphocytes were investigated consecutively in accordance with the following method.

Lymphocytes are separated from a citrate-containing blood sample from the patient by Isopague-Ficoll gradient centrifugation followed by washings in Hanck's stock solution with centrifugation after each washing. The resulting lymphocyte pool is divided in two portions. One portion is examined for presence of coat of immunoglobulins as described in Osther, K. and Dybkjaer, E., Scand. J. Haemat., 13, 24 (1974). The other portion is trypsinized using Trypure-PBS buffer for 2 minutes at 37° C. The trypsine effect is stopped by repeated washings in Eagle MEM containing 15% inactivated foetal calf serum. Thereafter, the lymphocytes are checked for presence of immunoglobulin. When found negative, the lymphocytes are incubated in Hanck's stock solution at 4° C. overnight. Thereafter, the lymphocytes are separated and then incubated in FITC-marked antihuman immunoglobulins. FITC (Fluorescein Isothiocyanate) was from BBL, Cockeysville, Md., USA. The antisera were conjugated with FITC a.m. Fothergill, J. E. (Properties of conjugated serum proteins. In Nairn, R. C., (ed.), Fluorescent Protein Tracing, pp. 5, 3rd ed. E. & S. Livingstone Ltd., Edinburgh and London (1969)). Immediately thereafter, the immunofluorescence of the lymphocytes is measured by cytophotometry as described in Osther, K. and Dybkjaer, E. (Scand. J. Haemat., 13, 24 (1974)).

Figure 24:
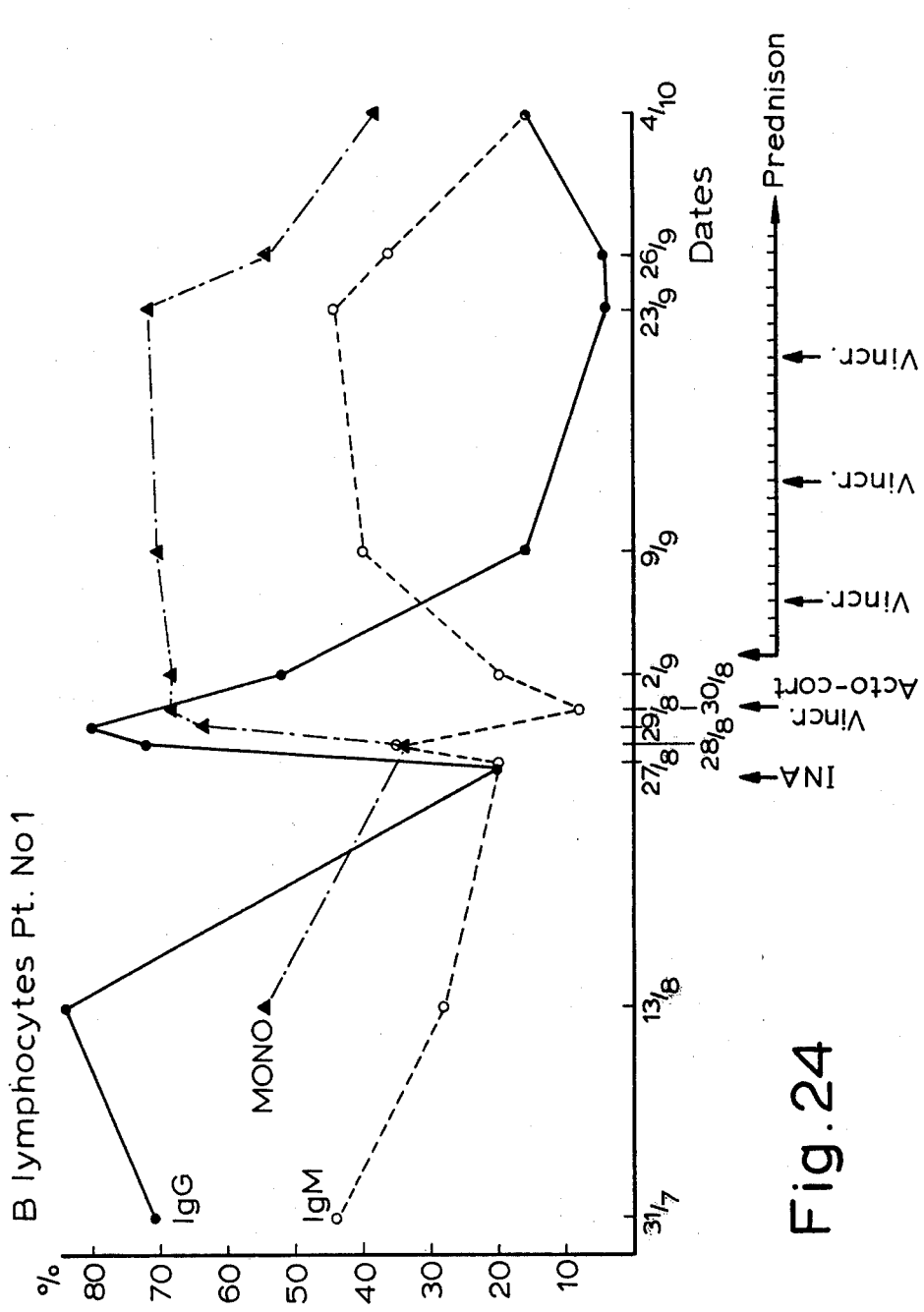
FIGS. 24, 26 and 28 show amounts of secreting lymphocytes.
Figure 26:
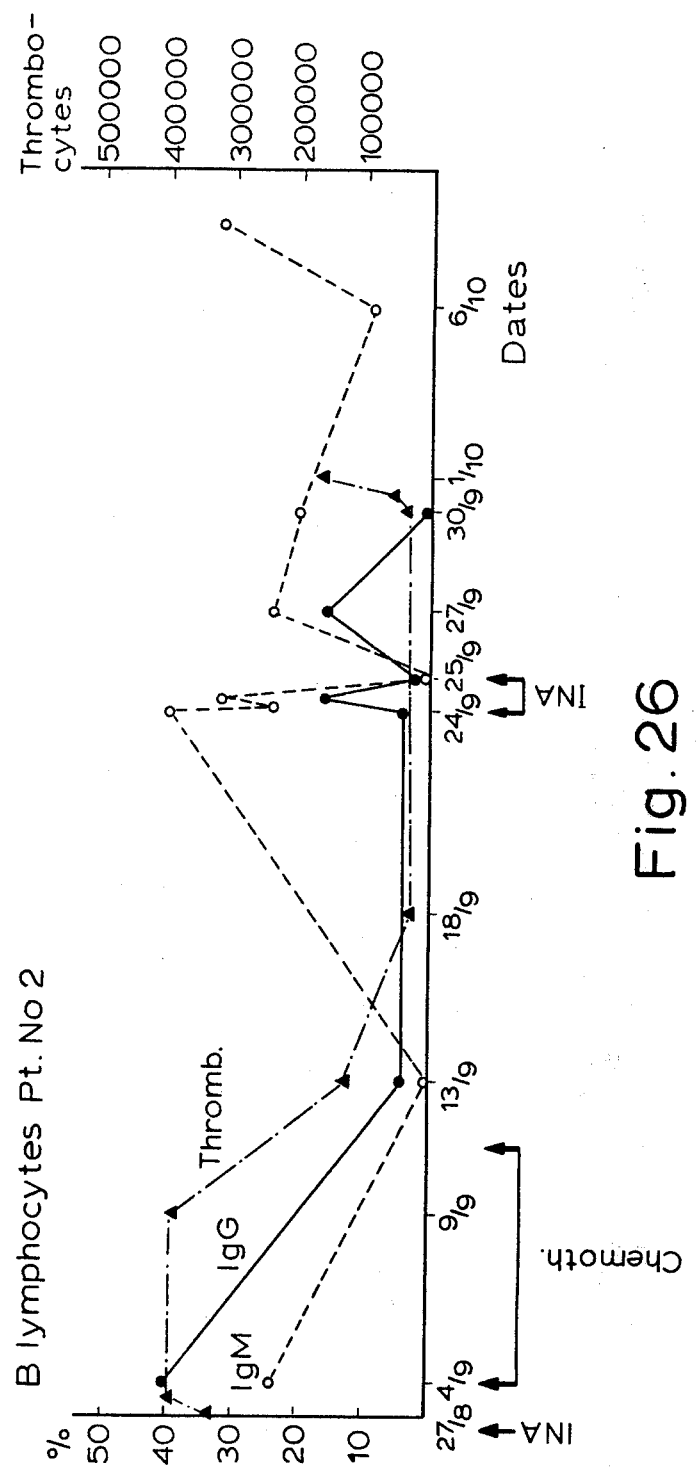
Figure 28:
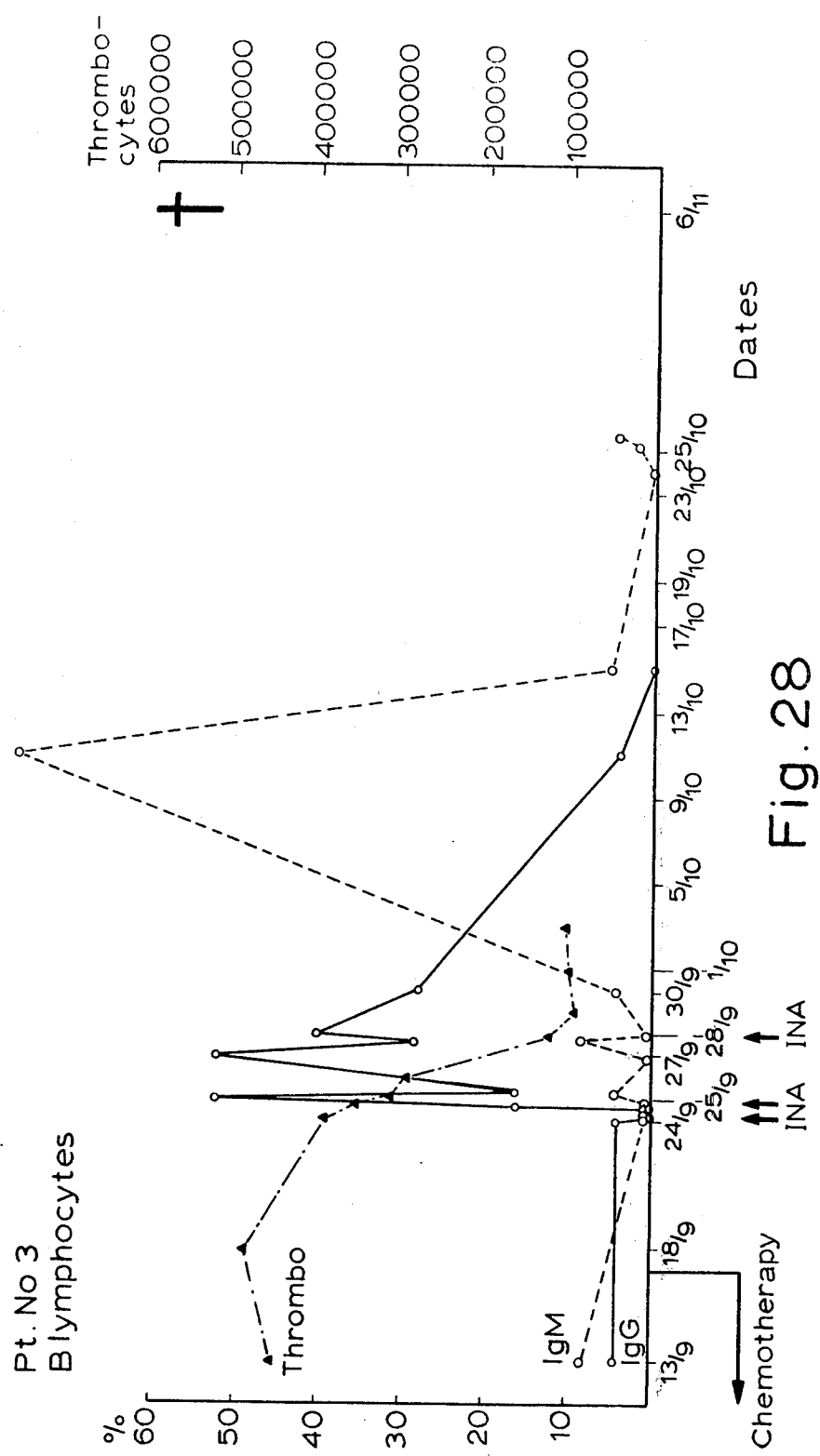

Of course, the lymophocytes in both portions are checked for viability by the well-known trypane blue technique, and calculation of the number of cells coated with immunoglobulins is corrected for non-viable cells. The amounts of secreting lymphocytes shown in FIGS. 24, 26, and 28 are the amounts of secreting lymphocytes ascertained in the portion incubated in Hanck's stock solution, the other portion being used primarily as a reference and control.

PROCEDURE OF TREATMENT.

Intracutaneous test with INA unblocking serum diluted 1:10 was set and reaction noticed, if any. The patient was pretreated with antihistamine in order to avoid a iatrogenic histamine release in the patient.

The INA unblocking serum, diluted in saline, was administered intravenously. Drop count and total dose were administered according to the condition of the patient.

RESULTS.

Case Story 1

A 28 months old boy, with a histiocytary lymophoma, verified histologically 8 months previously. At the time of the first admission he showed disseminated lymphomas, bone marrow infiltration and marked thrombocytopenia. No hepatosplenomegaly.

Primarily, the patient had been treated and immunosuppressed with Vincristine, cyclophosphamide, streptonigrin, and prednisone. Total initial dose of Vincristine 3.5 mg administered during 6 weeks, followed up by a total of 3.0 mg administered during 4 months. During the period of treatment, the lymphomas diminished, and thrombocyte count normalized. One single bone marrow sample showed no malignant cells. In the same period rather severe infections occurred. Other side effects as ataxia and finally edema cerebri contradicted further cytostatic treatment.

Six weeks previous to actual treatment, testes started growing fast, and the right testis was removed. Testes were infiltrated with solid reticulosarcoma extending in the resection zone.

Left testis was spared. The bone marrow revealed again sarcomatous infiltration. A new drop in the thrombocyte count was treated by transfusions.

With the parents' consent, the patient was treated with 180 ml of INA (pig), diluted in saline, administered intraveneously.

In order to avoid a possible disseminated intravascular coagulation, the patient was heparinized. Four days following the INA treatment, the patient was given Vincristine in a total of 1.75 mg administered weekly. Already following the second dose, the left testis diminished. Bone marrow turned normal. The patient redeveloped neurotoxic symptoms, ataxia and paresis, but since this treatment, no serious infections were noticed.

Three months after ceased treatment the patient had been checked several times. No lymphomas have reoccurred, left testis is of normal size without sign of tumor. Bone marrow has been checked several times without any signs of tumor cells. Neither has scanning revealed any signs of relapse.

Figure 23:
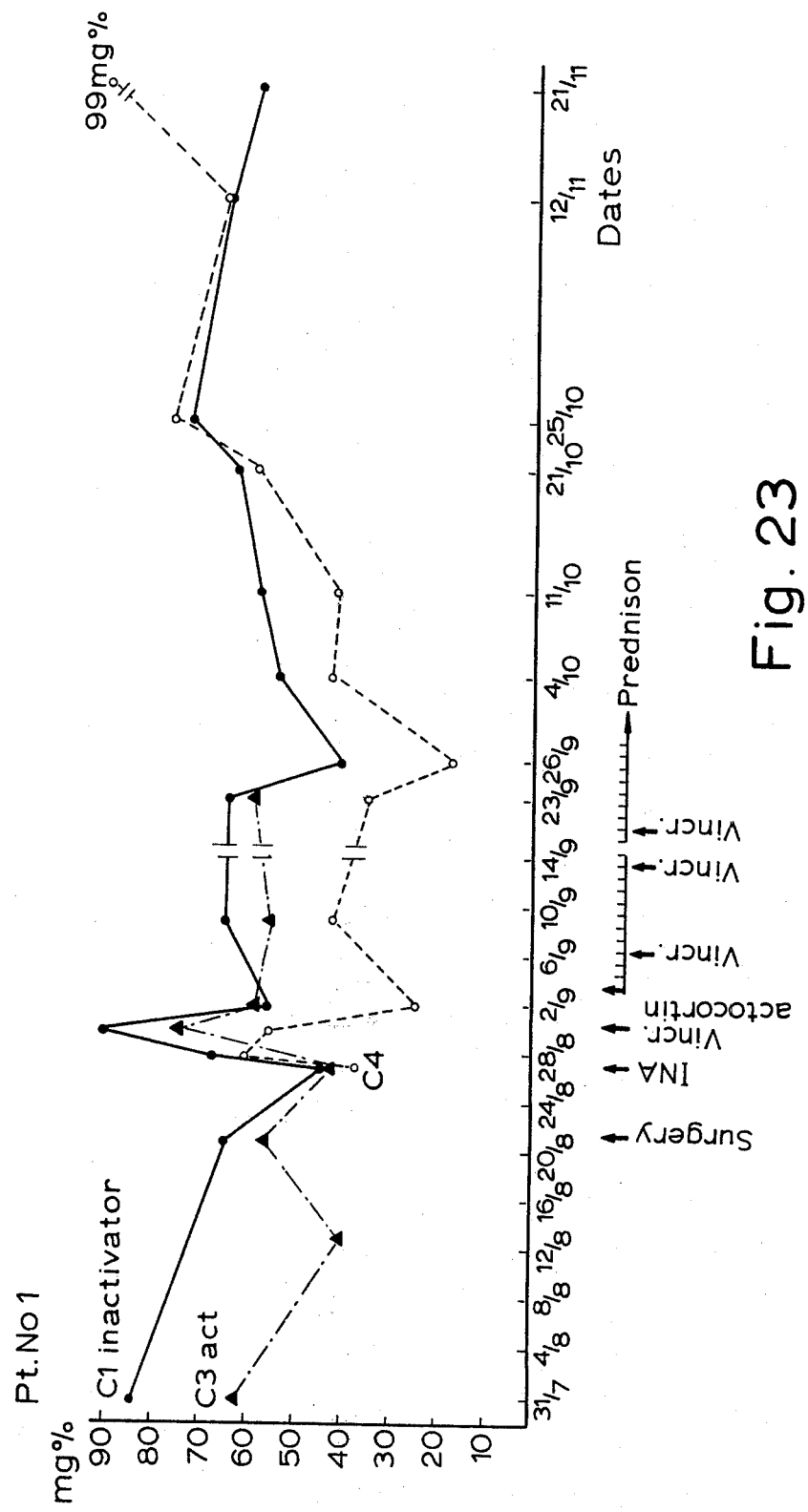
FIGS. 23, 25 and 27 show amounts of C1 inactivator.

Alterations before, during and after INA treatment period in complement component C4 and C1 inactivator are visualized in FIG. 23. The concentration of C1 inactivator declimbes slowly, but significantly.

Alterations in immunoglobulin coated cells and in amount of monocytoid cells (MONO), among them non-classified cells, is demonstrated in FIG. 24. The high percentage of IgG coated and IgM coated cells declimbes in connection with the INA treament, and a few days after reverses to almost the same percentage. The following days, the amount of IgG coated cells again declimbes, while the IgM coated cells count rises simultaneously to the elevation of monocytoid cell count.

Case Story 2

A 53 years old female suffering from disseminated metastases from mammary carcinoma. Histiologically, roentgenologically and scintigraphically verified osseous metastases, bone marrow carcinosis and cutaneous metastases, deriving from a solid carcinoma.

The patient had previously been treated with irradiation against bilateral supra, infra and axillary lymph nodes, and palliative irradiation against lumbar column. After relapse, the patient was initially treated with INA (pig) unblocking serum, total dose 680 ml. No significant temperature rise occurred. One week after the initial treatment, the patient received two cycles (one week interval) cytostatic treatment with Vincristine (total dose 1.15 mg), 5-fluorouracil (total dose 600 mg), metothrexate (total dose 45 mg), cyclophosphamide (total dose 150 mg) and prednisone (total dose 550 mg). 27 Days following the first INA treatment, a second and a third INA (sheep) treatment were administered with an interval of 7 days (total dose of the two cycles 580 ml). Maximum temperature rise 40.4° C. One month after last INA treatment, the patient was given a total of 5.0 mg Vincristine for a period of two months, 5-fluorouracil (1355 mg), and metothrexate (100 mg) and now a perorally administered dose of 70 mg cyclophosphamide is given daily.

Seven days after the initial INA treatment serum uric acid reached extremely high values, and 15 days after (8 days after first cytostatic cycle) cutaneous metastases flattened, and are not changed to horny scars. The osteolytic metastases are after a period of 3.5 months replaced by osteosclerotic alteration. One bone marrow sample showed normoplastic marrow, another showed small islands of tumor cells surrounded by lymphocytes and connective tissue, and normoplastic marrow. The patient is after a period of 3.5 months physically in good health. Alkalic phosphatases are normalized BSR = 10 mm/hour, and the laboratory check shows normal condition.

Figure 25:
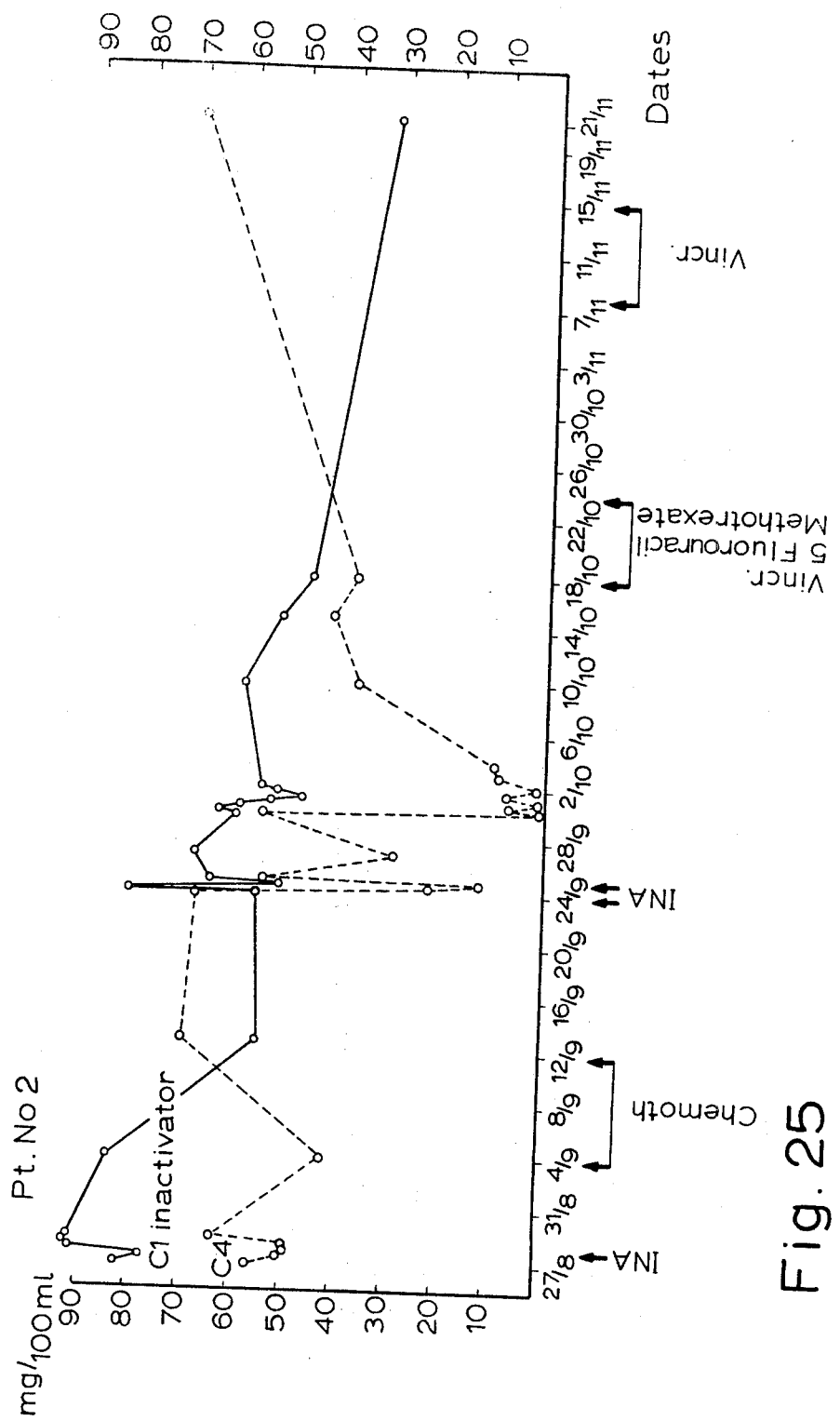

During the first INA treatment, no significant alterations in concentration of C1 inactivator and C4 were noted (FIG. 25). At the time of the first cytostatic treatment (one week after INA), the concentration of C1 inactivator and C4 decreased. After the cytostatic treatment C4 increased and C1 inactivator stabilized. During the second and third INA treatments, a fast significant rise of C1 inactivator was noted simultaneously to a significant fall in C4. The concentration of C1 inactivator then began falling, and 3 months after first INA treatment, C1 inactivator was at normal standard values. C4 showed a rise to a normal titer. One week after the first INA treatment, a relative B lymphocytosis of IgG type was noted (FIG. 26). At the second cytostatic cycle, the B lymphocytes dropped to subnormal values. At the time of second and third INA treatments, the patient revealed a slight B lymphocytosis of IgM, and simultaneously the IgG coated lymphocytes reappeared at a normal range (IgM normal range 5–25%, IgG coated cells normal range 5–20%). Three and a half months after first INA treatment, the patient has normal range of IgG and IgM coated lymphocytes.

As seen in FIG. 26, the thrombocytes dropped during the combined cytostatic treatment and INA treatment concomitantly to the development of purpura, treated with transfusions. Furthermore, a developed sinus tachycardia was observed and treated with excellent effect.

Case Story 3

A 41 year old male with histologically verified melanocarcinoma with disseminated far advanced subcutaneous metastases, previously treated with DTIC (total dose 660 mg), CCNU (total dose 20 mg) and Hydrea (total dose 5000 mg), was treated with 2 cycles of INA (pig) one week after ceased cytostatic treatment. The two cycles were given with an interval of one week (total dose 970 ml). Temperature rise maximum 41.6° C. No more INA treatment was tried because the patient was developing a brain metastasis (it is not precluded that the INA treatment would give rise to an immediate volume increase of the brain metastasis).

Clinically, the metastases grew fast during the cytostatic period of treatment. An arrest of the growth of the metastases was noted during 2 weeks following the INA treatment. This arrest was followed by a renewed growth, and cytostatic treatment was started again without any effect. The patient died 6 weeks after the last INA treatment without any signs of remission.

Figure 27:
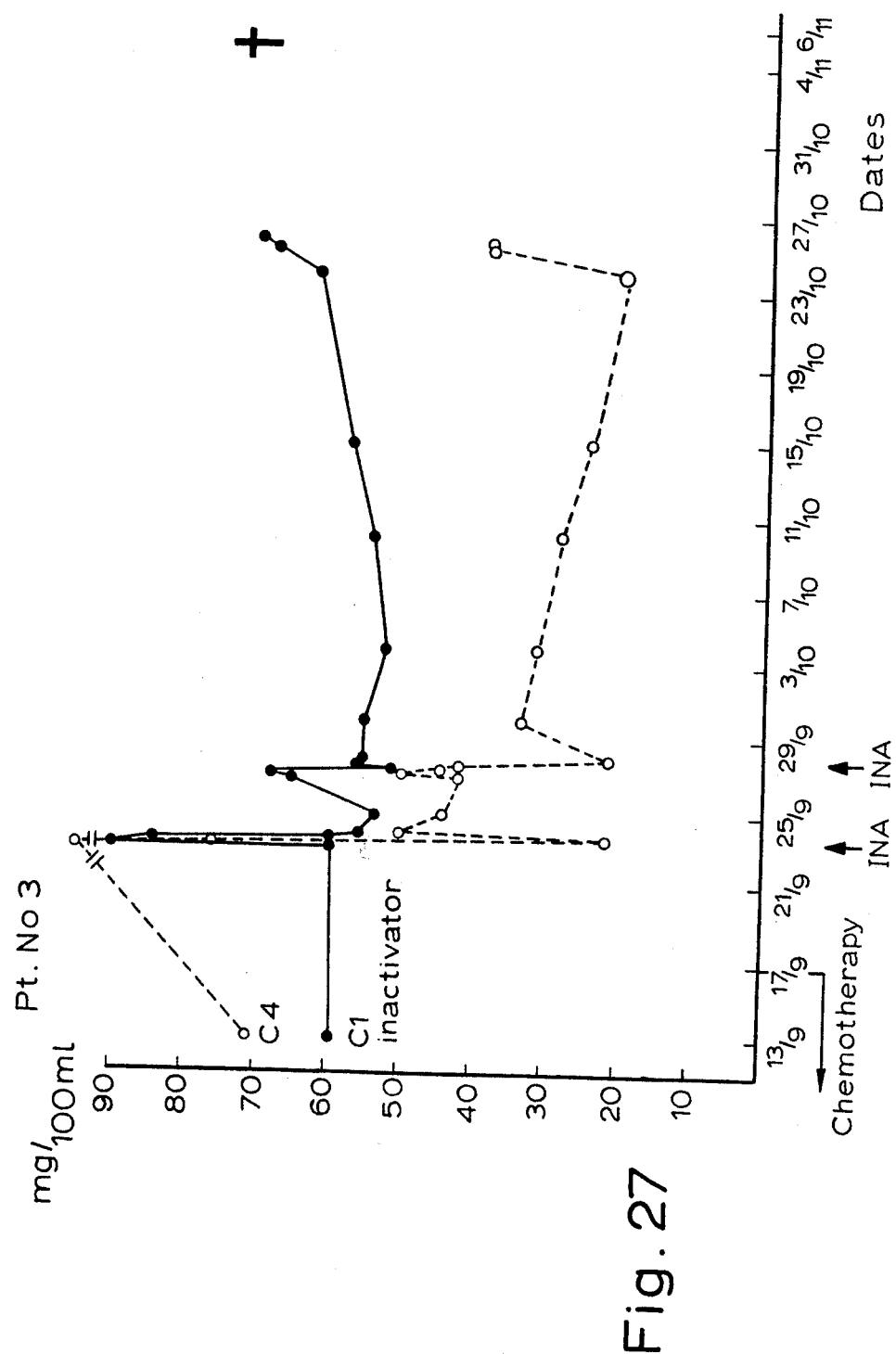

During the first and second INA treatments, a significant rise of C1 inactivator was followed by a drop to the same values as seen before INA treatment (FIG. 27). The concentration of C1 inactivator rose slowly until the death of the patient. C4 showed a drop during the INA cycles, replaced by a rise to high values after. During the first cytostatic treatment period, the patient had a relative B lymphopeni, at the INA treatment replaced by a IgG type B lymphocytosis and no significant rise in IgM coated cells (FIG. 28).

Comments on the case stories

It will be seen that in patients Nos. 1 and 3, antigen-antibody reaction occurred on the first day of the treatment with INA, as evidenced by the increase in the C1 inactivator (release of C1 IAC liberated from cells lysed by the complement system upon antigen-antibody reaction between antigenic cancer cell components and the specific antibodies thereto already present in the serum). In contrast, patient No. 2 did not show any major relase of C1 IAC during the first INA treatment, but after 7 days, a significant fall in serum C1 inactivator (C1 IA + C1 IAC) began to manifest itself concomitantly to a considerable rise in the serum uric acid and NDH (indicating cell decomposition). The second INA treatment showed the same phenomenon as the first INA treatment on patients Nos. 1 and 3, i.e., and initial sharp rise in C1 inactivator followed by a decline. It will be noted that the C4 values in the serum of patient No. 2 also declined drastically upon the 2nd and 3rd INA treatments. The C1 inactivator value of patient No. 2 became normal, and the elevated C4 level shown for patient No. 2 must be ascribed to the immunosuppressing effect on the complement system exerted by the cytostatic treatment which was given in accordance with normal cancer therapy, but not in accordance with the principles of the present invention.

The clinical effect of the INA unblocking serum in the three above-reported case stories must, of course, be viewed on the background that these patients also received other more conventional types of treatment against their cancer. Nevertheless, it is without doubt that INA unblocking serum together with the immunosuppression treatment given consecutively produced a faster and more prominent remission in two of three patients than the immunosuppression treatment could be able to produce, given in the reported quantities.

The following two case stories relate to INA treatments of longer duration.

Case story 4

A 51 year old male patient with kidney cancer with lung metastases. At the start at the INA treatment, the patient had progressively growing tumors. The INA treatment comprised intravenous administration of 1000 mg of pig IgG immunoglobulins in 200 ml of saline per day for the first 5 days, and thereafter 500 mg of pig IgG immunoglobulins per day. No treatment was performed on Saturdays and Sundays. During the first month of INA treatment, arrest of tumor growth was seen, and during the last month of the four months' treatment period, even regression was noted, although lung metastases are difficult to measure. The patient did not become immunized against the pig IgG immunoglobulins, not even after an intermittent pause of a fortnight (holiday). 1½ months after the last INA treatment, it was not possible to ascertain any growth of tumor. In the comparative immunodiffusion test, the patient's serum gave a significant C1 IAC ring at the start at the INA treatment, whereas the same test on a serum sample 1½ months after termination of the INA treatment gave a doubtfully positive C1 IAC reaction.

Case story 5

A 19 years old male with testicle teratom. Was treated with INA according to the same pattern as mentioned under Case story 4, that is, first for 5 days with 1000 mg of pig IgG per day, and thereafter for with 500 mg pig IgG per day, except Saturdays and Sundays. The INA treatment was continued for 1½ months. Prior to the start of the treatment, the patient had developed large metastases in the lungs and in mediastinum and was considered subterminal. During the INA treatment period, arrest of the tumor metastasis growth was obtained. Thereafter, the INA treatment was disrupted for reasons beyond the control of the present inventor. After 5 weeks without any treatment, renewed metastasis growth in the lungs was noted. A new treatment series was performed with chemotherapy (not in accordance with the present invention), but the tumors have grown and have spread to the liver. The patient has not shown any tumor arrest response to the chemotherapy, including adriamycin treatment, and is now cachectic and terminal.

In the comparative immunodiffusion test, the patient's serum gave a very significant C1 IAC ring at the start of INA treatment. In contrast, a serum sample from the INA treatment period was found C1 IAC-negative. A serum sample taken during the chemotherapy period showed an even larger C1 IAC ring than before the INA treatment.

Comments on case story 4

After ceased INA treatment, the patient did not receive any other form of treatment against cancer, and was not given corticosteroids, either. Even under these conditions, the tumor growth is arrested, exclusively due to the INA treatment.

Comments on case story 5

The fact that the tumor growth was arrested during INA treatment is remarkable, as this type of cancer is notoriously a very fast-growing type. Apparently, the INA treatment should have been continued for a longer period and with larger daily doses.

CAAC.

In the comparative immunodiffusion test described in the section "Diagnostic Kits", some serum samples have been found to show, in addition to a precipitation ascrible to C1 IAC, a precipitation distinctly different from said C1 IAC precipitation. This indicates the existence of an antigen which under certain circumstances seems to accompany C1 IAC, and which now has been designated CAAC (cancer associated antigen complex).

One of the rather easily ascertainable differences between C1 IAC and CAAC is that while C1 IAC looses its immunological properties (its ability to precipitate with its antibody in immunological tests) by heat treatment, CAAC retains its ability to precipitate with antibody even after heating at 60° C. for 30 minutes, as demonstrated by both immunoelectroforesis and comparative immunodiffusion.

In the following, the presently available data concerning CAAC are stated (1) Grabar agarose gel immunoelectrophoresis In Grabar agarose gel immunoelectrophoresis, the position of the CAAC total precipitate is totally within the $\gamma$ area.

This indicates that CAAC shows a relatively strong negative electrical charge and is not an immunoglobulin (immunoglobulins precipitate in the $\gamma$ to $\beta$ area), and is, furthermore, not identical to C1 IAC/C1 IA, the precipitate of which is in the $\alpha_2$ area.

(2) Immunoelectrophoresis

In immunoelectrophoresis, CAAC precipitates with its corresponding antibody even after a prior heat treatment at 60° C. for 30 minutes, whereas the precipitates of C1 IAC and C1 IA are seen to disappear already after heat treatment at 56° C./30 minutes. However, this heat treatment of CAAC seems to give rise to the formation of a new precipitate in addition to the precipitate at the CAAC precipitate position. The CAAC-derived new precipitate is in the $\alpha$-$\beta$ zone. Further details are stated below in connection with the discussion of FIGS. 31 and 32.

(3) Temperature cycling

It has been found that CAAC is superior to C1 IAC with respect to its resistance to repeated freezing/thawing cycles, and can be found in even some sera stored at −20° for approximately 12 months.

(4) Preparative ultracentrifugation

In preparative ultracentrifugation at 4° C., gravitation 178.880 G, run fo 4 hours, CAAC is present in the supernatant, but not in the lipoprotein fraction. This applies to the various fluids tested, that is, patient serum, plasma and pleural or ascites exsudate.

(5) Treatment with neuraminidase does not remove CAAC's ability to precipitate with its corresponding antibody.

(6) CAAC retains its ability to form precipitation with its corresponding antibody in immunological tests after exposure to pH values in the range 5.6–10.7.

(7) Antisera precipitating with CAAC, but not with C1 IAC, can be produced in host animals by immunizing the animals with heat inactivated (56° C./30 minutes) C1 IAC/C1 IA DEAE Sephadex ® A50 antigen. The resulting antisera can be incorporated in 1% agarose gel to prepare e.g. CAAC-specific comparative immunodiffusion test kits of a type corresponding to the C1 IAC comparative immunodiffusion test kit described in the section "Diagnostic Kits". When the above-mentioned heat-treated C1 IAC/C1 IA DEAE Sephadex ® A50 antigen itself is applied in the sample serum hole of the comparative immunodiffusion test, a CAAC precipitation ring results, both with an immunodiffusion gel containing CAAC-specific antiserum prepared from host animals immunized with the heat-treated antigen, and with an immunodiffusion gel containing C1 IAC- and CAAC-specific antiserum from host animals immunized with the non-heat-treated antigen. When patient serum containing both C1 IAC and CAAC, or only CAAC, is applied in the CAAC-specific comparative immunodiffusion test, a CAAC precipitation will result, whereas the same patient serum, if containing both C1 IAC and CAAC, will give two precipitations in the C1 IAC(CAAC)-responding test prepared using serum from host animals immunized with non-heat treated antigen, and, if containing only CAAC, will give only one precipitation ring in the C1 IAC(CAAC)-responding test.

The fact that CAAC has been found in the above-mentioned immunological precipitation tests shows that the antiserum used in the experiments contained antibodies which were able to precipitate with CAAC. This indicates that CAAC must have been present in the vaccine originally administered to the host animal in question for preparing the antiserum. It can be said with certainty that CAAC has been found using antisera produced in host animals which were, besides vaccination with C1 IAC$_{pure}$ or other combinations of C1 IAC/C1 IA antigens, also immunized with C1 IAC/C1 IA DEAE Sephadex ® A50, whereas it is not certain whether vaccines not containing this material give rise to the formation of antibodies against CAAC. This, on its side, indicates that in the preparation of C1 IAC/C1 IA DEAE Sephadex ® A50, CAAC follows C1 IAC/C1 IA in the various ion exchange and salting out procedures described in the above section "Purification of C1 IAC/C1 IA from Pleural/Ascites Fluid from Cancer Patients", and hence, cannot be an immunoglobulin, because immunoglobulins are in the euglobulin fraction which is salted out with saturated ammonium sulfate below 33% addition thereof to serum, whereas CAAC was apparently not salted out even after 50% addition of saturated ammonium sulfate to the serum.

As the vaccine described above has often been prepared using cancer cell culture medium and pleural/ascites exsudate from a very small number of patients, and as all antisera produced using C1 IAC/C1 IA DEAE Sephadex ® A50 as part of the vaccine have been found to be able to give the typical CAAC precipitate (which appears even after heat treatment of the sample of 60° C. for 30 minutes) with CAAC-containing patient serum samples, this seems to indicate that CAAC is always present in the vaccine, which on its side means that CAAC is with great likelihood present as a relatively significant proportion of the protein content of the pleural/ascites exsudate. As noted above, not all cancer patient serum samples show any content of CAAC, at least not any content which can be demonstrated by the present immunological test methods, but based upon the above conclusions it seems that pleural/ascites exsudate from cancer patients will with great likelihood always contain CAAC. This renders it probable that patient tissue fluids from areas or domaines which are cancer cell infiltrated, will contain CAAC. This might also indicate that the more active a cancer is, the more CAAC will be found in the patient's serum. The findings so far obtained seem to confirm this: in the comparative immunodiffusion, a CAAC Precipitation ring with a large diameter has been found to often coincide with an active state of cancer. Based upon the above findings, it may be said that CAAC is a cancer associated antigen, and it is believed to be a protein or protein-like substance (present in the pseudo-globulin part) of low antigenicity in the human system. It cannot be precluded that CAAC could be an antigen consisting of a C1 molecule with attached C1 IAC, vide in this context Nagaki et al., loc. cit.

As heat treatment (56° C. for 30 minutes) of vaccine prepared without the above-mentioned content of C1 IAC/C1 IA DEAE Sephadex ® A50 resulted in a material which in itself is not able to give any precipitation with antiserum prepared on pig or sheep using a vaccine comprising C1 IAC/C1 IA DEAE Sephadex ® A50, whereas heat treatment of the vaccine types containing C1 IAC/C1 IA DEAE Sephadex ® A50 results in a material which in itself in each single case seems able to give precipitation with antiserum prepared using a non-heat treated vaccine containing C1 IAC/C1 IA DEAE Sephadex ® A50, this is a further indication that it is the C1 IAC/C1 IA DEAE Sephadex ® A50 part of the vaccine which contains a significant proportion of CAAC and in the host animal gives rise to the formation of antibodies against CAAC.

For the preparation of an antiserum with specificity against CAAC, but not against C1 IAC/C1 IA, a vaccine may be used (for administration to the host animals) which has been prepared with incorporation of C1 IAC/C1 IA DEAE Sephadex ® A50, but which, prior to administration to the host animal, has been heat treated at a temperature/time which is known to destory the precipitation property of C1 IAC/C1 IA, for example 56° C. for 30 minutes. Such antisera or antibodies with specificity against CAAC are valuable diagnostic materials and can be used in the various tests described for the differentiation between C1 IAC and CAAC in patient serum. Also, it is envisaged that antibodies with specificity against CAAC would be useful in cancer therapy, in analogy to the C1 IAC antibodies described above.

Based upon the experience so far obtained, it may be stated that a positive CAAC reaction in the immunodiffusion test is indicative of a malignant disease or an "autoimmune" disease such as LED. Moreover, as stated above, it seems that positive CAAC reactions are often found in cases of very active cancers. If it is true that CAAC is a C1 molecule with attached C1 IAC, this would be in good conformity with such findings.

In the comparative immunodiffusion, a CAAC precipitation can be distinguished from a C1 IAC precipitation by heat inactivation (60° C. for 30 minutes) of the serum sample (must be performed also on the negative standard serum). If the precipitation remains in the heat-inactivated serum, it is a CAAC precipitation. In some cases, a distinct C1 IAC ring and a distinct CAAC ring are found in the immunodiffusion test, but also, the presence of a CAAC ring without any accompanying C1 IAC ring has often been seen.

Figure 31:
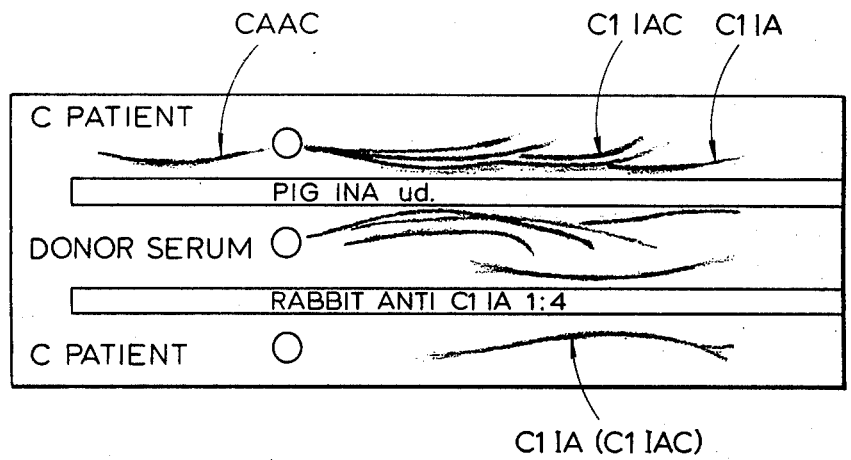
FIGS. 31 and 32 are Grabar-Scheidegger immunoelectrophoresis runs.

FIG. 31 shows a Grabar-Scheidegger immunoelectrophoresis of serum derived from a patient suffering from cancer, compared with serum from blood donor. The electrophoresis was run at 150 V/90 minutes at room temperature, followed by immunodiffusion against undiluted pig (or sheep) serum containing antihuman C1 IAC/C1 IA in the upper through, and rabbit antihuman C1 IA, diluted 1:4, in the lower through. The immunodiffusion was performed at room temperature for 24 hours. After elution with saline, the slide was stained with Coomasie Blue. The slide shows CAAC situated in the $\gamma$ zone in the serum from the patient suffering from cancer, but not detectable in serum from blood donor (middle hole). Furthermore, C1 IA with its typical gull wing form is seen in the $\alpha_2$ zone. C1 IAC is seen in the $\alpha_2$ zone near the $\beta$ zone in the cancer patient serum.

Figure 32:
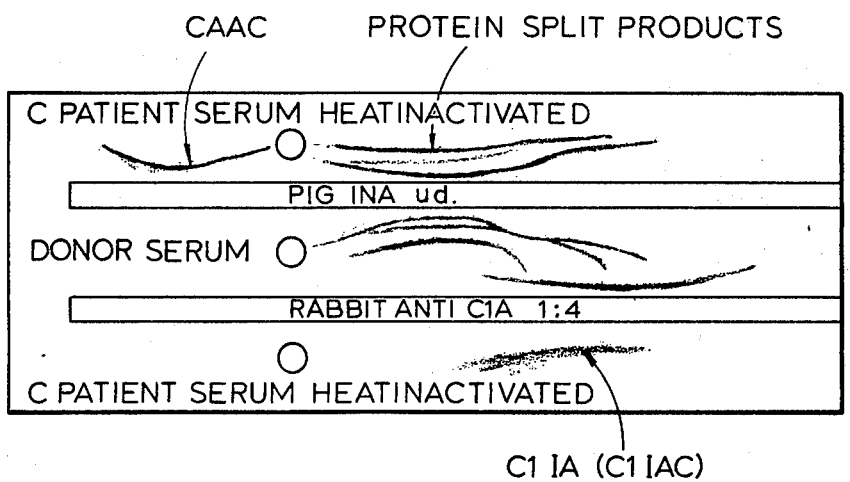

Referring to FIG. 32, in heat inactivated cancer patient serum, a precipitation is still present at the CAAC position in the $\gamma$ zone (heat inactivation at 56° C. for 30 minutes). In addition, another precipitation becomes visible. This precipitation is positioned in the $\alpha$-$\beta$ zone in the cancer serum part. It is not possible to judge whether the precipitate in this zone is due to splitting of CAAC or of another heat labile protein complex. Most likely, the precipitate is due to a splitting of a protein complex, changing the position of this part of the protein complex to this zone.

Using the comparative immunodiffusion method with a gel containing antiserum from a pig which had been immunized using heat-treated (56° C./30 minutes) C1 IAC/C1 IA DEAE Sephadex ® A50, serum samples from two patients suffering from verified LED, two patients suffering from cancer (CLL and teratom, respectively), and one blood donor were examined, using standard negative serum as reference. The samples from the two LED patients gave CAAC ring precipitates. (The C4 serum level was found to be low in serum from these patients, such as is generally the case with LED). No CAAC ring developed in the tests with the serum samples from the two cancer patients, nor with the serum sample from the blood donor, indicating that no CAAC was present in these serum samples.

I claim:

1. Antisera and antibodies with specificity against a human cancer cell associated α-neuramino glycoprotein having inhibitory activity upon C1 esterase hydrolyzing effect, and inhibitory effect on C1 activation of C4 as shown by the inhibition of complement haemolysis.

2. A process for preparing the antisera claimed in claim 1, comprising immunizing non-human host animals with a human cancer cell associated α-neuramino glycoprotein having the properties stated in claim 1, and harvesting serum from the immunized animal.

3. A human cancer cell associated protein, termed C1 IAC, said protein being an α-neuramino glycoprotein showing the following characteristics:
   (1) inhibitory activity on C1 esterase hydrolyzing effect;
   (2) inhibitory effect on C1 activation of C4 as shown by the inhibition of complement haemolysis;
   (3) lack of effect upon the clotting time of plasma;
   (4) inhibitory effect on fibrinolysis;
   (5) inhibitory effect against the plasma fibrinolytic system as demonstrated by fibrin agarose electrophoresis;
   (6) progressive loss of inhibitory activity on C1 esterase hydrolyzing effect below pH 5.5 and above pH to 10.5;
   (7) loss of inhibitory activity on C1 esterase hydrolyzing effect upon incubation at temperatures exceeding 56° C. for 30 minutes;
   (8) in Grabar-Scheidegger immunoelectrophoresis against rabbit antihuman C1 IA, a non-"gull wing" configurated precipitate which extends into the $\beta$ zone when the immunoelectrophoresis is run in the presence of calcium lactate;
   (9) immunoelectrophoretical identity with C1 IA in tandem-crossed immunoelectrophoresis in gel containing rabbit antihuman C1 IA;
   (10) loss of ability to precipitate with rabbit antihuman C1 IA upon treatment with neuraminidase;
   (11) in Ouchterlony immunodiffusion, yielding a precipitate different from the C1 IA precipitate against antiserum from host animals which are able to distinguish between C1 IA and C1 IAC, such as from pigs of Danish "Landrace";
   (12) a molecular weight of 110,000–130,000, when estimated by the gel filtration technique;
   (13) a sedimentation constant $s°_{20,w}$ of 6.2 S.

4. A protein, termed C1 IAC, according to claim 3, in substantially pure form.

5. A method for immunizing a non-human animal immunizable against C1 IAC said method comprising administering to said animal an amount of C1 IAC effective to immunize said animal thereto.

6. Antisera, antibodies, antibody fragments, antibody modifications, and antibody derivatives with specificity against C1 IAC.

7. Antisera and antibodies according to claim 6, comprising substantially pure pig IgG immunoglobulins.

8. Antisera and antibodies according to claim 6, labelled with a radioactive isotope.

9. Antisera and antibodies according to claim 6, chemically bound to a cytostatic.

10. Matrix-immobilized antisera and antibodies reactive with C1 IAC.

11. A method for passive immunization therapy of cancer diseases comprising administering an immunologically effective amount of anti C1 IAC to a human being.

12. A reagent comprising anti C1 IAC.

13. A diagnostic kit comprising anti C1 IAC incorporated in a gel layer, said gel layer being disposed on a support; and a container therefor.

14. A diagnostic kit according to claim 13, wherein the gel is an agarose gel.

15. A diagnostic kit according to claim 14, wherein the agarose gel layer is provided with holes adapted for use in radial immuno-diffusion techniques.

* * * * *